US012799116B2

(12) United States Patent
Zhou et al.

(10) Patent No.: US 12,799,116 B2
(45) Date of Patent: Nov. 17, 2026

(54) CYCLIC FORMYL AND CYCLIC KETONE COMPOUNDS, PREPARATION METHOD THEREFOR, AND PHARMACEUTICAL USE

(71) Applicant: NANJING TECH UNIVERSITY, Nanjing (CN)

(72) Inventors: Guo-Chun Zhou, Nanjing (CN); Bin Xu, Nanjing (CN); Feng Li, Nanjing (CN); Xia Sun, Nanjing (CN); Binli Jiang, Nanjing (CN); Kun Dai, Nanjing (CN)

( * ) Notice: Subject to any disclaimer, the term of this patent is extended or adjusted under 35 U.S.C. 154(b) by 1009 days.

(21) Appl. No.: 17/610,702

(22) PCT Filed: May 14, 2020

(86) PCT No.: PCT/CN2020/090286

§ 371 (c)(1),
(2) Date: Nov. 12, 2021

(87) PCT Pub. No.: WO2020/228783

PCT Pub. Date: Nov. 19, 2020

(65) Prior Publication Data

US 2022/0235057 A1 Jul. 28, 2022

(30) Foreign Application Priority Data

May 14, 2019 (CN) ........................ 201910399032.6

(51) Int. Cl.

| | |
|---|---|
| ***C07D 487/04*** | (2006.01) |
| ***A61P 31/04*** | (2006.01) |
| ***A61P 31/14*** | (2006.01) |
| ***C07D 209/08*** | (2006.01) |
| ***C07D 209/42*** | (2006.01) |
| ***C07D 209/52*** | (2006.01) |
| ***C07D 211/34*** | (2006.01) |
| ***C07D 215/48*** | (2006.01) |
| ***C07D 217/26*** | (2006.01) |
| ***C07D 233/60*** | (2006.01) |
| ***C07D 471/04*** | (2006.01) |
| ***C07F 5/02*** | (2006.01) |

(52) U.S. Cl.

CPC ............ *C07D 487/04* (2013.01); *A61P 31/04* (2018.01); *A61P 31/14* (2018.01); *C07D 209/08* (2013.01); *C07D 209/42* (2013.01); *C07D 209/52* (2013.01); *C07D 211/34* (2013.01); *C07D 215/48* (2013.01); *C07D 217/26* (2013.01); *C07D 233/60* (2013.01); *C07D 471/04* (2013.01); *C07F 5/022* (2013.01)

(58) Field of Classification Search

None

See application file for complete search history.

(56) References Cited

FOREIGN PATENT DOCUMENTS

| | | | | | |
|---|---|---|---|---|---|
| CN | 101774874 | A | * | 7/2010 | |
| CN | 101842098 | A | | 9/2010 | |
| CN | 106810552 | A | | 6/2017 | |
| CN | 107814803 | A | | 3/2018 | |
| WO | 2018020004 | A1 | | 2/2018 | |
| WO | WO-2020169682 | A1 | * | 8/2020 | ........... C07C 243/36 |

OTHER PUBLICATIONS

Guo et al. Benzyne-Promoted Curtius-Type Rearrangement of Acyl Hydrazides in the Presence of Nucleophiles & Supplemental Data, Asian Jn of Organ Chem, published 2018. (Year: 2018).*

STN Registry Database. Registry No. 1572152-96-5. Published 2014. Retrieved from the Internet on Oct. 23, 2025, https://www.stn.org (Year: 1986).*

STN Registry Database. Registry No. 100318-24-9. Published 1986. Retrieved from the Internet on Oct. 23, 2025, https://www.stn.org (Year: 1986).*

Winterfeld et al. STN Caplus Abstract of Synthesis of 2-azaindolizzidines and some derivatives. Archiv der Pharmazie and Berichte der Deutschen Pharmazeutischen Gesellschaft. Published 1960. (Year: 1960).*

STN Registry Database. Registry No. 1837753-97-5. Published 2015. Retrieved from the Internet on Oct. 31, 2025, https://www.stn.org.*

STN Registry Database. Registry No. 1580971-85-2. Published 2014. Retreived from the Internet on Feb. 17, 2026, https://www.stn.org. (Year: 2014).*

Xu, Xi et al., "Exploring the tetrahydroisoquinoline thiohydantoin scaffold blockade the androgen receptor as potent anti-prostate cancer agents", European Journal of Medicinal Chemistry, vol. 143, Oct. 14, 2017, p. 1325-1344.

Xie,Jianwei et al., "Pyrrole-2-carbohydrazides as Ligands for Cu-Catalyzed Amination of Aryl Halides with Amines in Pure Water", European Journal of Organic Chemistry, May 6, 2010, p. 3219-3223.

Weng, Zhibing et al., "Identification of fused bicyclic derivatives of pyrrolidine and imidazolidinone as dengue virus-2 NS2B-NS3 protease inhibitors", European Journal of Medicinal Chemistry, vol. 125, Sep. 21, 2017, p. 751-759.

(Continued)

*Primary Examiner* — Lauren Wells

(57) ABSTRACT

The present invention provides a cycloyl formyl and cycloyl ketone compounds, a preparation method therefor, and a pharmaceutical use. The present invention finds that the compounds shown in formula (I) better inhibits Zika virus and dengue virus infection and replication, may be used as a drug for treating and preventing diseases caused by Zika virus and dengue virus, and may also become a drug for treating and preventing diseases caused by other flaviviruses, such as yellow fever, West Nile virus infection, Japanese encephalitis, AIDS caused by HIV etc., and diseases caused by hand, foot and mouth virus infection etc. The compounds may treat disease caused by bacterial infections, including inflammatory bowel disease ulcerative colitis and Crohn's disease, diseases caused by *Escherichia coli*, diseases caused by *Staphylococcus aureus* etc., and diseases caused by *Acinetobacter baumannii.*

1 Claim, No Drawings

(56) References Cited

OTHER PUBLICATIONS

Sun, X.H et al., "3D-QSAR studies of quinoline ring derivatives as HIV-1 integrase inhibitors", SAR and QSAR in Environmental Research, vol. 23, No. 7 and 8, Dec 31, 2012, p. 683-703.

Barluenga, Jose et al., "Asymmetric Benzopentaannulation from Tungsten ((−)-Menthyloxy)(aryl)carbene Complexes, Alkynyllithiums, and Methyl Triflate", J. Am. Chem. Soc, vol. 120, Nov. 6, 1998, p. 12129-12130.

Zhou, Xiaorong et al., "Rh-Catalyzed annulations of N-methoxybenzamides with ketenimines: synthesis of 3-aminoisoindolinones and 3-diarylmethyleneisoindolinones with strong aggregation induced emission properties", Chemical Communication, vol. 52, Aug. 2, 2016, p. 10676-10679.

Unhale, Rajshekhar A. et al., "A chiral Brønsted acid-catalyzed highly enantioselective Mannich-type reaction of a-diazo esters with in situ generated N-acyl ketimines", Chemical Communication, vol. 54, Mar. 14, 2018, p. 3516-3519.

Clayden, Jonathan et al., "2,3-Dihydroisoindolones by cyclisation and rearomatisation of lithiated benzamides", Tetrahedron Letters, vol. 44, Dec 31, 2003, p. 3059-3062.

Katritzky, Alan R. et al., "Novel Syntheses of Enantiopure Hexahydroimidazo[1, 5-b]isoquinolines and Tetrahydroimidazo[1, 5-b]isoquinolin-1(5H)-ones via Iminium Cation Cyclizations", The Journal of Organic Chemistry, vol. 67, Oct. 10, 2002, p. 8224-8229.

Clayden, Jonathan et al., "Dearomatizing Anionic Cyclization of Substituted N-Cumyl-N-benzyl-benzamides on Treatment with LDA:Synthesis of Partially Saturated Substituted Isoindolones", Organic Letters, vol. 2, No. 26, Nov. 29, 2000, p. 4229-4232.

Registry Copyright 2020 ACS on STN, May 21, 2018, CAS:2224445-03-6.

Registry Copyright 2020 ACS on STN, May 27, 2014, CAS: 1608941-77-0.

* cited by examiner

CYCLIC FORMYL AND CYCLIC KETONE COMPOUNDS, PREPARATION METHOD THEREFOR, AND PHARMACEUTICAL USE

CROSS-REFERENCE TO RELATED APPLICATIONS

This application is a 371 application of the International Patent Application No. PCT/CN2020/090286 filed on May 14, 2020, and the disclosures of which is incorporated herein by reference in its entirety.

FIELD OF THE INVENTION

The present invention relates generally to the technical field of medicinal and pharmaceutical chemistry. More specifically, it relates to a cycloyl formyl and cycloyl ketone compounds, a preparation method therefor, and a pharmaceutical use.

BACKGROUND

Flaviviridae such as Zika virus (ZIKV), dengue virus (DENV), flavivirus (YFV), West Nile virus (WNV), Japanese encephalitis virus (JEV), and Chikungunya virus (CHIKV) of the genus Alphavirus are all arboviruses, and they are similar in many aspects of their life cycle. The major vectors of these arboviruses are Aedes mosquito (including *Aedes aegypti; Aedes albopictus* and *Aedes polynesiensis*). They are one of the largest mosquitoes in the world and exist in all continents of the world except *Antarctica*. In general, dengue-like disease symptoms appear 3-14 days after being bitten by the contagious *Aedes* (average 4-7 days).

Especially, DENV has 4 serotypes. Although the 4 serotypes of DENV have 65-70% similarity, re-infection of different serotypes of DENV can cause antibody-dependent enhancement (ADE). In recent years, studies have found that this ADE effect may also occur in ZIKV cross-infection after DENV infection, leading to some uncertainty. ZIKV infection was prevalent in Brazil in 2015-2016, and DENV also occurred in Brazil in 2016. It is unknown whether this is because cross-infection has contributed to the two epidemics, and may increase the virulence of viruses, or even cause the mutation of virus genes. Several reports in □ Lancet Infectious Diseases□ from 2016 to 2017 stated that ZIKV infection outbreaks in Vietnam and Singapore in 2016 have been found to have genetic mutations. The earliest ZIKV imported from South America may be a variant of ZIKV that was originally spread in Southeast Asia rather than imported from South America.

Under the influence of many factors such as global environmental degradation and global warming, the dengue fever and Zika epidemics have tended to expand in recent years. However, there is currently only one dengue vaccine in a restricted area. There is no. Zika virus vaccine or other vaccines, and no effective anti-Zika virus or anti-dengue virus drugs can be used for clinical treatment of dengue fever. At present, clinical treatment is mainly intensive supportive therapy, in which maintaining fluid balance is the main means. Therefore, drug research on diseases caused by arboviruses such as Zika virus and Dengue virus is extremely important and urgent.

Other arboviruses have similar symptoms to Zika virus and Dengue virus, and may also mutate into mutant viruses with higher virulence.

SUMMARY OF THE INVENTION

This section aims to summarize some aspects of the embodiments of the present invention and to briefly describe some preferred embodiments. Simplification or omission may be made in this section, the abstract of the specification, and the title to avoid obscuring the purposes of this section, the abstract of the specification, and the title. Such simplification or omission may not be used to limit the scope of the present invention.

The present invention is made in view of the technical problems as above-mentioned. The present invention provides a ring-fused compound containing the corresponding active of five-membered ring, and its derivatives, stereoisomers, cis-trans isomers, or pharmaceutically acceptable salts thereof. Therefore, as one aspect of the present invention, the present invention provides a cycloyl formyl and cycloyl ketone compounds, a preparation method therefor, and a pharmaceutical use.

To solve the technical problems as above-mentioned, the present invention provides the following solutions: compounds, isomers or pharmaceutically acceptable salts thereof as shown in Formula (I).

(I)

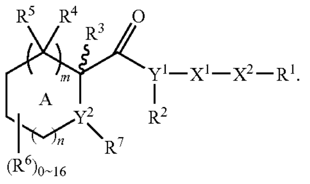

Ring A includes any of a substituted or unsubstituted non-aromatic ring, a non-aromatic heterocyclic ring, a carbon aromatic ring, or an aromatic heterocyclic ring; $X^1$ and/or $X^2$ include any one of empty, O, S, S(O), $S(O_2)$, $NR^8$, C(O), $(C(R^9R^{10})_p$, and $X^1$ and $X^2$ are not O, S, S(O), $S(O_2)$ at the same time; $Y^1$ and $Y^2$ are the same or different, and $Y^1$ and $Y^2$ are respectively one of N and $CR^{11}$; m and/or n are integers starting from 0 to 6, and m+n is an integer starting from 0 to 6; p is an integer starting from 1 to 6. When one of $X^1$ or $X^2$ is $NR^8$ and the other is empty, $Y^1$ is N, and $R^1$ includes one or more of substituted or unsubstituted benzene rings, no cyclic structure is formed between $R^2$ and $R^3$ and/or $R^4$ and/or $R^5$ and/or $R^6$ and/or $R^7$ and/or $R^8$. When $R^4$ and/or $R^5$ and/or $R^7$ connecting to N on any of two sides of the formyl group are one or more of acyl group or carbamoyl group or formate group or hydrazide group or alkyl group with six or less carbons, the ring A does not include substituted or unsubstituted pyrrole rings. When one of $X^1$ or $X^2$ is empty, $Y^1$ is N, and when a cyclic structure is formed between $R^2$ and $R^4$ and/or $R^5$ and/or $R^7$ connecting to N on any of two sides of the formyl group, the ring A does not include pyrrole ring and 4-substituted pyrrole ring. $R^1$ to $R^{11}$ are H, CN, $CF_3$, nitro, halogen, optionally substituted alkyl, optionally substituted cycloalkyl, optionally substituted heterocyclic group, optionally substituted alkoxy, optionally substituted alkylthio, optionally substituted alkylthio monoxide (sulfoxide), optionally substituted alkylthio dioxide (sulfone), optionally substituted sulfonyl, carboxylic acid, carboxylate, optionally substituted ester group, amide, optionally substituted amidoamino group, optionally substituted alkene group, optionally substituted cycloalkene group, optionally substituted arylalkyl group, optionally substituted heterocyclic arylalkyl group, optionally substituted aromatic hydrocarbon group, optionally substituted heterocyclic aromatic hydrocarbon group, optionally substituted aromatic olefin group, optionally substituted heterocyclic aromatic alkene group. The substituent is selected from halogen, cyano, nitro, $C_{1-6}$ alkyl, $C_{1-6}$ haloalkyl, $C_{1-6}$ alkoxy, $C_{1-6}$ alkylthio or $C_{2-6}$ alkenyl, carboxyl, carboxylate, sulfonate. A double bond can be formed between $X^1$ and $X^2$. A 4- to 6-membered fused ring can be formed between $X^1$ and $X^2$. A 4- to 6-membered ring can be formed between $X^1$ and $R^2$. A double bond can be formed between $X^1$ and $R^{11}$ and/or $Y^1$. A 4- to 6-membered ring can be formed between $X^1$ and $R^{11}$ and/or $Y^1$. A 4- to 6-membered ring can be formed between $R^2$ and $R^7$, or $R^2$ and $R^4$, or $R^2$ and $R^5$, or $R^2$ and $R^6$. A 4- to 6-membered spiro ring can be formed between $R^2$ and $R^3$. A double bond can be formed between adjacent substituents. A ring can be formed between adjacent substituents, and the ring may be carbocyclic or heterocyclic ring, aromatic ring, or non-aromatic ring. Among them, the adjacent substituents include $R^3$ and $R^7$, a ring can be formed between the geminal substituents from the same carbon, and the ring may be one or more of carbocyclic, heterocyclic ring, aromatic ring, or non-aromatic ring. Among them, the geminal substituents from the same carbon include $R^9$ and $R^{10}$, $R^7$ and $R^{11}$. A bridged ring can be formed between the non-geminal and non-vicinal substituents from the different carbons, or formed between the non-geminal and non-vicinal substituents from different nitrogens, and the bridged ring may be carbocyclic or heterocyclic. Isotopic substitutions of all elements are considered equivalent. The chiral center in the skeleton structure may be in the R configuration or the S configuration. The chiral group on the substituent may be in the R configuration or the S configuration.

Preferably, in the present invention, the compounds, isomers or pharmaceutically acceptable salts thereof are shown in Formula (II), in which ring B is a fused ring formed by connecting any two adjacent positions of ring A, which can be any substituted or unsubstituted non-aromatic ring, non-aromatic heterocyclic ring, carboaromatic ring or aromatic heterocyclic ring.

(II)

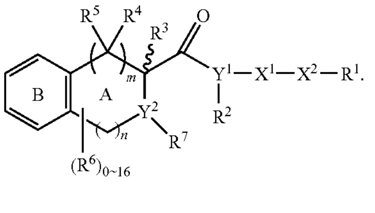

Preferably, in the present invention, the compounds, isomers or pharmaceutically acceptable salts thereof are shown in Formula (III)-1, Formula (III)-2.

(III)-1

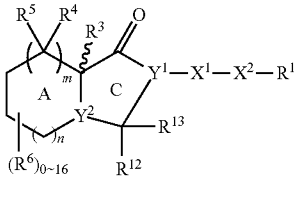

or

-continued (III)-2

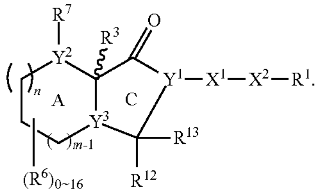

Ring C is a five-membered ring structure, which can be a five-membered carbocyclic ring or a five-membered heterocyclic ring, $Y^3$ is N or $CR^4$ or $CR^5$. When one of $X^1$ and $X^2$ is empty and $Y^1$ and $Y^2$, or $Y^1$ and $Y^3$ are N, the ring A cannot be a pyrrole ring or 4-substituted pyrrole ring. Two bonds of C—$R^{12}$ and $R^{13}$ from the same carbon do not form carbonyl or thiocarbonyl. $R^{12}$ and $R^{13}$ are H, CN, $CF_3$, nitro, halogen, optionally substituted alkyl, optionally substituted cycloalkyl, optionally substituted heterocyclic group, optionally substituted alkoxy, optionally substituted alkylthio, optionally substituted alkylthio monoxide (sulfoxide), optionally substituted alkylthio dioxide (sulfone), optionally substituted sulfonyl, carboxylic acid, carboxylate, optionally substituted ester group, amide, optionally substituted amidoamino group, optionally substituted alkene group, optionally substituted cycloalkene group, optionally substituted arylalkyl group, optionally substituted heterocyclic arylalkyl group, optionally substituted aromatic hydrocarbon group, optionally substituted heterocyclic aromatic hydrocarbon group, optionally substituted aromatic olefin group, optionally substituted heterocyclic aromatic alkene group. The substituent is selected from halogen, cyano, nitro, $C_{1-6}$ alkyl, $C_{1-6}$ haloalkyl, $C_{1-6}$ alkoxy, $C_{1-6}$ alkylthio or $C_{2-6}$ alkenyl, carboxyl, carboxylate, sulfonate.

Preferably, in the present invention, the compounds, isomers or pharmaceutically acceptable salts thereof are shown in Formula (IV)-1, Formula (IV)-2, in which the ring A and ring B are optionally substituted or unsubstituted non-aromatic ring, non-aromatic heterocyclic ring, carboaromatic ring or aromatic heterocyclic ring. Ring C is a five-membered ring structure, which can be a five-membered carbocyclic ring or a five-membered heterocyclic ring. $Y^3$ is N, or $CR^4$, or $CR^5$.

(IV)-1

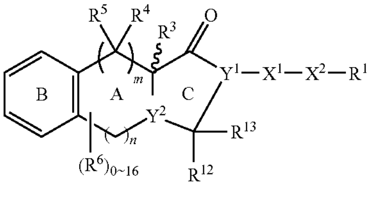

or (IV)-2

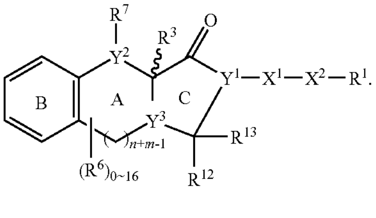

Preferably, the compounds, isomers or pharmaceutically acceptable salts thereof according to the present invention are shown in Formula (V).

(V)

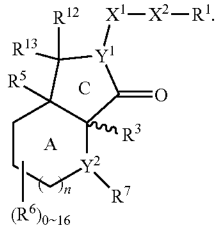

Preferably, the compounds, isomers or pharmaceutically acceptable salts thereof according to the present invention are shown in Formula (VI).

(VI)

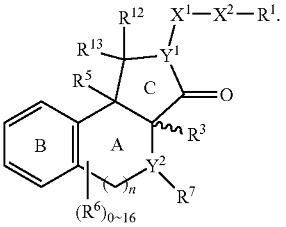

Preferably, the compounds, isomers or pharmaceutically acceptable salts thereof according to the present invention are shown in Formula (VII).

(VII)

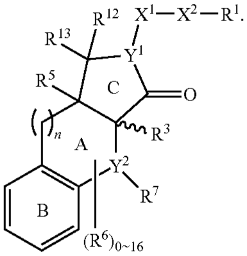

Preferably, the compound, isomer or pharmaceutically acceptable salt thereof according to the present invention is characterized in that the compound includes:

ZFD-33A+B

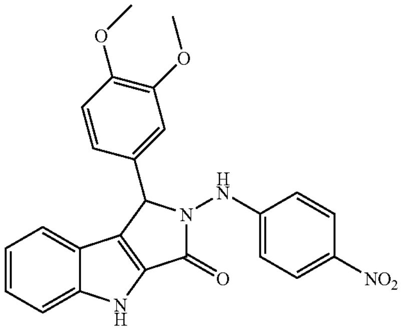

-continued

ZXN-7

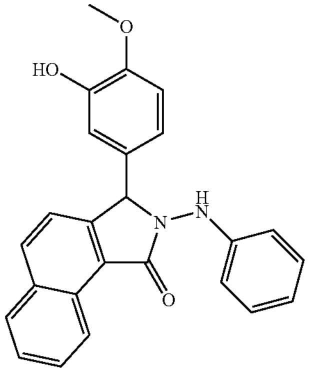

ZXN-10

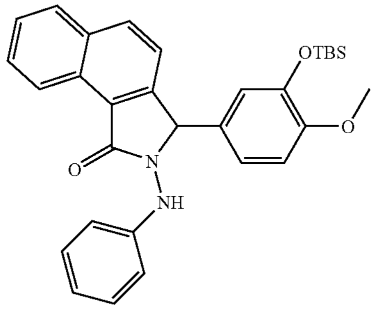

ZXD-157B

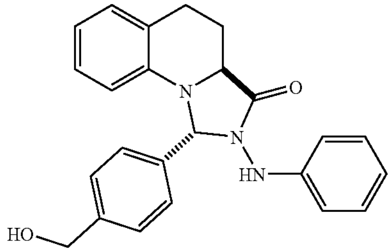

ZXD-165

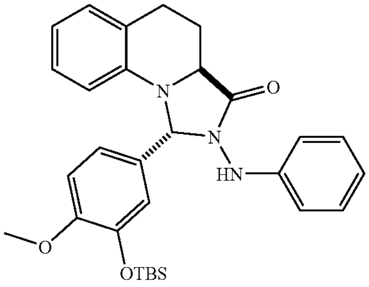

ZXD-167

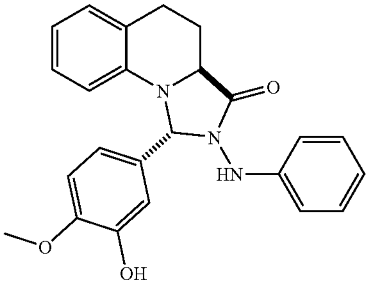

-continued
ZXD-176
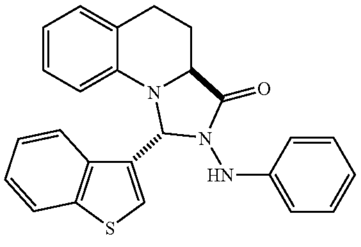
ZXD-176A
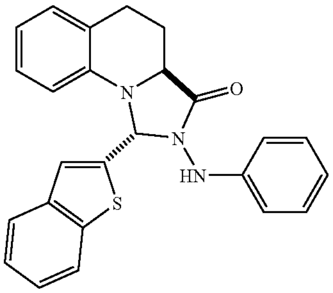
ZXD-176B
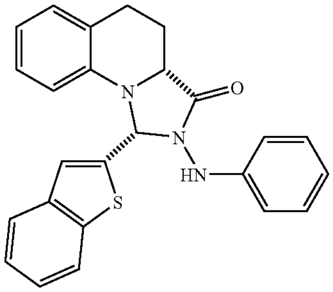
ZXD-181B
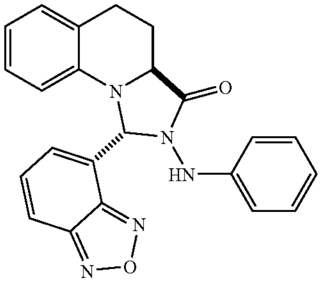
ZXD-241B
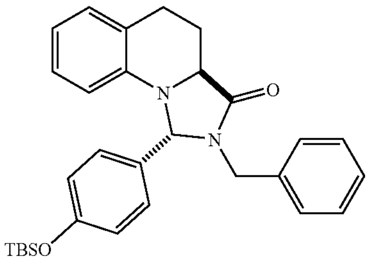
-continued
ZXD-131A
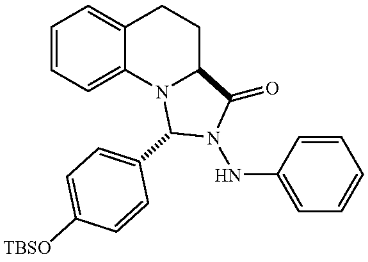
ZXD-131B
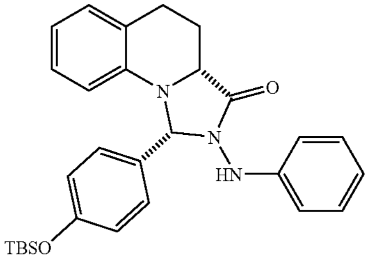
ZXD-132A
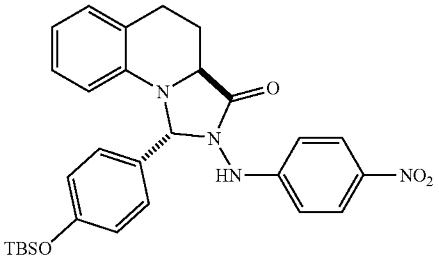
ZXD-133A
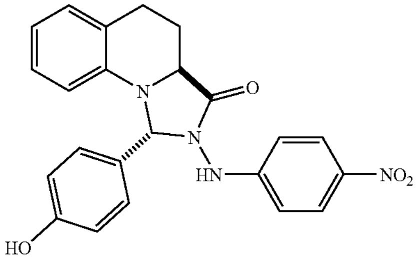
ZXD-140
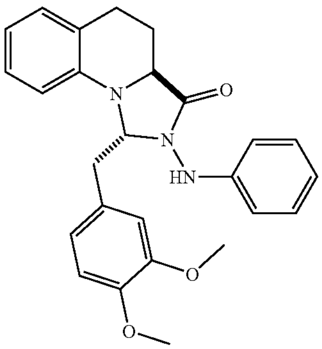

-continued
ZXD-142A
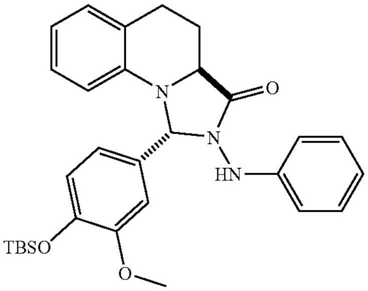
ZXD-147B
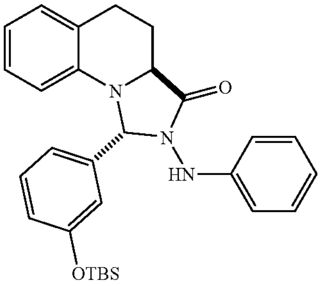
ZXD-156B
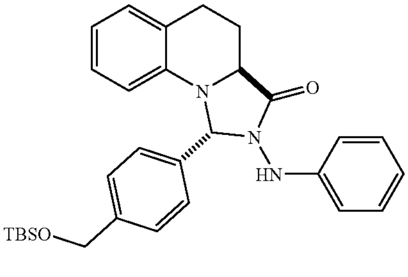
ZDL-11
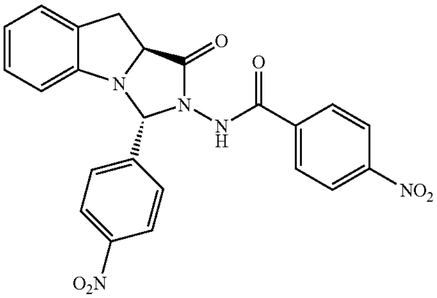
ZDL-19
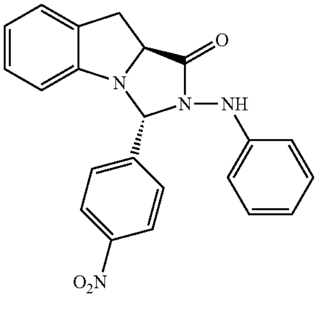
-continued
ZDL-21
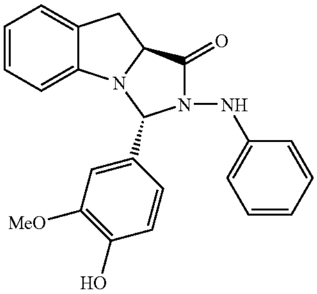
ZDL-38
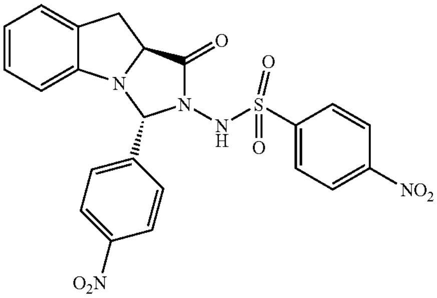
ZDL-39
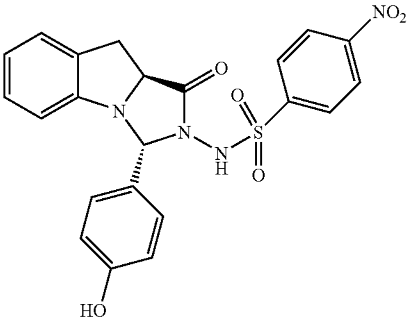
ZDL-41
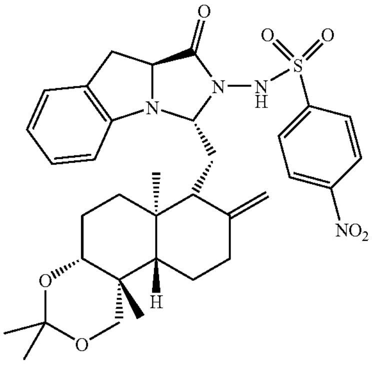

-continued
ZDL-42
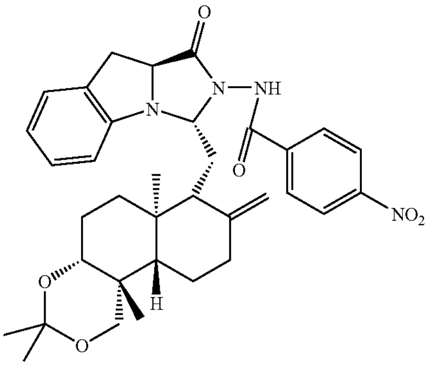
ZDL-43
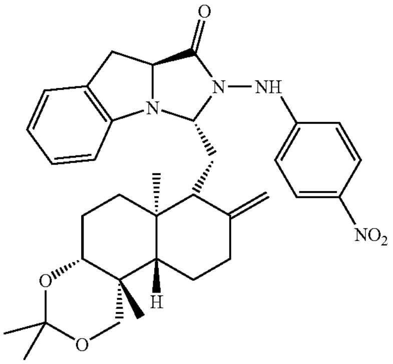
ZDL-69
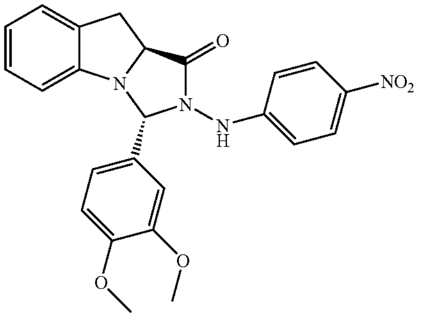
ZDL-93
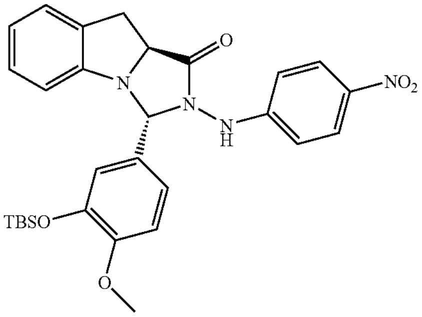
-continued
ZDL-94
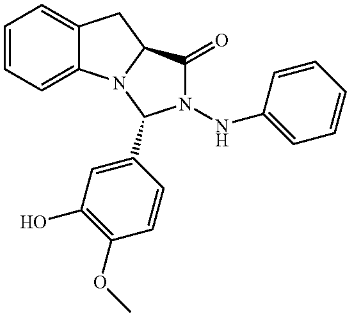
ZBJ-12A
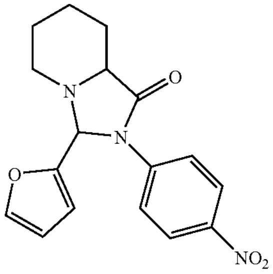
ZXP-10
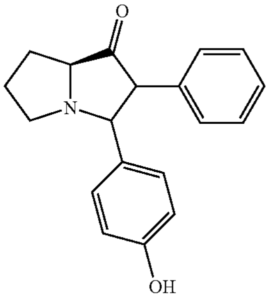
ZXP-12
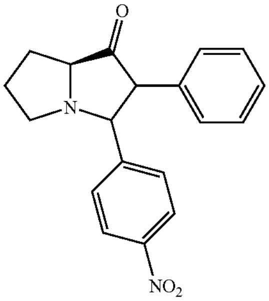
ZDL-60
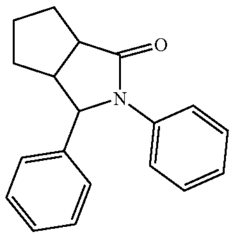

-continued
ZDL-61
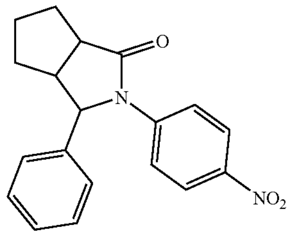
ZDL-62
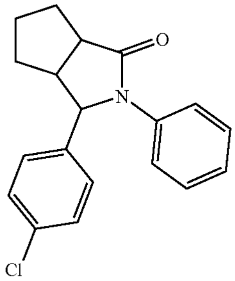
ZDL-63
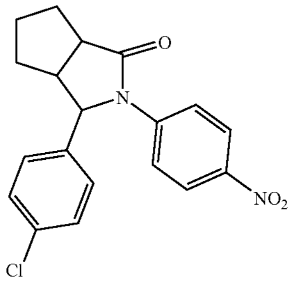
ZSD-7
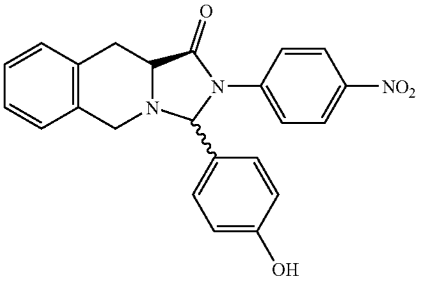
ZSD-8
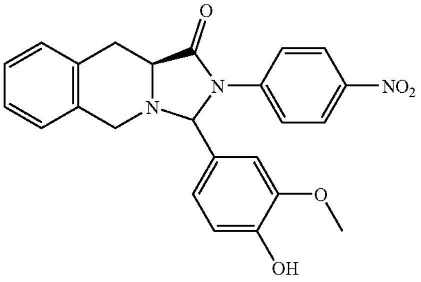
-continued
ZSD-9A
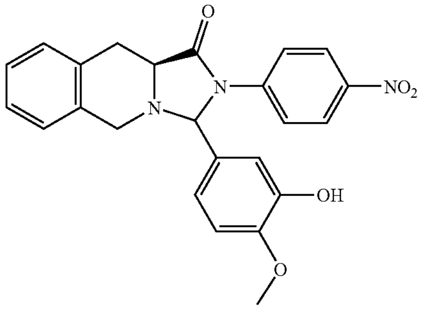
ZSD-11
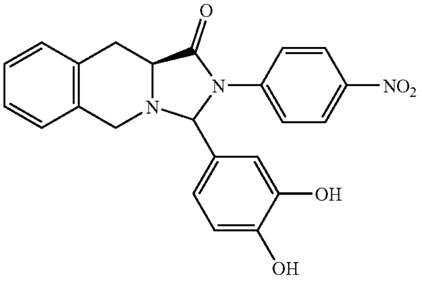
ZSD-12B
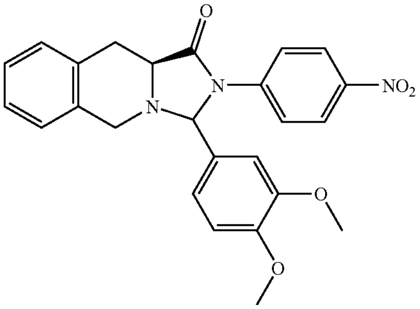
ZSD-18
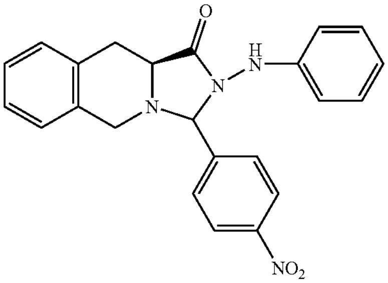
ZSD-20
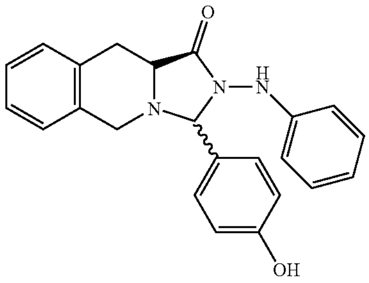

-continued
ZSD-27B
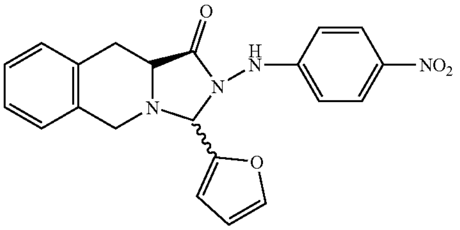
ZSD-28B
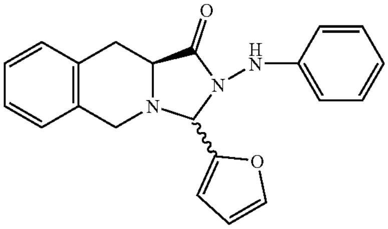
ZSD-30A
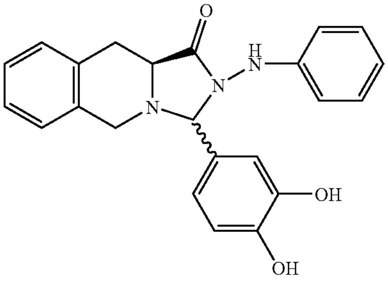
ZSD-32
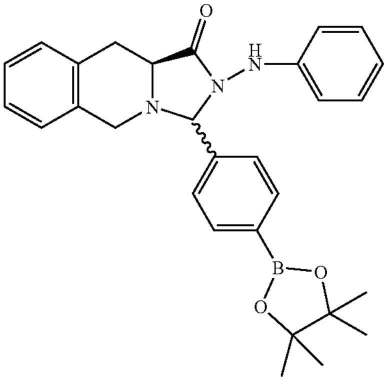
ZSD-36
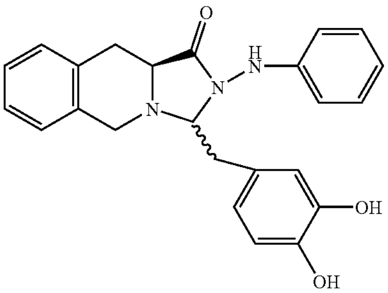
-continued
ZXD-100B
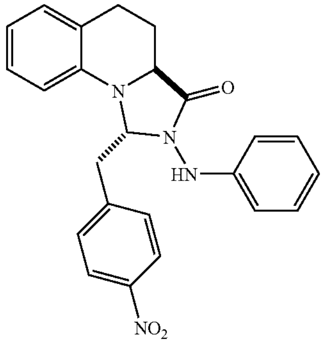
ZXD-106
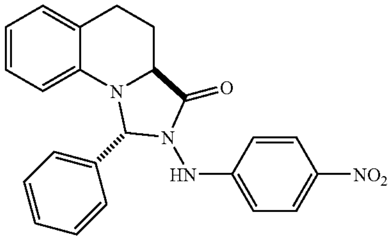
ZXD-107A
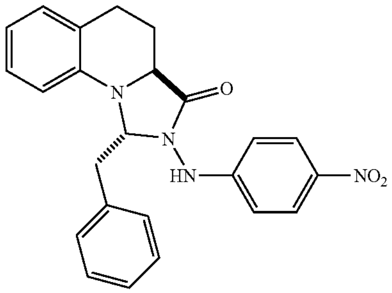
ZXD-109B
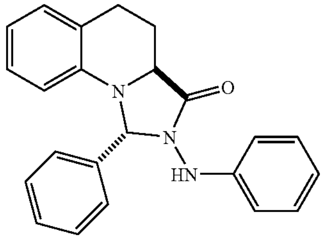
ZXD-120B
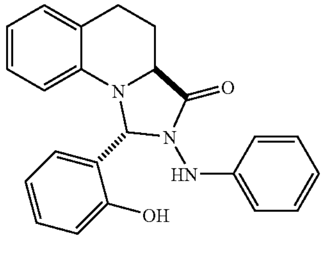

-continued
ZXD-121
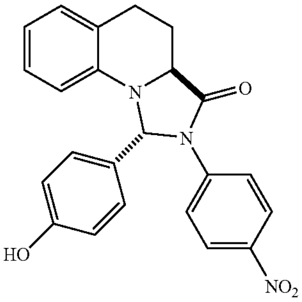
ZXD-126B
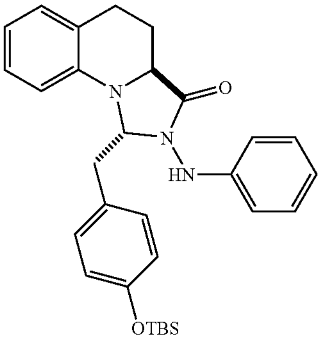
ZXD-127B
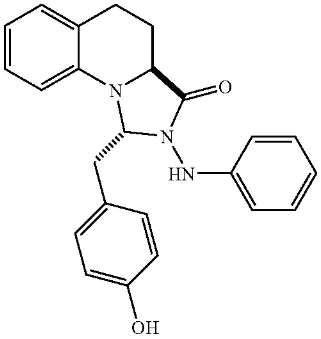
ZXD-70
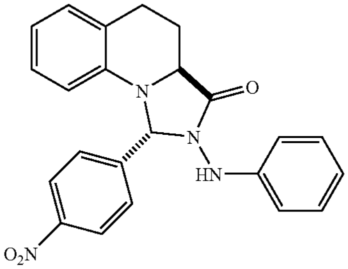
ZXD-78A
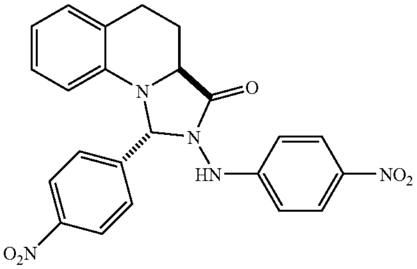
-continued
ZXD-86A
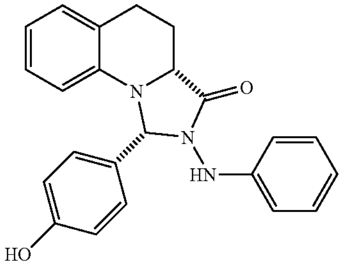
ZXD-86B
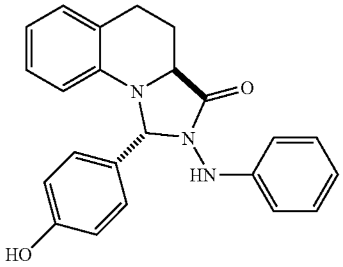
ZXD-87A
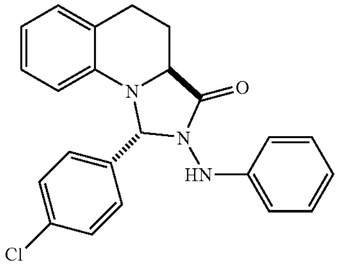
ZXD-89A
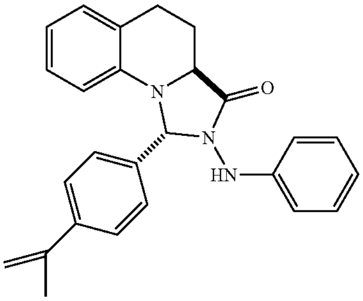
ZXD-95
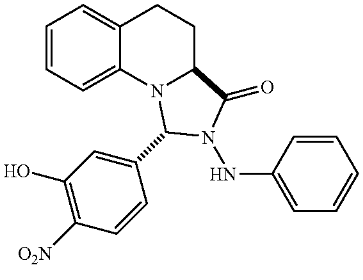

-continued
ZXD-100A
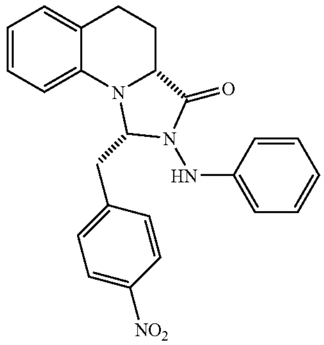
ZBM-19
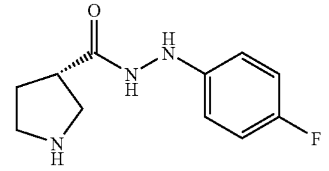
ZBM-21
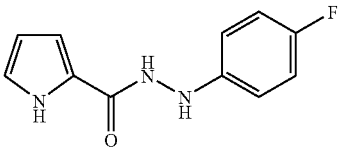
ZFD-42
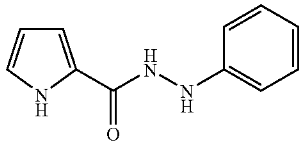
ZBM-28
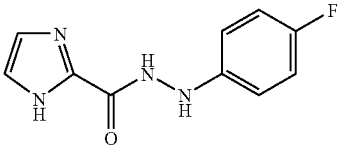
ZBM-29
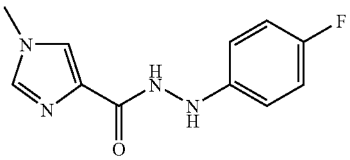
ZBM-30
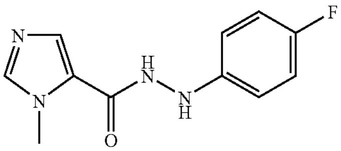
ZBM-35
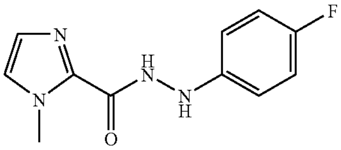
-continued
ZFD-44
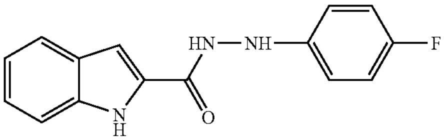
ZBM-36
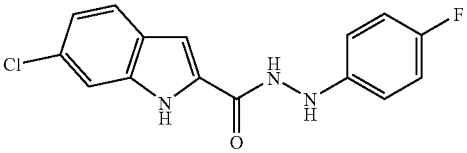
ZBM-24
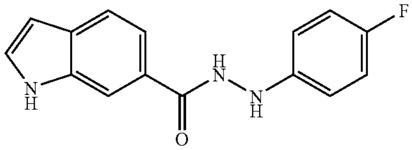
ZDL-101
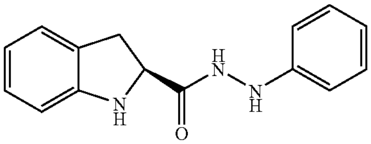
ZBM-5
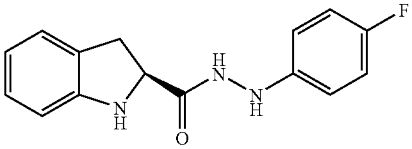
ZBM-6
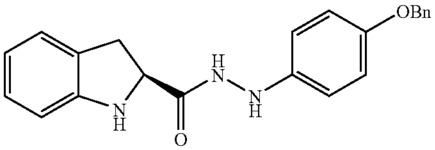
ZBM-8
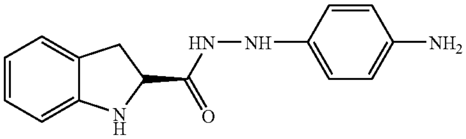
ZBM-20
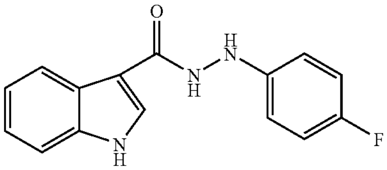
ZFD-38
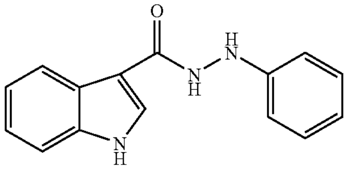

-continued
ZBM-11
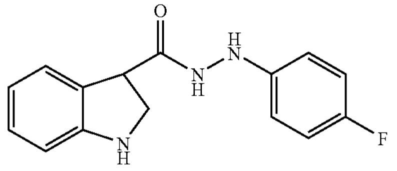
ZBM-15
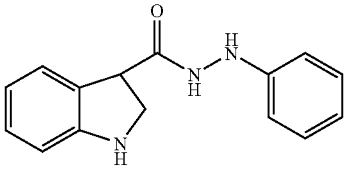
ZKD-2-1
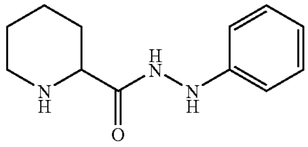
ZKD-17
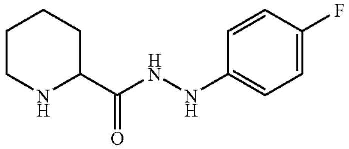
ZKD-21
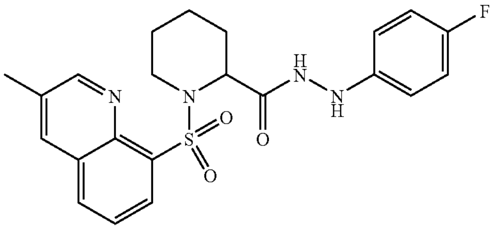
ZXD-F
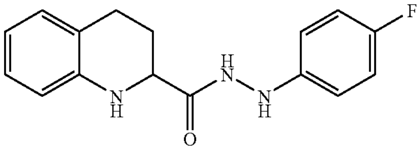
ZXD-44
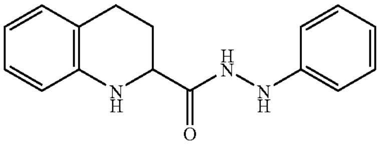
ZXD-45
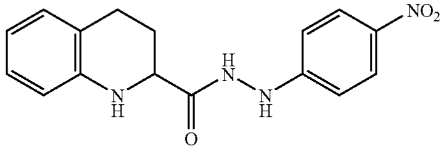
ZXD-51
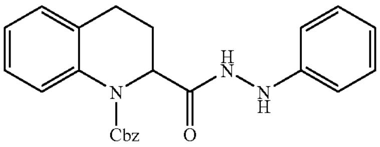
-continued
ZXD-53
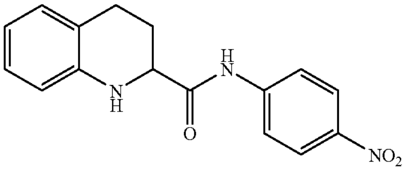
ZXD-62
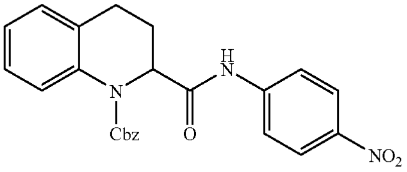
ZXD-72
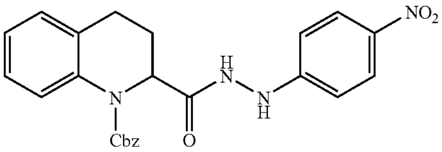
ZXD-102
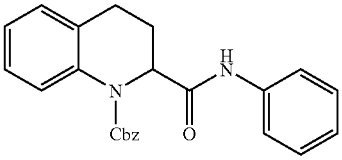
ZSD-15
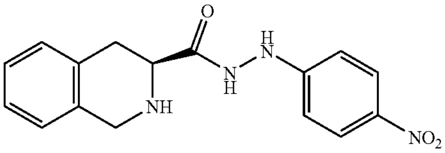
ZSD-16
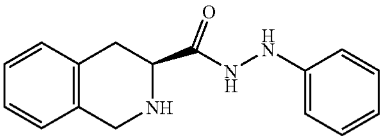
ZSD-54
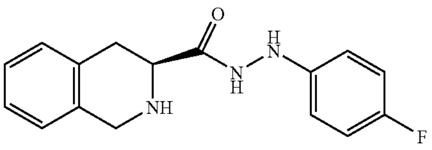
ZKD-4A
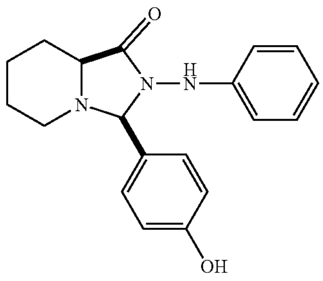

-continued
ZKD-4B
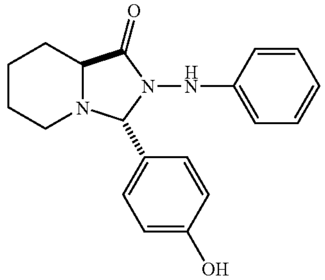
ZKD-5A
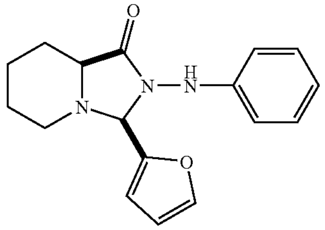
ZKD-5B
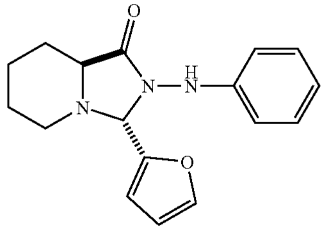
ZKD-6A
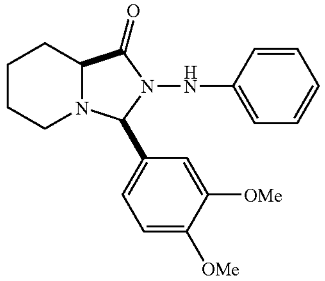
ZKD-6B
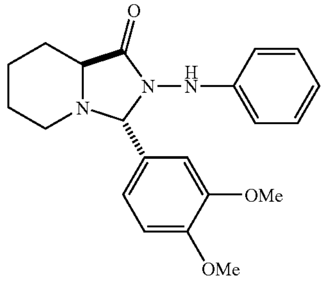
ZKD-7A
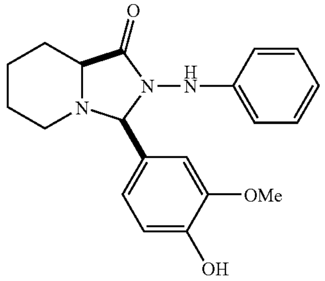
-continued
ZKD-7B
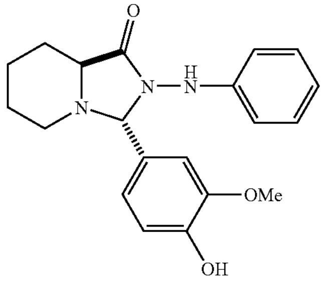
ZKD-8A
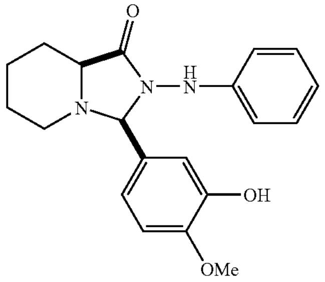
ZKD-8B
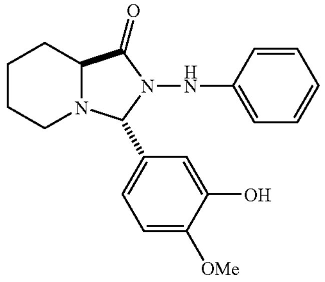
ZKD-8B
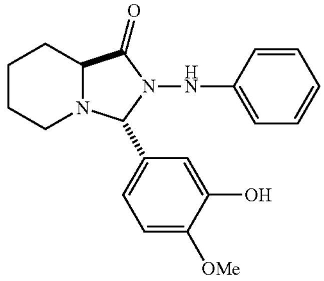
ZKD-10A
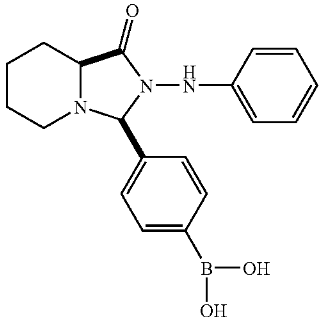

-continued
ZKD-10B
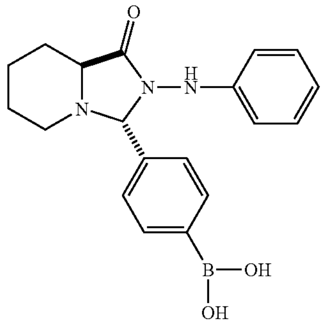
ZKD-12A
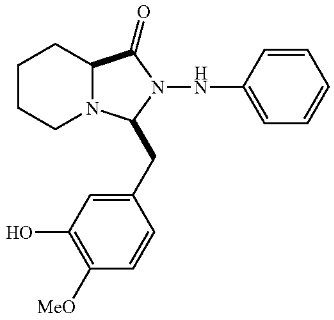
ZKD-12B
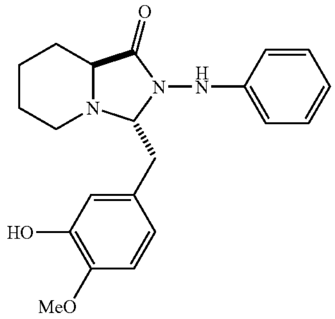
ZKD-13A
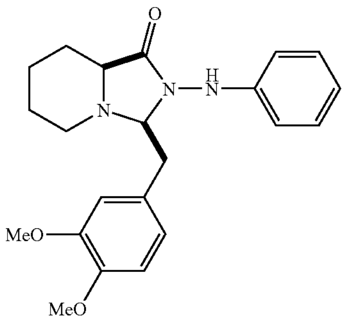
ZKD-13B
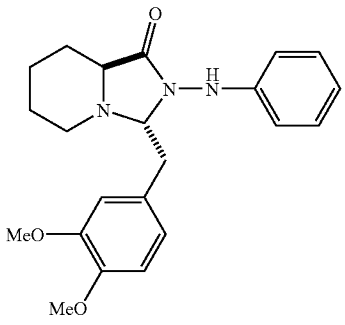
-continued
ZKD-14A
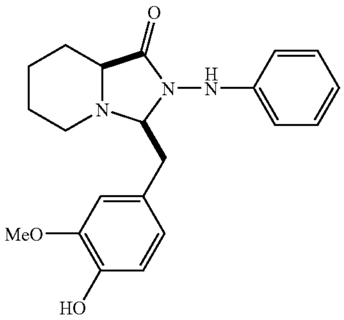
ZKD-14B
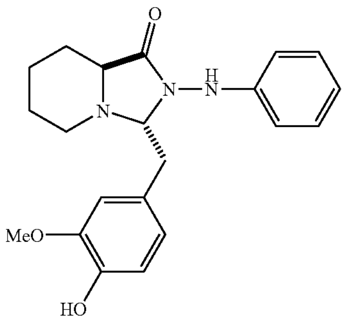
ZKD-15A
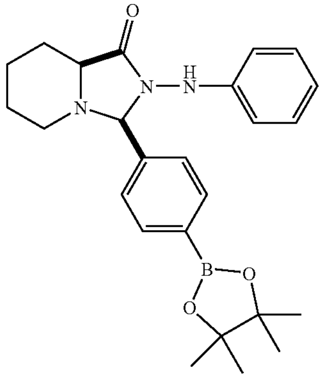
ZKD-15B
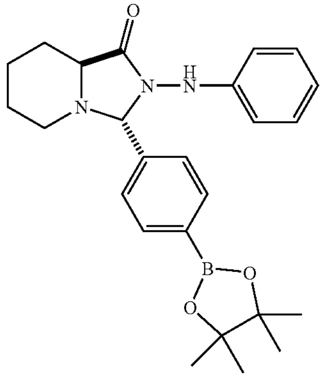

-continued

ZKD-18A

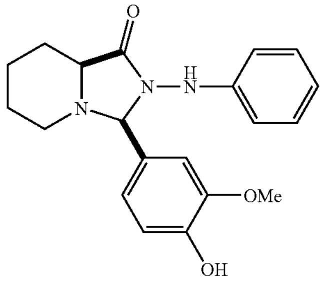

ZKD-18B

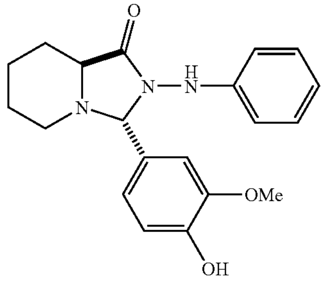

ZKD-19A

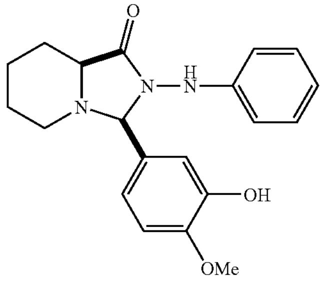

ZKD-19B

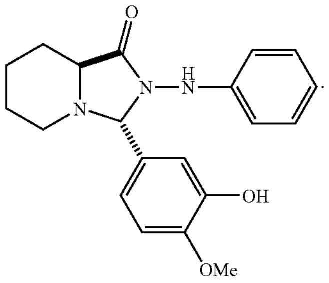

The second aim of the present invention is to provide a use of the above-mentioned compounds in pharmacy. The application of the compound, its isomers and/or its salts in the preparation of drugs for the treatment or prevention of diseases is: said diseases include one or more of the following: diseases related to the reproduction, replication or infection of one or more of Zika virus, dengue virus, flavivirus, West Nile virus and Chikungunya virus, hepatitis C, Japanese encephalitis, forest encephalitis, or AIDS caused by HIV.

The third aim of the present invention is to provide an application of said compounds, isomers or salts thereof in the preparation of a medicine for the treatment or prevention of diseases, characterized in that the diseases are the diseases caused by bacteria.

Preferably, the application of said compounds, isomers or salts thereof in the preparation of a medicine for the treatment or prevention of diseases is characterized in that: the diseases include the diseases caused by *Acinetobacter baumannii.*

The fourth aim of the present invention is to provide a pharmaceutical composition which is composed of the compounds, isomers or its pharmaceutically acceptable salts as the main active ingredients, supplemented by a pharmaceutically acceptable carrier.

The present invention has the following advantages: the present invention finds that the compounds shown in formula (I) better inhibits Zika virus and dengue virus infection and replication, may be used as a drug for treating and preventing diseases caused by Zika virus and dengue virus, and may also become a drug for treating and preventing diseases caused by other flaviviruses, such as yellow fever, West Nile virus infection, Japanese encephalitis caused by Japanese encephalitis infection, Chikungunya virus infection, hepatitis C, forest encephalitis and AIDS caused by HIV etc., and diseases caused by hand, foot and mouth virus infection etc. The compounds may treat disease caused by bacterial infections, including inflammatory bowel disease ulcerative colitis and Crohn's disease, diseases caused by *Escherichia coli*, diseases caused by *Staphylococcus aureus* etc., and diseases caused by *Acinetobacter baumannii.*

DETAILED DESCRIPTION

To make the above-mentioned objectives, features and advantages more easily be understood, the specific embodiments of the present invention will be described in detail below. Although the following descriptions illustrate in detail in order to facilitate understanding of the present invention, it should be understood by a skilled person in the art that the present invention can also be enabled by other ways not described herein. The skilled person in the art can also implement the present invention without departing from the spirit of the present invention such that the following descriptions concerning the examples will not limit the present invention. In addition, the expressions "an embodiment" or "an example" used herein refers to including specific features, structure and characteristics of at least one embodiment of the present invention. "According to an embodiment of the present invention" appears in the present disclosure does not necessarily mean that it refers to the same embodiment, or it does not necessarily mean that it independently or selectively contradicts with one another. It should be noted that the following embodiments are only used to illustrate the technical solutions of the present invention and not to limit them. Although the present invention has been described in detail with reference to the preferred embodiments, those of ordinary skill in the art should understand that the technical solutions of the present invention can be modified or equivalently replaced without departing from the spirit and scope of the technical solutions of the present invention, and all of them shall be covered by the scope of the claims of the present invention.

EXAMPLE 1: a method for preparing the compounds of the present invention, including:

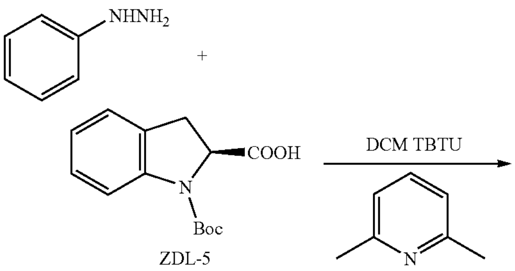

ZDL-5

-continued

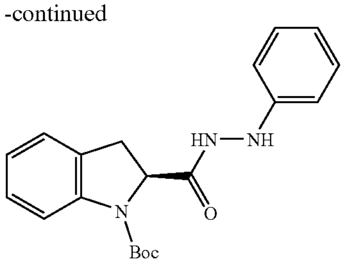

ZDL-17

2.74 ml of phenylhydrazine and 7.0 g of ZDL-5 were dissolved in 500 ml of DCM, and 5.3 ml of 2,6-lutidine was added, and finally 12.3 g of TBTU was added, and the mixture was stirred overnight at room temperature. The mixture was then purified to obtain about 7 g of ZDL-17.

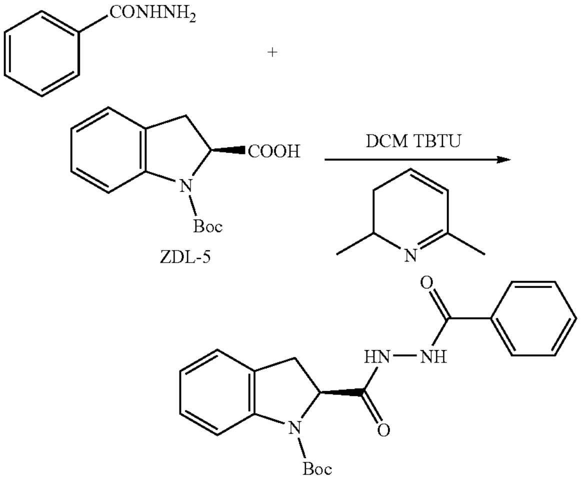

ZDL-5

ZDL-27

600 mg of benzohydrazide and 1.39 g of ZDL-5 were dissolved in 100 ml of DCM, and 0.77 ml of 2,6-lutidine was added, and finally 2.12 g of TBTU was added, and the mixture was stirred overnight at room temperature. The mixture was then purified to obtain approximately 1.6 g of ZDL-27.

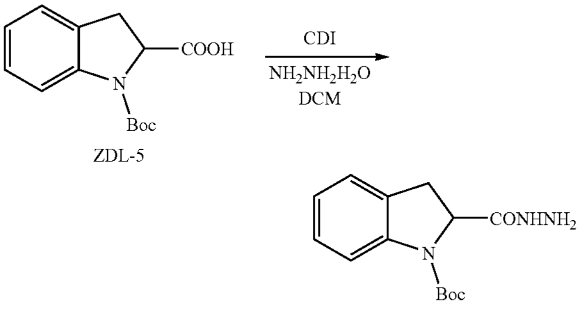

ZDL-5

ZDL-26

ZDL-5 (500 mg) was dissolved in 50 ml DCM, and CDI (323 mg) was added under ice bath. The mixture was stirred for 20 minutes, and then hydrazine hydrate (0.55 ml) was added dropwise and stirred under ice bath for 2 hours.

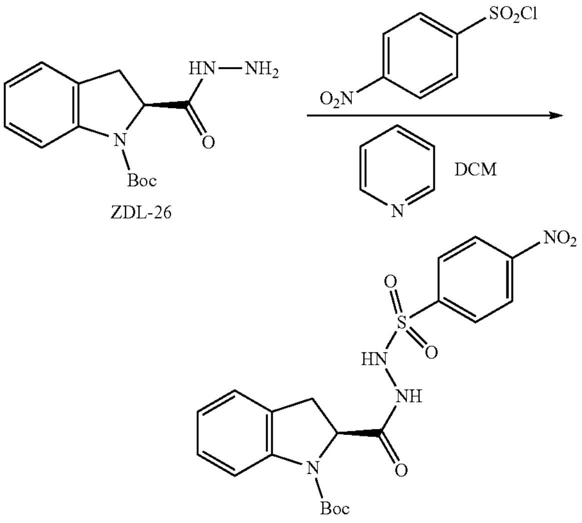

ZDL-26

ZDL-29

850 mg of ZDL-26 was dissolved in 100 ml DCM, and 0.74 ml of pyridine was added under ice bath, and finally 815 mg of p-nitrobenzenesulfonyl chloride was added and the mixture was stirred at room temperature for 6 hours to obtain approximately 1.2 g of ZDL-29. After that, 250 mg of ZDL-29 was dissolved in 8 ml DCM, and 2 ml of TFA was added and the mixture was stirred at room temperature for 2 hours. After evaporating the reaction system by vacuum drying for 6 hours, 10 ml of toluene, 82 mg of p-nitrobenzaldehyde and 0.22 ml of triethylamine were added, and the mixture was reacted at 110° C. for 2 hours. The mixture then purified to obtain 90 mg of ZDL-38. After that, 150 mg of ZDL-29 was dissolved in 4 ml of DCM, and 1 ml of TFA was added and the mixture was stirred at room temperature for 2 hours. After evaporating the reaction system by vacuum drying for 6 hours, 10 ml of toluene, 95 mg of ZAL-2 and 0.16 ml of triethylamine were added, and the mixture was reacted at 110° C. for 2 hours. The mixture then purified to obtain 110 mg of ZDL-41.

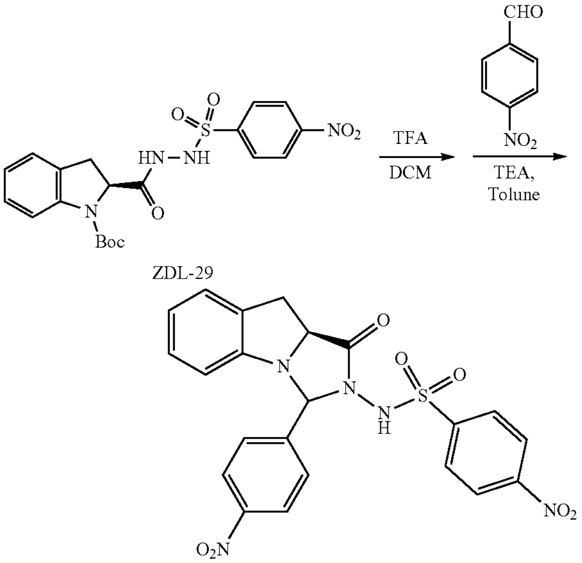

ZDL-29

ZDL-38

-continued

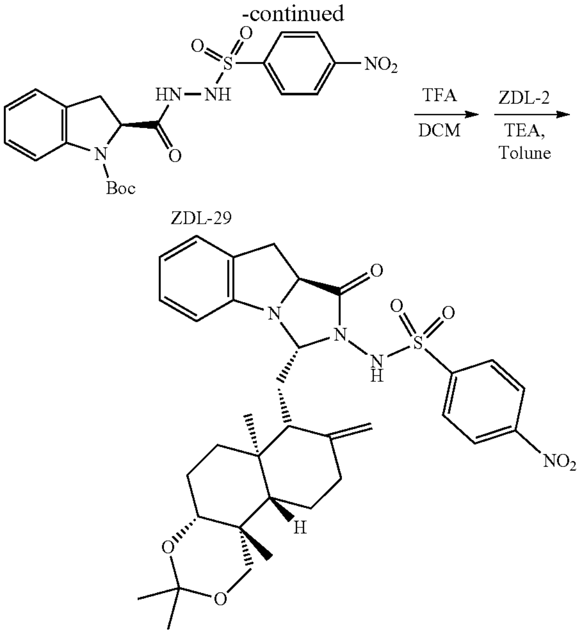

ZDL-29

ZDL-41

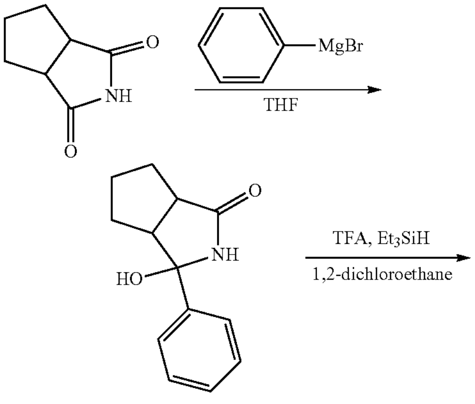

ZDL-52

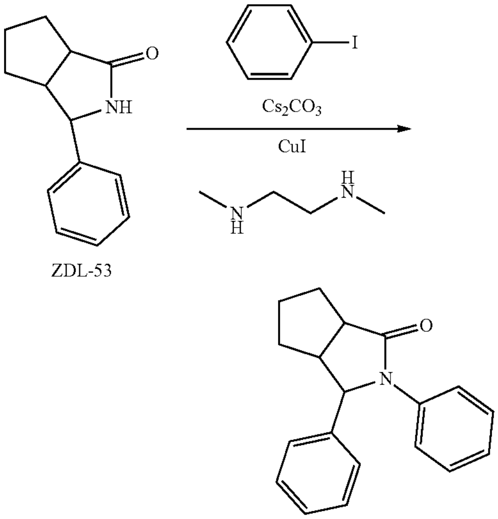

ZDL-53

ZDL-60

1.0 g of 1,2-cyclopentadicarboximide was dissolved in 50 ml of anhydrous THF under nitrogen protection, and 6.0 ml of phenylmagnesium bromide dropwise was then carefully added after fully cooling in an ice bath, and finally the mixture was stirred at room temperature for 3 hours. The mixture then purified to obtain 560 mg of crude ZDL-52. After that, 560 mg of ZDL-52 was dissolved in 40 ml of 1,2-dichloroethane, and 0.6 ml of TFA and 1.2 ml of triethylsilane were added and the mixture was reacted at 50° C. for 1 hour. The mixture then purified to obtain 400 mg of ZDL-53. After that, 100 mg of ZDL-53, 19 mg of copper (I) iodide and 323 mg of cesium carbonate into to a round-bottom flask. After being protected by $N_2$, 20 ml of 1,4-dioxane, 80 μl of iodobenzene and 20 μl of N,N'-dimethylethylenediamine were added into the round-bottom flask in order. The mixture was reacted at 100° C. for 8 hours. The mixture then purified to obtain ZDL-60.

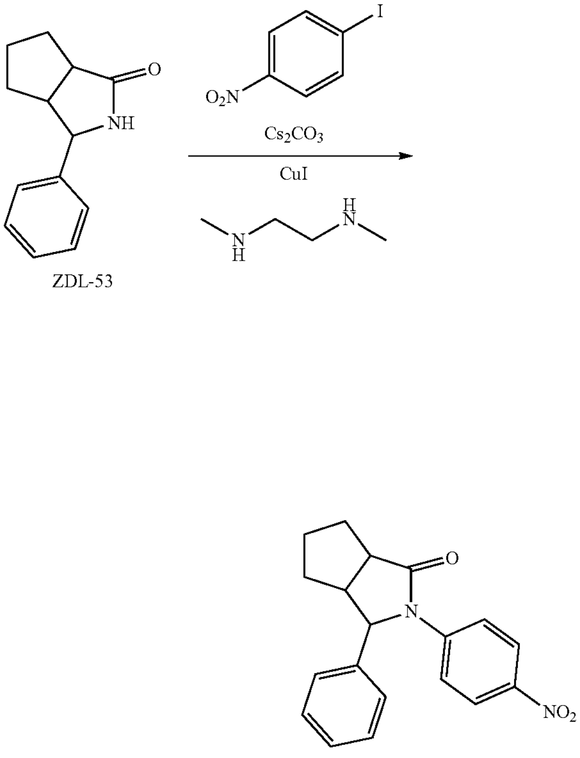

ZDL-53

ZDL-61

200 mg ZDL-53, 38 mg of copper (I) iodide and 647 mg of cesium carbonate into to a round-bottom flask. After being protected by $N_2$, 20 ml of 1,4-dioxane, 371 mg of 4-nitroiodobenzene and 40 μl of N,N'-dimethylethylenediamine were added into the round-bottom flask in order. The mixture was reacted at 100° C. for 8 hours. The mixture then purified to obtain 120 mg of ZDL-61.

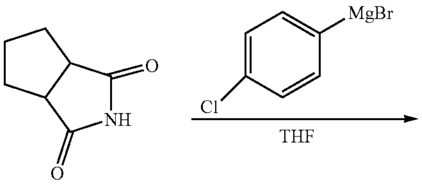

-continued

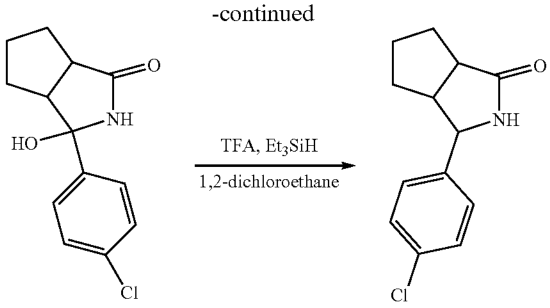

ZDL-58 ZDL-59

1.0 g of 1,2-cyclopentadicarboximide was dissolved in 50 ml of anhydrous THF under nitrogen protection, and 6.0 ml of 4-chlorophenylmagnesium bromide dropwise was then carefully added after fully cooling in an ice bath, and finally the mixture was stirred at room temperature for 3 hours. The mixture then purified to obtain 1 g of crude ZDL-58.

1.0 g of ZDL-58 was dissolved in 40 ml of 1,2-dichloroethane, and 0.9 ml of TFA and 1.9 ml of triethylsilane were added and the mixture was reacted at 50° C. for 1 hour. The mixture then purified to obtain 500 mg of ZDL-59.

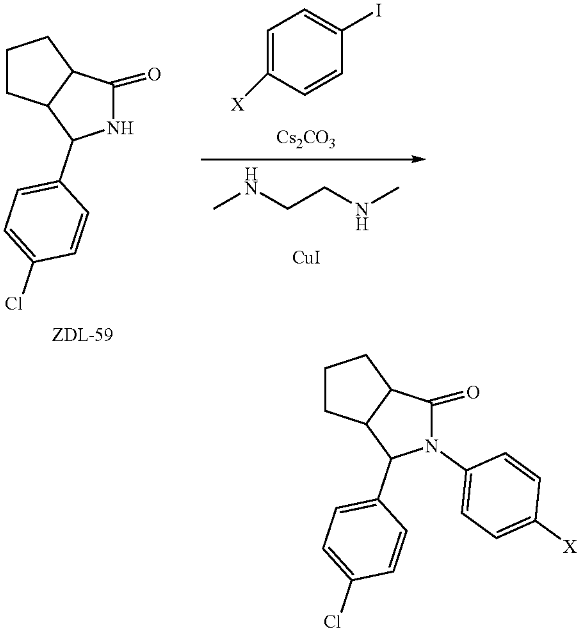

ZDL-59

X = H, ZDL-62
X = $NO_2$, ZDL-63

200 mg ZDL-59, 32 mg of copper (I) iodide and 552 mg of cesium carbonate into to a round-bottom flask. After being protected by $N_2$, 20 ml of 1,4-dioxane, 140 μl of iodobenzene and 40 μl of N,N'-dimethylethylenediamine were added into the round-bottom flask in order. The mixture was reacted at 100° C. for 8 hours. The mixture then purified to obtain 95 mg of ZDL-62.

200 mg ZDL-59, 32 mg of copper (I) iodide and 552 mg of cesium carbonate into to a round-bottom flask. After being protected by $N_2$, 20 ml of 1,4-dioxane, 316 mg of p-Nitroiodobenzene and 40 μl of N,N'-dimethylethylenediamine were added into the round-bottom flask in order. The mixture was reacted at 100° C. for 8 hours. The mixture then purified to obtain 70 mg of ZDL-63.

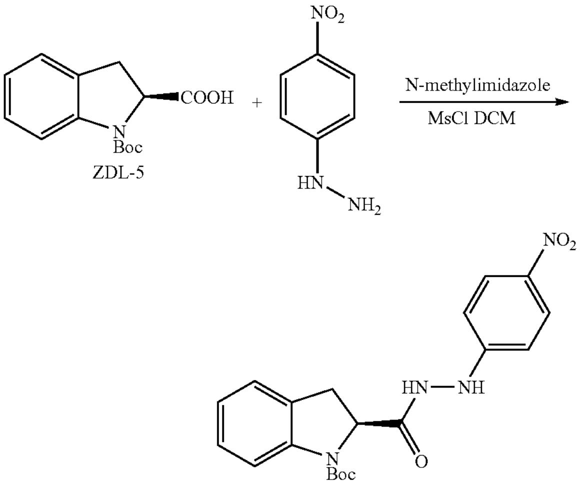

ZDL-5

ZDL-18

7.0 g of ZDL-5 was dissolved in 400 ml DCM, and 5.3 ml of N-methylimidazole was added under ice bath, and 2.06 ml of MsCl was added after stirring for 5 minutes, and then 3.66 g of p-nitrophenylhydrazine was added after stirring for another 30 minutes, and then the mixture was stirred overnight at room temperature. The mixture was then purified to obtain 6.5 g of ZDL-18.

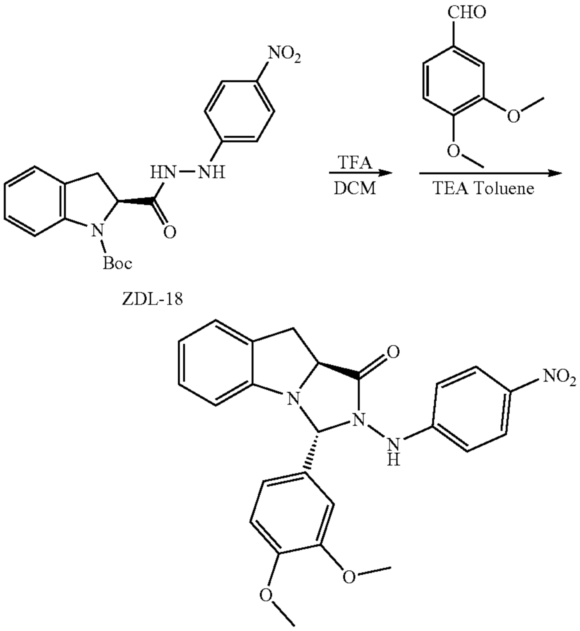

ZDL-18

ZDL-89

300 mg of ZDL-18 was dissolved in 8 ml DCM, and 2 ml of TFA was added and the mixture was stirred at room temperature for 2 hours. After evaporating the reaction system by vacuum drying for 6 hours, 10 ml of toluene, 60 μl of 3,4-dimethoxybenzaldehyde and 0.32 ml, of triethylamine were added, and the mixture was reacted at 110° C. for 2 hours. The mixture then purified to obtain 90 mg of ZDL-89.

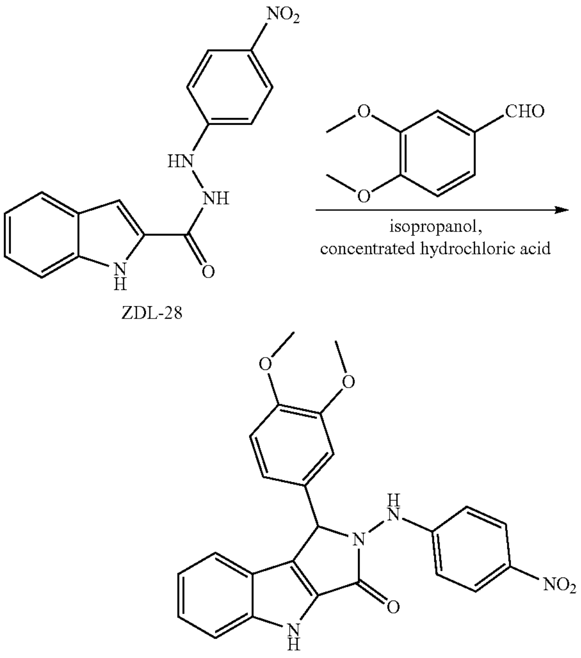

ZDL-28

ZFD-33, (main product)

200 mg of ZDL-28 was suspended in 10 ml of isopropanol, and then 123 mg of veratraldehyde and 2 drops of concentrated hydrochloric acid were added in order. The volatile components are removed after 8 hours of reaction at 85° C. The residue was chromatographed on a silica gel column with a DCM: EA system and passed through the column to obtain 150 mg of ZFD-33A.

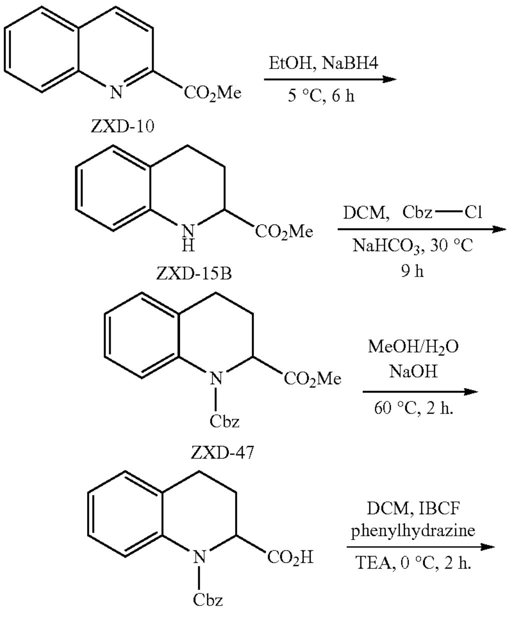

ZXD-10

ZXD-15B

ZXD-47

ZXD-60

-continued

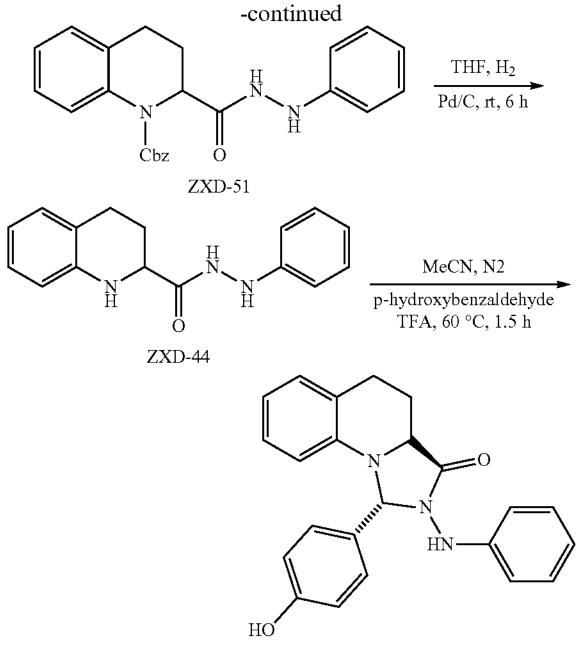

ZXD-51

ZXD-44

ZXD-86B 12.5 g of ZXD-10 was dissolved in 100 mL of ethanol and stirred at 5° C.□ followed by adding 0.125 eq, 0.125 eq, 0.25 eq, 0.5 eq and 0.25 eq in five batches, totaling 1.25 eq of sodium borohydride. The reaction was stopped after a total of 6 hours. After that, 200 mL of water was added into the solution, and the pH was adjusted to weakly alkaline with solid carbonate. The solution was then extracted with DCM for several times, the organic phases were combined and dried over anhydrous sodium sulfate. 12.5 g of ZXD-15B product was obtained by column chromatography, which was a colorless liquid, and the yield was 48.0%. Finally, the unreacted ZXD-10 is recovered.

16.2 g of ZXD-15B was dissolved in 250 mL of DCM, 21.4 g of solid sodium bicarbonate (3 equiv) was added, and 17.9 mL of Cbz-Cl (1.5 equiv) was added dropwise, after which the reaction was transferred to 30° C. for 9 hours and then stopped. After the solvent was evaporated, the crude product was diluted with ethyl acetate, then washed with $NaHCO_3$ solution and dried. 25.6 g of ZXD-47 product was obtained by column chromatography, which was a colorless liquid, and the yield was 92.9□.

6 g of ZXD-47 was dissolved in a mixed solvent of methanol and water (36 mL: 24 mL), 960 mg (1.3 equiv) of solid sodium hydroxide was added, and the temperature was raised to 60° C. for reflux reaction. After 2 hours of reaction, it shows that the raw materials have reacted completely. Water was added into the solution after evaporating the methanol, and the pH of the system was adjusted to 1-2 with 1N HCl, and then concentrated to obtain 5.65 g of ZXD-60 foamed solid with a yield of 98.4%.

ZXD-60 was dissolved in DCM and cooled at 0° C., and triethylamine (1.5 equiv) was added and stirred at the same temperature for 5 minutes. After that, isobutyl chloroformate (IBCF, 1.1 equiv) was added and stirred continuously at the same temperature for 1 hour. After the mixture is converted into active ester intermediates, phenylhydrazine (aniline or benzylamine) was added, and after stirring at 0° C. for 4 hours, it showed that all the intermediate conversion had stopped. The intermediates were diluted with DCM, and washed with saturated $NaHCO_3$ solution and brine, and then dried over anhydrous sodium sulfate. After concentration, a mixed solvent of petroleum ether and ethyl acetate was used to stir and precipitate the product ZXD-51, which was a white solid with a yield of 93.9%.

ZXD-51 was dissolved in THF, and 100 palladium on carbon (0.05 equiv) was added. After vacuuming, a hydrogen balloon was inserted, and the reaction was carried out at 25° C. and stopped after 6 hours. After that, diatomaceous earth was used for suction filtration to remove palladium on carbon. After the mother liquor was evaporated, the product ZXD-44 was obtained by column chromatography, which was a white solid with a yield of 99.0%.

250 mg of ZXD-44 and aldehyde (1.1 equiv) were dissolved in 10 mL of acetonitrile. TFA (1.0 equiv) was added under nitrogen protection, and the reaction was transferred to an oil bath preheated to 60° C. and refluxed. After 1.5 hours reaction, a product was formed on the spot plate, and the reaction of raw materials was basically completed and stopped. After the product was cooled to room temperature, saturated sodium bicarbonate solution was added to quench the reaction. The product was then diluted with ethyl acetate, then washed with $NaHCO_3$ solution and brine and dried over anhydrous sodium sulfate. After concentration, ZXD-86B is separated by column chromatography, which was a white solid with a yield of 95.0%.

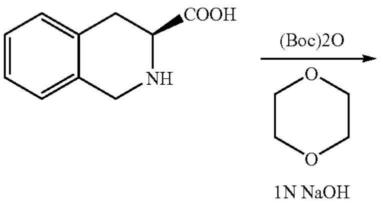

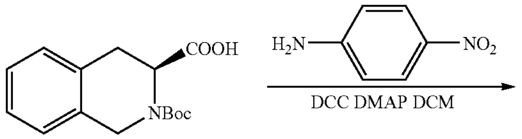

ZSD-2

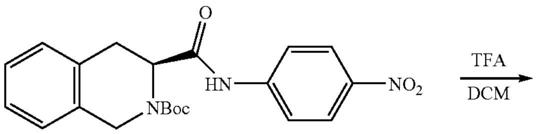

ZSD-4

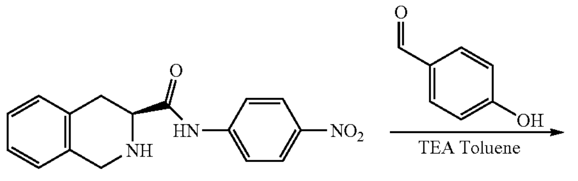

ZSD-5

-continued

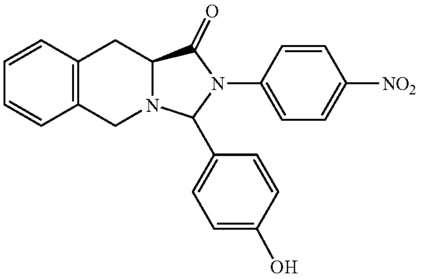
ZSD-7

6 g of tetrahydroisoquinoline-3-carboxylic acid was dissolved in 50 ml of 1N NaOH□ 50 ml of 1,4-dioxane was added□ and 9 ml of (Boc) 20 was added dropwise under an ice bath□ and reacted at room temperature for 4 hours. After the reaction is completed, dioxane is removed by distillation under reduced pressure, the system is adjusted to acidity with citric acid, and then extracted with EA, washed with saturated NaCl solution, and dried with anhydrous sodium sulfate. After the organic phase is evaporated to dryness, 7.8 g of transparent oily ZSD-2 can be obtained without purification.

3.1 g of ZSD-2 was dissolved in 50 ml of DCM, and 1.4 g of p-nitroaniline and 124 mg of DMAP were added in an ice bath, then 2.1 g of DCC was added in batches and left at room temperature overnight. After the completion of the reaction, suction filtration was performed and the mother liquor was concentrated and then extracted with EA, washed with saturated NaCl solution, and dried with anhydrous sodium sulfate. Finally, recrystallization was performed to obtain 3.5 g of ZSD-4 product.

250 mg of ZSD-4 was dissolved in 3 ml of DCM, 1 ml of trifluoroacetic acid was added and stirred at room temperature. The reaction was complete after stirring for 30 minutes. After that, the solvent was evaporated to dryness to obtain ZSD-5. ZSD-5 was dissolved in toluene, 0.3 ml of triethylamine and 113 mg of p-hydroxybenzaldehyde were added in order, and then refluxed at 110° C. for 1 hour. The mixture was extracted with EA, washed with saturated $NaHCO_3$ and NaCl solutions, and dried with anhydrous sodium sulfate. After the completion of the drying, the solvent was concentrated and further separated and purified by column chromatography to obtain 150 mg of the target product of ZSD-7.

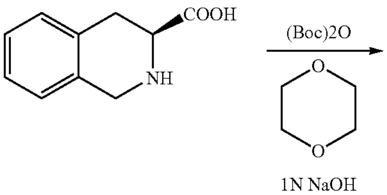

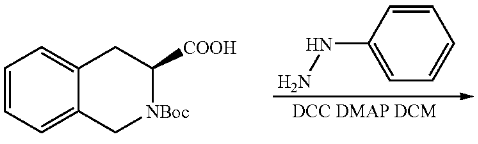

ZSD-2

-continued

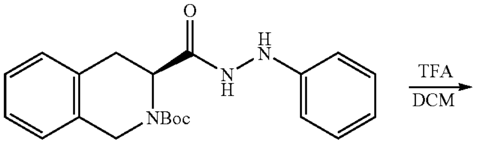

ZSD-14

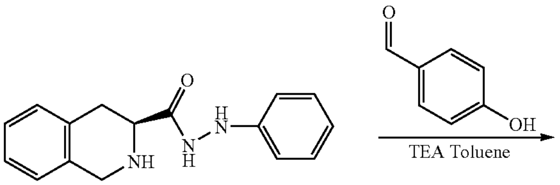

ZSD-16

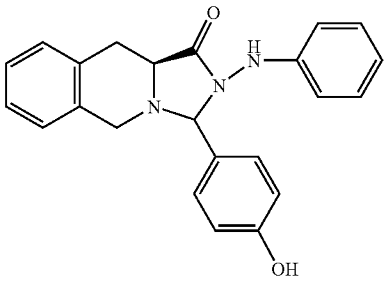

ZSD-20

5 g of ZSD-2 was dissolved in 50 ml of DCM, and 1.77 ml of phenylhydrazine and 220 mg of DMAP were added in an ice bath, then 3.72 g of DCC was added in batches and left at room temperature overnight. After the completion of the reaction, suction filtration was performed and the mother liquor was concentrated and then extracted with EA, washed with saturated NaCl solution, and dried with anhydrous sodium sulfate. Finally, recrystallization was performed to obtain 5.7 g of ZSD-14 product. 250 mg of ZSD-14 was dissolved in 3 ml of DCM, 1 ml of trifluoroacetic acid was added and the reaction was complete after stirring at room temperature for 30 minutes. After the reaction, the solvent was evaporated to dryness to obtain ZSD-16 for later use. ZSD-16 was dissolved in toluene, 0.3 ml of triethylamine and 104 mg of p-hydroxybenzaldehyde were added in order, and then refluxed at 110° C. for 1 hour. The mixture was extracted with EA, washed with saturated $NaHCO_3$ and NaCl solutions, and dried with anhydrous sodium sulfate. After the completion of the drying, the solvent was concentrated and further separated and purified by column chromatography to obtain 161 mg of the target product of ZSD-20.

The antibacterial ability of each specific compound ($EC_{50}$ refers to the antiviral infection activity of the compound, among which Dengue virus: DENV; Zika virus: ZIKV; Usutu virus: USUV (usutu virus, which is a flavivirus that similar to Zika virus); AB: *Acinetobacter baumannii*) prepared by the above method is shown in the table below.

TABLE 1 anti-Zika virus and anti-Usutu virus activity (inhibition rate)

| Serial number | Compound number | Drug concentration (μM) Anti-USUV 33 | Anti-USUV 11 | Anti-ZIKV 33 | Anti-ZIKV 11 |
|---|---|---|---|---|---|
| 1 | ZXP-10 | + | – | | |
| 2 | ZXP-12 | + | – | | |
| 3 | ZDL-11 | + | – | – | – |
| 4 | ZDL-19 | +++ | – | + | – |
| 5 | ZDL-21 | – | – | + | – |
| 6 | ZDL-38 | + | – | – | – |
| 7 | ZDL-39 | – | – | + | – |
| 8 | ZDL-41 | / | +++ | / | +++ |
| 9 | ZDL-42 | / | +++ | / | +++ |
| 10 | ZDL-43 | +++ | +++ | +++ | +++ |
| 11 | ZDL-60 | + | – | + | – |
| 12 | ZDL-61 | +++ | – | + | – |
| 13 | ZDL-62 | +++ | – | + | – |
| 14 | ZSD-7 | +++ | – | +++ | – |
| 15 | ZSD-8 | – | – | +++ | + |
| 16 | ZSD-9A | + | – | +++ | + |
| 17 | ZSD-11 | + | – | +++ | – |
| 18 | ZSD-12B | + | – | – | – |
| 19 | ZSD-18 | + | – | + | – |
| 20 | ZSD-20 | + | – | +++ | – |
| 21 | ZSD-27B | + | – | – | – |
| 22 | ZSD-30A | +++ | – | – | – |
| 23 | ZSD-32 | + | – | – | – |
| 24 | ZSD-36 | + | – | – | – |
| 25 | ZXD-51 | – | – | + | – |
| 26 | ZXD-53 | – | – | + | – |
| 27 | ZXD-62 | + | – | +++ | – |
| 28 | ZXD-72 | – | – | + | – |
| 29 | ZXD-86A | – | – | +++ | – |
| 30 | ZXD-86B | +++ | +++ | +++ | + |
| 31 | ZXD-95 | + | – | / | + |
| 32 | ZXD-102 | – | – | / | + |
| 33 | ZXD-107A | – | – | / | +++ |
| 34 | ZXD-121 | – | – | / | +++ |
| 35 | ZXD-126B | +++ | +++ | / | +++ |
| 36 | ZXD-131A | / | +++ | / | + |
| 37 | ZXD-131B | / | + | – | – |
| 38 | ZXD-140 | +++ | – | / | + |
| 39 | ZXD-147B | / | +++ | / | +++ |
| 40 | ZXD-156B | / | +++ | / | +++ |
| 41 | ZXD-157B | / | +++ | | |
| 42 | ZXD-176 | +++ | +++ | / | +++ |
| 43 | ZXD-178A | / | + | / | +++ |
| 44 | ZXD-178B | / | + | / | +++ |
| 45 | ZXD-181A | + | – | +++ | +++ |
| 46 | ZXD-241B | +++ | – | +++ | – |

+++: Complete suppression;
+: Partial suppression;
–: Inactive;
/: Untested

TABLE 2 anti-Zika virus activity ($EC_{50}$)

| Serial number | Compound number | $EC_{50}$ (μM) |
|---|---|---|
| 1 | ZXD-142A | 1.56 ± 0.21 |
| 2 | ZXD-167 | 7.40 ± 0.37 |
| 3 | ZXD-87A | 3.40 ± 0.38 |
| 4 | ZFD-33A + B | 17.21 |

TABLE 3

| anti- dengue virus activity ($EC_{50}$, μM) | | |
|---|---|---|
| Serial number | Compound number | $EC_{50}$ |
| 1 | ZBJ-12A | 1.20 |
| 2 | ZXD-44 | 1.50 |
| 3 | ZXD-45 | 0.31 |
| 4 | ZXD-52 | 0.059 |
| 5 | ZXD-59 | 0.061 |
| 6 | ZXD-70 | 0.18 |
| 7 | ZXD-78A | 0.17 |
| 8 | ZXD-89A | 0.74 |
| 9 | ZXD-100A | 2.00 |
| 10 | ZXD-100B | 0.85 |
| 11 | ZXD-106 | 5.20 |
| 12 | ZXD-107A | 0.12 |
| 13 | ZXD-116 | 2.30 |
| 14 | ZXD-110 | 0.69 |
| 15 | ZXD-112 | 0.48 |
| 16 | ZXD-115 | 0.22 |
| 17 | ZXD-116 | 2.30 |
| 18 | ZXD-120A | 6.60 |
| 19 | ZXD-120B | 6.5 |
| 20 | ZXD-127B | 5.20 |
| 21 | ZXD-131A | 3.60 |
| 22 | ZXD-132A | 0.64 |
| 23 | ZXD-133A | 19.50 |
| 24 | ZXD-142A | 1.60 |
| 25 | ZDL-89 | 11.58 |
| 26 | ZDL-93 | 24.84 |
| 27 | ZDL-94 | 0.18 |

TABLE 4 anti-drug resistant strains of *Acinetobacter baumannii* ($EC_{50}$, MIC (μg/mL))

| Serial | Compound | Number of resistant strains of *Acinetobacter baumannii* | | | |
|---|---|---|---|---|---|
| number | number | no. 17 | no. 18 | no. 19 | no. 20 |
| 1 | ZXD-44 | 4 | 8 | 8 | 2 |
| 2 | ZDL-101 | 4 | 4 | 4 | 2 |
| 3 | ZFD-38 | 8 | 8 | 8 | 4 |
| 4 | ZFD-42 | 4 | 4 | 4 | 1 |
| 5 | ZXD-2-1 | 4 | 4 | 8 | 4 |
| 6 | ZXD-7A | 4 | 4 | 4 | 4 |
| 7 | ZXD-7B | 8 | 8 | 4 | 2 |
| 8 | ZXD-8A | 4 | 4 | 8 | 4 |
| 9 | ZXD-8B | 4 | 4 | 4 | 4 |
| 10 | ZBM-5 | 2 | 2 | 1 | 2 |
| 11 | ZBM-6 | 2 | 4 | 2 | 4 |
| 12 | ZBM-8 | 2 | 4 | 2 | 4 |
| 13 | ZBM-11 | 1 | 2 | 1 | 1 |
| 14 | ZBM-15 | 1 | 2 | 1 | 2 |
| 15 | ZBM-19 | 2 | 2 | 2 | 1 |
| 16 | ZBM-20 | 0.5 | 1 | 0.5 | 0.5 |

TABLE 4-continued anti-drug resistant strains of *Acinetobacter baumannii* ($EC_{50}$, MIC (μg/mL))

| Serial | Compound | Number of resistant strains of *Acinetobacter baumannii* | | | |
|---|---|---|---|---|---|
| number | number | no. 17 | no. 18 | no. 19 | no. 20 |
| 17 | ZBM-21 | 0.5 | 0.5 | 0.5 | 0.5 |
| 18 | ZFD-44 | 0.5 | 1 | 1 | 1 |
| 19 | ZSD-16 | 2 | 8 | 4 | 4 |
| 20 | ZSD-28B | >64 | 8 | 8 | 8 |
| 21 | Positive drug | 1 | 1 | 2 | 0.5 |
| 22 | | | | | |

TABLE 5 anti-drug resistant strains of *Acinetobacter baumannii* (inhibition zone, diameter (mm))

| Serial | Compound | Number of resistant strains of *Acinetobacter baumannii* | | | | |
|---|---|---|---|---|---|---|
| number | number | no. 16 | no. 17 | no. 18 | no. 19 | no. 20 |
| 1 | Blank | 6 | 6 | 6 | 6 | 6 |
| 2 | Positive control | 6 | 6 | 6 | 6 | 6 |
| 3 | ZBM-24 | 38 | 68 | 6 | 50 | 68 |
| 4 | ZBM-28 | 51 | 68 | 64 | 64 | 68 |
| 5 | ZBM-29 | 51 | 68 | 48 | 68 | 68 |
| 6 | ZBM-30 | 45 | 68 | 45 | 68 | 68 |
| 7 | ZBM-36 | 30 | 58 | 21 | 68 | 68 |
| 8 | ZSD-54 | 50 | 58 | 47 | 68 | 68 |
| 9 | ZXD-F | 65 | 68 | 68 | 68 | 68 |
| 10 | ZSD-15 | 44 | 40 | 68 | 68 | 40 |
| 11 | ZKD-4A | 58 | 40 | 66 | 68 | 62 |
| 12 | ZKD-4B | 68 | 68 | 68 | 68 | 68 |
| 13 | ZKD-5A | 68 | 68 | 68 | 68 | 68 |
| 14 | ZKD-5B | 68 | 48 | 48 | 55 | 68 |
| 15 | ZKD-6A | 45 | 43 | 20 | 25 | 64 |
| 16 | ZKD-6B | 16 | 17 | 16 | 20 | 40 |
| 17 | ZKD-10A | 56 | 53 | 55 | 48 | 68 |
| 18 | ZKD-10B | 39 | 48 | 45 | 46 | 54 |
| 19 | ZKD-12A | 65 | 68 | 68 | 58 | 68 |
| 20 | ZKD-12B | 68 | 68 | 55 | 60 | 68 |
| 21 | ZKD-13A | 68 | 68 | 68 | 64 | 68 |
| 22 | ZKD-13B | 68 | 68 | 36 | 64 | 68 |
| 23 | ZKD-14A | 68 | 68 | 45 | 64 | 68 |
| 24 | ZKD-14B | 54 | 53 | 34 | 68 | 68 |
| 25 | ZKD-15A | 46 | 50 | 40 | 68 | 68 |
| 26 | ZKD-15B | 67 | 68 | 40 | 68 | 68 |
| 27 | ZKD-17 | 67 | 68 | 36 | 68 | 68 |
| 28 | ZKD-18A | 68 | 68 | 68 | 68 | 68 |
| 29 | ZKD-18B | 68 | 68 | 68 | 68 | 68 |
| 30 | ZKD-19A | 68 | 68 | 68 | 68 | 68 |
| 31 | ZKD-19B | 68 | 68 | 68 | 68 | 68 |
| 32 | ZKD-21 | 60 | 48 | 53 | 64 | 68 |

TABLE 6 compound structures and their proton nuclear magnetic resonance spectrums (Z** represents the compound number)

| Compound structures | Proton nuclear magnetic resonance spectrums |
|---|---|
| 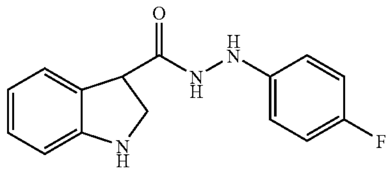 ZBM-11 | $^1H$ NMR (400 MHz, DMSO-d6) δ 9.99 (d, J = 3.9 Hz, 1H), 7.80 (d, J = 4.0 Hz, 1H), 7.13 (s, 1H), 7.03-6.85 (m, 3H), 6.74 (ddt, J = 7.4, 5.1, 2.7 Hz, 2H). 6.61-6.41 (m, 2H), 5.56 (s, 1H), 4.12-3.97 (m, 1H), 3.72-3.51 (m, 2H). |

TABLE 6-continued

| compound structures and their proton nuclear magnetic resonance spectrums (Z** represents the compound number) | |
|---|---|
| Compound structures | Proton nuclear magnetic resonance spectrums |
| 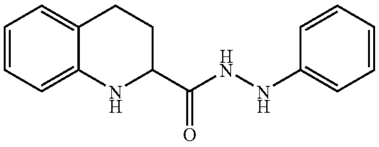 ZXD-44 | $^1$H NMR (400 MHz, DMSO-$d_6$) δ 9.67 (d, J = 2.8 Hz, 1H), 7.69 (d, J = 2.7 Hz, 1H), 7.15-7.08 (m, 2H), 6.92-6.85 (m. 2H), 6.71-6.66 (m, 3H), 6.60-6.55 (m, 1H), 6.81-6.42 (m, 1H), 3.92 (d, J = 3.1 Hz, 1H), 4.01-3.92 (m, 1H), 2.70-5.57 (m, 2H), 2.11-2.00 (m, 1H), 1.98-1.85 (m, 1H). |
| 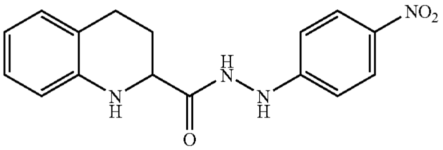 ZXD-45 | DMSO-$d_6$) δ 10.06 (s, 1H), 9.05 (s, 1H), 9.05 (s, 1H), 8.05 (d, J = 8.8 Hz, 2H), 6.94-6.86 (m, 2H), 6.75 (d, J = 9.0 Hz, 2H), 6.58 (d, J = 8.0 Hz, 1H), 6.51-6.46 (m, 1H), 6.01 (d, J = 2.9 Hz, 1H), 4.04-3.98 (m, 2H), 2.73-2.66 (m, 1H), 2.65-2.56 (m, 1H), 2.13-2.61 (m, 1H), 1.97-1.89 (m, 1H). |
| 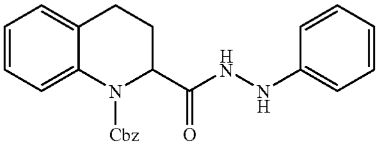 ZXD-51 | DMSO-$d_6$) δ 9.91 (d, J = 2.5 Hz, 1H), 7.68 (d, J = 2.5 Hz, 2H), 7.45-7.34 (m, 5H), 7.35-7.33 (m, 1H), 7.21-7.13 (m, 1H), 7.15-7.09 (m, 2H), 7.08-6.97 (m, 3H), 6.67-6.61 (m, 1H), 6.51 (d, J = 7.7 Hz, 2H), 5.28 (d, J = 12.7 Hz, 1H), 3.12 (d, J = 12.7 Hz, 1H), 4.96-4.87 (m, 1H), 2.70-2.64 (m, 1H), 2.63-2.57 (m, 1H), 2.40-2.29 (m, 1H), 1.85-1.75 (m, 1H). |
| 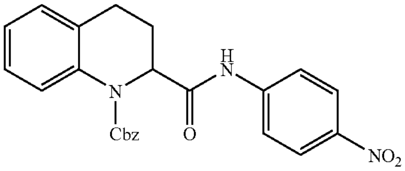 ZXD-62 | $^1$H NMR (400 MHz, DMSO -$D_6$) δ 10.77 (s, 1H), 8.22 (d, J = 9.2 Hz, 2H), 7.79 (d, J = 9.2 Hz, 2H), 7.77-7.61 (m, 1H), 7.30 (d, J = 7.7 Hz, 2H), 7.27-7.16 (m, 4H), 7.16-7.11 (m, 1H), 7.06-6.97 (m, 1H), 5.23-5.09 (m, 2H), 4.89 (dd, J = 8.8, 7.1 Hz, 1H), 2.71-2.58 (m, 2H), 2.45-2.38 (m, 1H), 1.79-1.62 (m, 1H). |
| 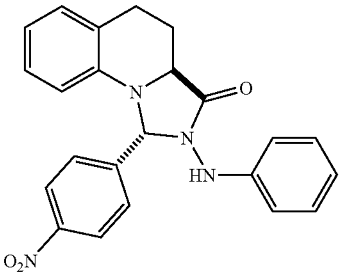 [SMILES: O=C1[C@@H]2CCc3ccccc3N2[C@@H](c2ccc([N+](=O)[O-])cc2)N1Nc1ccccc1] ZXD-70 | (400 MHz, DMSO-$d_6$) δ 8.28 (d, J = 8.7 Hz, 2H), 8.12 (s, 1H), 7.87 (d, J = 8.7 Hz, 2H), 7.11 (t, J = 7.4 Hz, 2H), 7.07 (d, J = 7.6 Hz, 1H), 6.91 (t, J = 7.5 Hz, 1H), 6.73 (t, J = 7.3 Hz, 1H), 6.66 (t, J = 7.3 Hz, 1H), 6.60 (d, J = 6.8 Hz, 2H), 6.13 (d, J = 8.1 Hz, 1H), 3.98 (d, J = 2.0 Hz, 1H), 4.59 (m, 1H), 3.00-2.86 (m, 2H), 2.34-2.31 (m, 1H), 1.68 (m, 1H). |
| 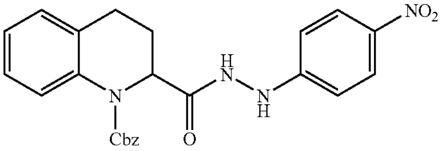 ZXD-72 | $^1$H NMR (400 MHz, DMSO=$d_6$ ) δ 10.28 (s, 1H), 9.06 (s, 1H), 7.91 (d, J = 8.7 Hz, 2H), 7.78-7.39 (m, 1H), 7.48-7.32 (m, 5H), 7.23-7.12 (m, 2H), 7.96-7.02 (m, 1H), 6.55 (d, J = 8.6 Hz, 2H), 5.30 (d, J = 12.7 Hz, 1H), 5.17 (d, J = 12.7 Hz, 1H), 4.99-4.91 (m, 1H), 2.74-2.63 (m, 1H), 2.44-2.36 (m, 1H), 1.90-1.77 (m, 1H). |
| 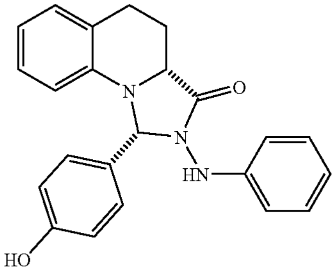 [SMILES: O=C1[C@H]2CCc3ccccc3N2[C@@H](c2ccc(O)cc2)N1Nc1ccccc1] ZXD-86A | (400 MHz, DMSO-$d_6$) δ 9.55 (s, 1H), 7.84 (s, 1H), 7.20 (d, J = 8.3 Hz, 2H), 7.11 (t, J = 7.7 Hz, 2H), 6.97 (d, J = 7.3 Hz, 1H), 6.81-6.00 (m, 6H), 6.54 (m, 1H), 6.13 (d, J = 8.1 Hz, 1H), 5.95 (s, 1H), 4.17 (d, J = 11.4 Hz, 1H), 3.08-2.94 (m, 1H), 2.89 (dd, J = 17.0, 5.8 Hz, 1H), 2.39-2.31 (m, 1H), 2.00-1.85 (m, 1H). |

TABLE 6-continued

| compound structures and their proton nuclear magnetic resonance spectrums (Z** represents the compound number) | |
|---|---|
| Compound structures | Proton nuclear magnetic resonance spectrums |
| 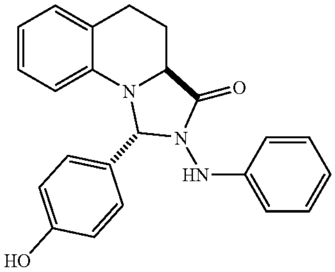 [SMILES: O=C1[C@@H]2CCc3ccccc3N2[C@@H](c2ccc(O)cc2)N1Nc1ccccc1] ZXD-86B | (400 MHz, DMSO-$d_6$) δ 9.58 (s, 1H), 7.99 (s, 1H), 7.32 (d, J = 8.5 Hz, 2H), 7.19 (t, J = 7.7 Hz, 2H), 7.03 (d, J = 7.4 Hz, 1H), 6.93-6.87 (m, 1H), 6.78 (d, J = 8.5 Hz, 2H), 6.71 (t, J = 7.3 Hz, 1H), 6.63-6.57 (m, 3H), 6.23 (d, J = 8.1 Hz, 1H), 5.65 (d, J = 2.5 Hz, 1H), 4.48 (m, 1H), 2.98-2.82 (m, 1H), 2.32-2.28 (m, 1H), 1.62 (m, 1H). |
| 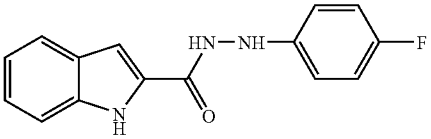 ZFD-44 | $^1$H NMR (400 MHz, DMSO) δ 11.63 (s, 1H), 10.34 (d, J = 47.0 Hz, 1H), 7.91 (s, 1H), 7.64 (d, J = 8.0 Hz, 1H), 7.50 (dd, J = 34.5, 8.5 Hz, 1H), 7.27 (s, 1H), 7.21 (dd, J = 11.3, 4.0 Hz, 1H), 7.04 (dt, J = 17.7, 8.1 Hz, 3H), 6.83-6.73 (m, 2H). |
| 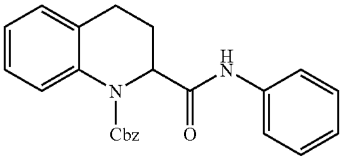 ZXD-102 | $^1$H NMR (400 MHz, DMSO-$d_6$) δ 10.14 (s, 1H), 7.82-7.58 (m, 1H), 7.55 (d, J = 7.3 Hz, 2H), 7.34-7.16 (m, 8H), 7.14 (dd, J = 7.6, 1.6 Hz, 1H), 7.07-7.03 (m, 1H), 7.05-6.96 (m, 1H), 5.22-5.10 (m, 2H), 4.87 (dd, J = 8.8, 7.1 Hz, 1H), 2.73-2.62 (m, 1H), 2.65-2.53 (m, 1H), 2.47-2.37 (m, 1H), 1.78-1.66 (m, 1H). |
| 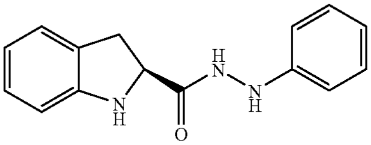 ZDL-101 | $^1$H NMR (400 MHz, DMSO) δ 9.74 (d, J = 2.8 Hz, 1H), 7.74 (d, J = 2.7 Hz, 1H), 7.13 (t, J = 7.8 Hz, 2H), 7.04 (d, J = 7.2 Hz, 1H), 6.93 (t, J = 7.4 Hz, 1H), 6.70 (t, J = 8.9 Hz, 3H), 6.58 (t, J = 7.2 Hz, 2H), 6.00 (d, J = 3.0 Hz, 1H), 4.41-4.21 (m, 1H), 3.35-3.27 (m, 1H), 3.03 (dd, J = 16.0, 8.0 Hz, 1H). |
| 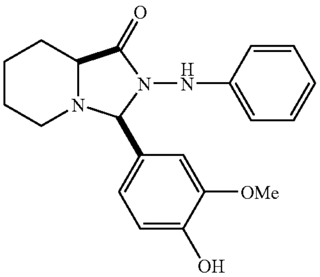 ZKD-7A | $^1$H NMR (400 MHz, DMSO-$d_6$) δ 9.08 (s, 1H), 7.72 (s, 1), 7.08 (t, J = 7.7 Hz, 2H), 6.93 (s, 1H), 6.78 (d, J = 8.0 Hz, 1H), 6.74-6.63 (m, 2H), 6.58 (d, J = 8.0 Hz, 2H), 4.84 (s, 1H), 3.73 (s, 3H), 2.95 (d, J = 9.9 Hz, 1H), 2.65 (d, J = 10.8 Hz, 1H), 2.26 (t, J = 10.5 Hz, 1H), 1.91 (dd, J = 34.6, 10.6 Hz, 2H), 1.60 (d, J = 11.6 Hz, 1H), 1.53-1.28 (m, 3H). |
| 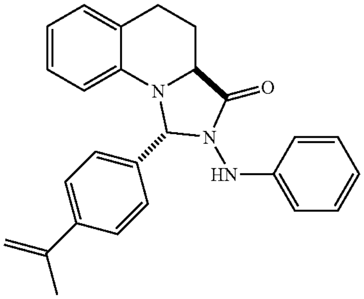 [SMILES: C=C(C)c1ccc([C@H]2N(Nc3ccccc3)C(=O)[C@@H]3CCc4ccccc4N32)cc1] ZXD-89A | (400 MHz, DMSO-$d_6$) δ 8.05 (s, 1H), 7.36 (d, J = 8.3 Hz, 2H), 7.51 (D, J = 8.3 Hz, 2H), 7.11 (t, J = 7.4 Hz, 2H), 7.04 (d, J = 7.3 Hz, 1H), 6.90 (t, J = 7.7 Hz, 1H), 6.72 (t, J = 7.2 Hz, 1H), 6.62 (t, J = 7.4 Hz, 3H), 6.21 (d, J = 8.1 Hz, 1H), 5.79 (d, J = 2.1 Hz, 1H), 5.46 (s, 1H), 5.13 (s, 1H), 4.54 (d, J = 11.8 Hz, 1H), 2.99-2.84 (m, 2H), 2.35-2.30 (m, 1H), 2.11 (s, 3H), 1.65 (m, 1H). |

TABLE 6-continued compound structures and their proton nuclear magnetic resonance spectrums (Z** represents the compound number)

| Compound structures | Proton nuclear magnetic resonance spectrums |
| --- | --- |
| 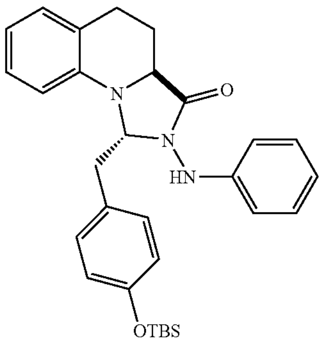 [SMILES: CC(C)(C)[Si](C)(C)Oc1ccc(C[C@H]2N(Nc3ccccc3)C(=O)[C@@H]3CCc4ccccc4N32)cc1] ZXD-126B | (400 MHz, DMSO-$d_6$) δ 8.59 (s, 1H), 7.21-7.16 (m, 2H), 7.10-7.01 (m, 3H), 6.98 (d, J = 7.2 Hz, 1H), 6.78 (t, J = 7.4 Hz, 1H), 6.74 (d, J = 8.4 Hz, 2H), 6.70 (d, J = 7.7 Hz, 2H), 6.67-6.58 (m, 2H), 5.31-5.26 (m, 1H), 3.15 (dd, J = 14.2, 3.3 Hz, 1H), 3.08 (dd, J = 14.1, 2.2 Hz, 1H), 2.86-2.78 (m, 1H), 2.74-2.65 (m. 1H), 2.61-2.52 (m, 1H), 2.62-1.94 (m, 1H), 1.40 (m, 1H), 0.92 (s, 9H), 0.14 (s, 6H). |
| 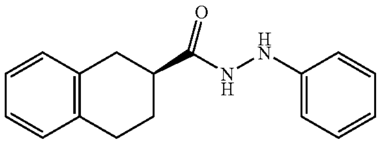 ZSD-16 | 1H NMR (400 MHz, Chloroform-d) δ 8.91-8.81 (s, 1H), 7.26-7.19 (m, 5H), 7.16-7.10 (m, 1H), 6.95-6.88 (t, J = 7.4 Hz, 1H), 6.80-6.75 (d, J = 7.9 Hz, 2H), 6.18-3.97 (m, 1H), 4.11-4.05 (d, J = 4.9 Hz, 2H), 3.83-3.77 (dd, J = 9.7, 5.5 Hz, 1H), 3.31-3.19 (dd, J = 16.3, 5.4 Hz, 1H), 3.04-2.92 (dd, J = 16.3, 9.6 Hz, 1H). |
| 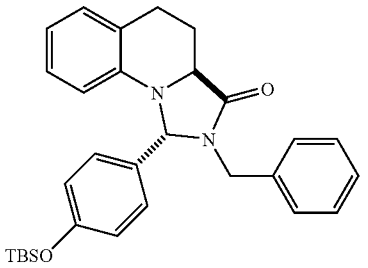 [SMILES: CC(C)(C)[Si](C)(C)Oc1ccc([C@H]2N(Cc3ccccc3)C(=O)[C@@H]3CCc4ccccc4N32)cc1] ZXD-241B | (400 MHz, DMSO-$d_6$) δ 7.37 (d, J = 8.5 Hz, 2H), 7.33-7.19 (m, 3H), 7.12-7.07 (m, 2H), 6.99 (d, J = 7.3 Hz, 1H), 6.88 (d, J = 8.5 Hz, 2H), 6.86-6.81 (m, 1H), 6.57 (td, J = 7.4, 1.1 Hz, 1H), 6.18 (d, J = 7.9 Hz, 1H), 5.44 (d, J = 2.6 Hz, 1H), 4.75 (d, J = 15.5 Hz, 1H), 4.47 (m, 1H), 3.63 (d, J = 15.5 Hz, 1H), 2.95-2.77 (m, 2H), 2.37-2.26 (m, 1H), 1.50 (m, 1H), 0.94 (s, 9H), 0.19 (d, J = 1.0 Hz, 6H). |
| 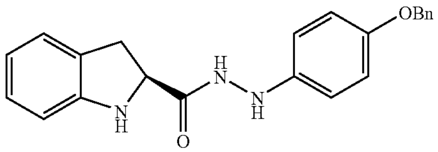 ZBM-6 | $^1$H NMR (400 MHz, DMSO) δ 9.69 (d, J = 3.3 Hz, 1H), 7.39 (dt, J = 15.6, 7.3 Hz, 6H), 7.31 (t, J = 7.0 Hz, 1H), 7.03 (d, J = 7.3 Hz, 1H), 6.94 (dd, J = 14.4, 6.7 Hz, 1H), 6.83 (d, J = 8.9 Hz, 2H), 6.68 (d, J = 8.9 Hz, 2H), 6.62-6.31 (m, 2H), 5.97 (d, J = 2.9 Hz, 1H), 4.99 (S, 2H), 4.38-4.22 (m, 1H), 3.31-3.20 (m, 1H), 3.01 (dd, J = 16.1, 7.9 Hz, 1H). |
| 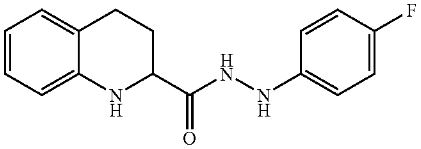 ZXD-F | $^1$H NMR (400 MHz, DMSO-$d_6$) δ 9.76-9.69 (d, J = 3.1 Hz, 1H), 7.71-7.65 (d, J = 3.0 Hz, 1H), 7.02-6.94 (t, J = 8.9 Hz, 2H), 6.94-6.83 (dd, J = 18.0, 7.7 Hz, 2H), 6.74-6.67 (m, 2H), 6.60-6.52 (m, 1H), 6.50-6.42 (m, 1H), 6.00 3.91 (d, J = 3.2 Hz, 1H), 4.00-3.90 (s, 1H), 2.73-2.53 (m, 2H), 2.11-1.86 (m, 2H). |
| 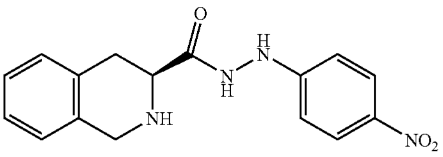 ZSD-15 | $^1$H NMR (400 MHz, Chloroform-d) δ 8.11-8.07 (d, J = 9.0 Hz, 2H), 7.25-7.15 (m, 3H), 6.64-6.58 (d, J = 9.0 Hz, 2H), 6.35-6.31 (s, 1H), 4.73-4.08 (d, J = 9.4 Hz, 2H), 3.92-3.85 (s, 1H), 3.28-3.18 (s, 1H), 3.10-3.00 (d, J = 7.8 Hz, 1H), 2.07-2.06 (s, 1H). |

TABLE 6-continued

| compound structures and their proton nuclear magnetic resonance spectrums (Z** represents the compound number) | |
|---|---|
| Compound structures | Proton nuclear magnetic resonance spectrums |
| 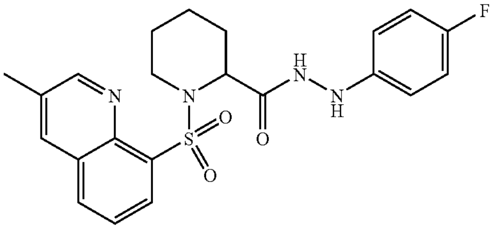 ZKD-21 | $^1$H NMR (400 MHz, DMSO-$d_6$), δ 9.91 (d, J = 2.8 Hz, 1H), 8.90 (d, J = 2.2 Hz, 1H), 8.35-8.27 (m, 2H), 8.21 (d, J = 8.2 Hz, 1H), 7.72 (S, 2H), 6.97 (t, J = 8.7 Hz, 2H), 6.64 (dd, J = 9.0, 4.6 Hz, 2H), 5.05 (D, J = 3.6 Hz, 1H), 3.77 (d, J = 13.5 Hz, 1H), 3.53 (s, J = 12.8 Hz, 1H), 2.53 (s, 3H) 2.02 (d, J = 13.5 Hz, 1H), 1.50 (d, J = 12.7 Hz, 3H), 1.38-1.25 (m, 1H), 1.06 (s, 1H). |
| 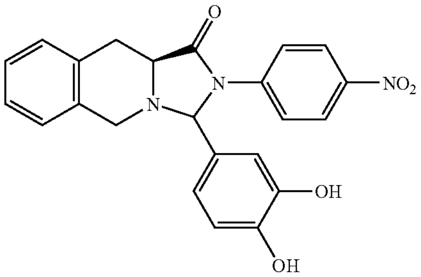 ZSD-11 | $^1$H NMR (400 MHz, Chloroform-d) δ 8.02-7.95 (d, J = 8.6 Hz, 2H), 7.49-7.43 (d, J = 8.9 Hz, 2H), 7.24-7.20 (m, 2H), 7.19-7.14 (S, 1H), 7.08-7.03 (d, J = 3.4 Hz, 1H), 6.99-6.92 (d, J = 10.2 Hz, 2H), 6.88-6.84 (d, J = 8.0 Hz, 1H), 5.92-3.61 (s, 1H), 4.19-4.10 (q, J = 7.2 Hz, 1H), 3.93-3.78 (m, 2H), 3.33-3.20 (d, J = 15.5 Hz, 1H), 3.16-3.02 (m, 1H). |
| 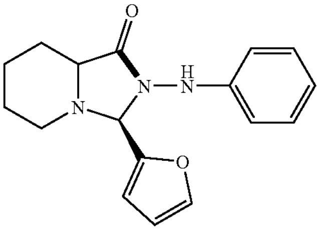 ZKD-5A | $^1$H NMR (400 MHz, DMSO-$d_6$) δ 7.89 (s, 1H), 7.70-7.57 (m, 1H), 7.13-6.99 (m, 2H), 6.72-6.66 (m, 1H), 6.66-6.61 (m, 2H), 6.60 (dd, J = 3.2, 0.9 Hz, 1H), 6.43 (dd, J = 3.3, 1.8 Hz, 1H), 5.10 (s, 1H), 2.97 (d, J = 9.6 Hz, 1H), 2.73 (dd, J = 10.9, 3.7 Hz, 1H), 2.35 (t, J = 10.2 Hz, 1H), 1.88 (dd, J = 28.8, 10.2 Hz, 2H), 1.61 (d, J = 12.2 Hz, 1H), 1.39 (pd, J = 12.1, 6.1 Hz, 3H). |
| 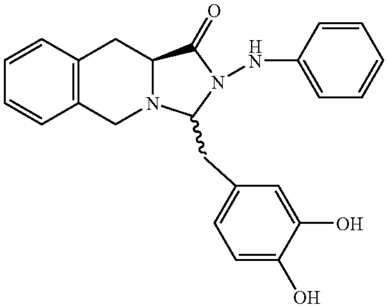 ZSD-36 | $^1$H NMR (400 MHz, Chloroform-d) δ 7.72-7.16 (td, J = 13.2, 6.2 Hz, 6H), 7.06-7.01 (d, J = 7.1 Hz, 1H), 6.98-6.92 (z, J = 7.3 Hz, 1H), 6.82-6.77 (m, 3H), 6.73-6.68 (m, 1H), 3.94-5.74 (s, 1H), 4.02-3.91 (d, J = 14.1 Hz, 1H), 3.69-3.58 (d, J = 13.9 Hz, 1H), 3.37-3.27 (d, J = 10.5 Hz, 1H), 3.27-3.13 (m, 2H), 3.09-3.00 (d, J = 12.6 Hz, 1H), 2.95-2.84 (dd, J = 14.7, 6.1 Hz, 1H). |

TABLE 7 compound structures and their NMR mass spectra

| Compound structures | Proton nuclear magnetic resonance spectrums | Compound structures | Proton nuclear magnetic resonance spectrums |
| --- | --- | --- | --- |
| 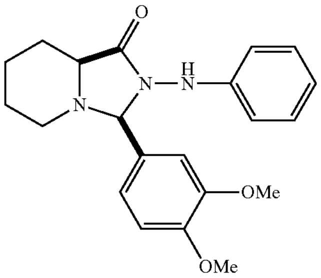 ZKD-6A | $^1$H NMR (400 MHz, DMSO-$d_6$) δ 7.75 (s, 1H), 7.08 (t, J = 7.7 Hz, 2H), 6.93 (d, J = 26.0 Hz, 3H), 6.67 (t, J = 7.3 Hz, 1H), 6.58 (d, J = 8.0 Hz, 2H), 4.90 (s, 1H), 3.73 (d, J = 5.2 Hz, 7H), 2.98 (s, 1H), 2.64 (d, J = 10.5 Hz, 1H), 2.28 (t, J = 10.5 Hz, 1H), 1.91 (dd, J = 36.4, 10.9 Hz, 2H), 1.59 (s, 1H), 1.41 (d, J = 9.1 Hz, 2H). | 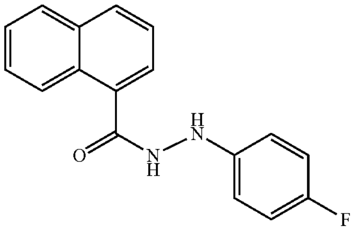 ZXN-12 | $^1$H NMR (400 MHz, DMSO) δ 10.34 (s, 1H), 8.19 (dd, J = 15.2, 8.8 Hz, 1H), 8.13-8.05 (m, 2H), 8.04-7.97 (m, 1H), 7.76 (t, J = 8.3 Hz, 1H), 7.60 (qd, J = 7.0, 3.7 Hz, 3H), 7.22 (dd, J = 8.3, 7.5 Hz, 2H), 6.89 (d, J = 8.3 Hz, 2H). |
| 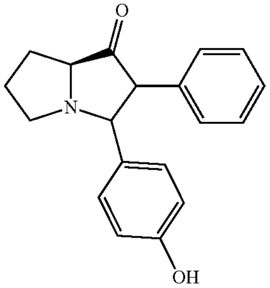 ZXP-10 | $^1$H NMR (400 MHz, $CDC1_3$) δ 7.48-7.41 (m, 1H), 7.38-7.31 (m, 2H), 7.20-7.11 (m, 2H), 6.66 6.59 (m, 4H), 4.98-4.96 (m, 1H), 3.68-3.63 (m, 1H), 3.49-3.46 (m, 1H), 2.06-1.79 (m, 6H). | 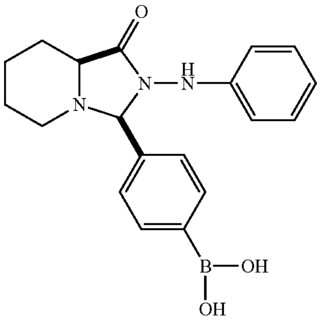 ZKD-10A | $^1$H NMR (400 MHz, DMSO-d) δ 8.07 (s, 2H), 7.82 (s, 1H), 7.77 (d, J = 7.6 Hz, 2H), 7.38 (d, J = 7.5 Hz, 2H), 7.06 (d, J = 8.3 Hz, 2H), 6.66 (1, J = 7.4 Hz, 1H), 6.57 (d, J = 8.0 Hz, 2H), 4.97 (s, 1H), 3.01 (s, 1H), 2.60 (d, J = 10.5 Hz, 1H), 2.33 (d, J = 9.7 Hz. 1H), 1.95 (d, J = 10.4 Hz, 1H), 1.86 (d, J = 9.5 Hz, 1H), 1.58 (s 1H), 1.42 (d, J = 18.9 Hz, 3H). |

TABLE 7-continued

| compound structures and their NMR mass spectra | | | |
|---|---|---|---|
| Compound structures | Proton nuclear magnetic resonance spectrums | Compound structures | Proton nuclear magnetic resonance spectrums |
| 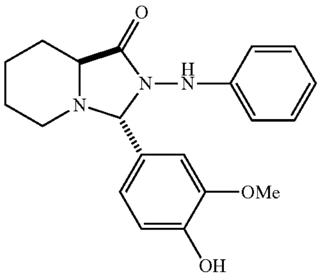 ZKD-18B | $^1$H NMR (400 MHz, Chloroform-d) δ 6.92 (dt, J = 11.0, 7.7 Hz, 4H), 6.78 (dd, J = 8.1, 1.9 Hz, 1H), 6.72 6.59 (m, 2H, 5.77 (s, 1H), 5.36 (d, J = 7.8 Hz, 2H), 3.90 (s, 3H), 3.66 (d, J = 11.5 Hz, 1H), 2.68 (dd, J = 63.4, 13.1 Hz, 2H), 2.11-1.87 (m, 2H), 1.46 (d, J = 12.8 Hz, 4H). | 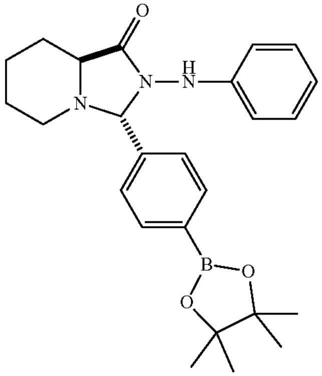 ZKD-15B | $^1$H NMR (400 MHz, DMSO-$d_6$) δ 8.04 (s, 1H), 7.69 (d, J = 7.6 Hz, 2H), 7.40 (d, J = 7.7 Hz, 2H), 7.13 (t, J = 7.7 Hz, 2H), 6.68 (dd, J = 33.2, 7.6 Hz, 3H), 5.50 (s, 1H), 2.65 (d, J = 13.8 Hz, 1H), 2.23 (t J = 12.3 Hz, 1H), 1.80 (t, J = 15.1 Hz, 3H), 1.60 (d, J = 10.5 Hz, 1H), 1.51 (d, J = 12.1 Hz, 1H), 1.39 (d, J = 13.3 Hz, 1H), 1.29 (s, 12H), 1.09-0.97 (m, 1H). |
| 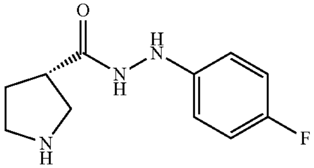 ZBM-19 | $^1$H NMR (400 MHz, DMSO) δ 10.03 (d, J = 3.2 Hz, 1H), 6.99 (t, J = 8.8 Hz, 2H), 6.74-6.67 (m, 2H), 3.63-3.34 (m, 2H), 3.34-2.93 (m, 5H), 2.24 (m, 1H), 1.97 (m, 1H). | 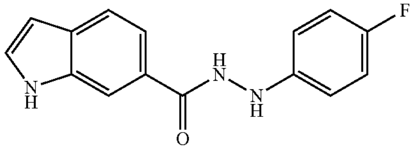 ZBM-24 | $^1$H NMR (400 MHz, DMSO) δ 11.85 (s, 1H), 8.42 (s, 1H), 8.20 (d, J = 8.5 Hz, 1H), 7.93-7.79 (m, 4H), 7.6 8 (t, J = 7.7 Hz, 1H), 7.63-7.52 (m, 2H), 6.69 (s, 1H). |
| 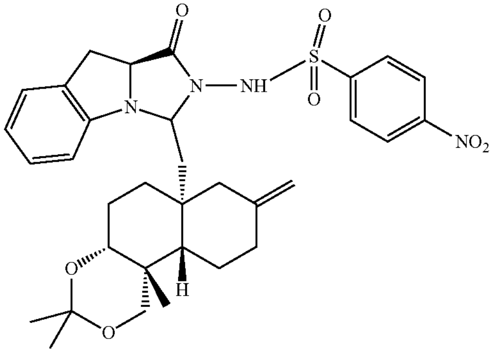 ZDL-41 | Chloroform-d) δ 7.84 (d, J = 8.4 Hz, 2H), 7.26 (m, 3H), 7.16 (s, 1H), 7.12 (d, J = 7.3 Hz, 1H), 7.06 (t, J = 7.3 Hz, 1H), 6.72 (m, 1H), 5.37 5.18 (rn, 1H), 5.08 (s, 1H), 4.84 (d, J = 9.5 Hz, 1H), 4.07-3.98 (m, 1H), 3.89 (d, J = 11.6 Hz, 1H), 3.43 (m, 1H), 3.13 (m, 2H), 2.82 (d, J = 16.3 Hz, 1H), 2.49 (d, J = 12.5 Hz, 1H), 2.18 (t, J = 12.1 Hz, 1H), 2.05 (d, J = 12.0 Hz, 1H), 1.87 (m, 1H), 1.76-1.66 (m, 2H), 1.63 1.53 (m, 2H), 1.45 (t, J = 12.4 Hz, 1H), 1.32 (d, J = 20.1 Hz, 6H), 1.25 (s, 1H), 1.10 (s, 3H), 0.94 (s, 3H). | 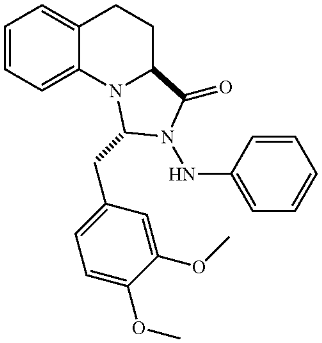 [SMILES: COc1ccc(C[C@H]2N(Nc3ccccc3)C(=O)[C@@H]3CCc4ccccc4N32)cc1OC] ZXD-140 | (400 MHz, DMSO-$d_6$) δ 8.49 (s, 1H), 7.19 (dd, J = 8.6, 7.3 Hz, 2H), 7.07 (td, J = 7.9, 1.6 Hz, 1H), 6.99 (d, J = 7.0 Hz, 1H), 6.83 (d, J = 8.2 Hz, 1H), 6.78 (t, J = 7.3 Hz, 1H), 6.75-6.69 (m, 4H), 6.65-6.60 (m, 2H), 5.29 (s, 1H), 3.71 (s, 3H), 3.56 (s, 3H), 3.18 (dd, J = 14.3, 3.5 Hz, 1H), 3.07 (dd, J = 14.2, 2.4 Hz, 1H), 2.99-2.93 (m, 1H), 2.72-2.57 (m, 2H), 2.05-2.01 (m, 1H), 1.41 (m, 1H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 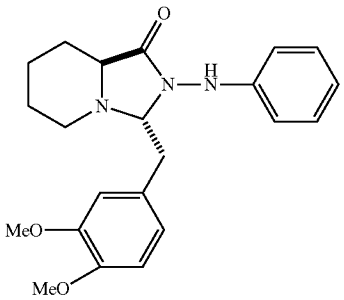 ZKD-13B | $^1$H NMR (400 MHz, DMSO-$d_6$) δ 8.13 (s, 1H), 7.25 7.11 (m, 2H), 6.86-6.82 (m, 2H), 6.80-6.76 (m, 2H), 6.75-6.70 (m, 2H), 4.61(t, J = 4.9 Hz, 1H), 3.70 (d, J = 12.7 Hz, 6H), 2.90 (d = 5.0 Hz, 2H), 2.73 (d, J = 5.8 Hz, 2H), 1.66 (s, 1H), 1.33 (s, 3H), 1.38 (s, 2H), 1.24 (s, 1H). | 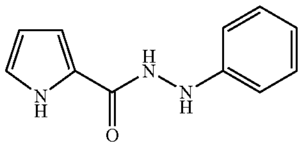 ZFD-42 | $^1$H NMR (400 MHz, DMSO) δ 11.57 (s, 1H), 9.88 (d, J = 1.9 Hz, 1H), 7.82 (d, J = 2.0 Hz, 1H), 7.14 (t, J = 7.8 Hz, 2H), 6.93 (d, J = 11.3 Hz, 2H), 6.74 (d, J = 7.8 Hz, 2H), 6.70 (t, J = 7.3 Hz, 1H), 6.13 (d, J = 2.9 Hz, 1H). |
| 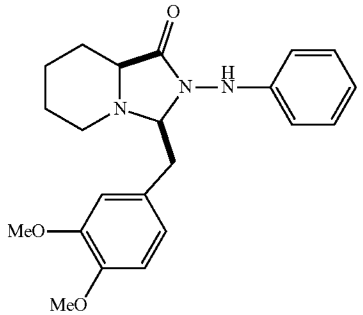 ZKD-12A | $^1$H NMR (400 MHz, DMSO-$d_6$) δ 7.81 (s, 1H), 7.67 (d, J = 7.7 Hz, 2H), 7.44 (d, J = 7.4 Hz, 2H), 7.07 (t, J = 7.6 Hz, 2H), 6.67 (t, J = 7.3 Hz, 1H), 6.57 (d, J = 8.0 Hz, 2H), 5.00 (s, 1H), 3.03 (s, 1H), 2.58 (d, J = 10.5 Hz, 1H), 2.33 (s, 1H), 1.96 (d, J = 10.3 Hz, 2H), 1.59 (d, J = 11.0 Hz, 1H), 1.42 (d, J = 18.8 Hz, 3H), 1.29 (s, 12H). | 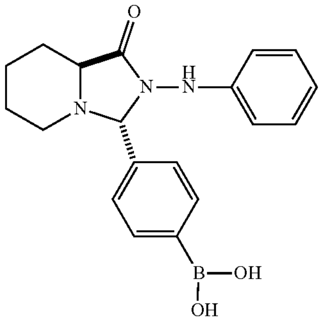 ZKD-10B | $^1$H NMR (400 MHz, DMSO) δ 9.78 (d, J = 3.0 Hz, 1H), 7.72 (d, J = 2.9 Hz, 1H), 7.05 6.91 (m, 4H), 6.75 6.67 (m, 2H), 6.63-6.46 (m, 2H), 6.00 (d, J = 3.0 Hz, 1H), 4.40-4.24 (m, 1H), 3.31 (dd, J = 13.4, 7.7 Hz, 1H), 3.01 (dd, J = 15.9, 8.2 H7, 1H). |
| 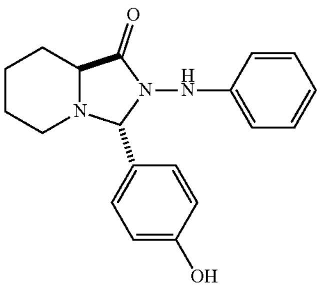 ZKD-4B | $^1$H NMR (400 MHz, DMSO) δ 12.20 (s, 1H), 9.43 (s, 1H), 8.09 (s, 2H), 7.54 (d, J = 8.3 Hz, 1H), 7.42-7.19 (m, 2H), 7.13-7.04 (m, 1H), 6.90 (t, J = 12.3 Hz, 3H), 6.75 (s, 2H), 5.97 (s, 1H), 3.77-3.61 (m, 6H). | 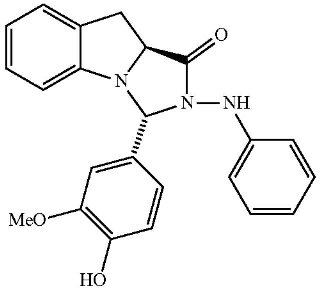 [SMILES: COc1cc([C@H]2N(Nc3ccccc3)C(=O)[C@@H]3Cc4ccccc4N32)ccc1O] ZDL-21 | $^1$H NMR (400 MHz, DMSO-$d_6$) δ 11.56 (s, 1H), 9.91 (s, 1H), 7.80 (s, 1H), 7.23-6.87 (m, 4H), 6.74 (dd, J = 8.5, 4.6 Hz, 2H), 6.13 (s, 1H). |

TABLE 7-continued

| compound structures and their NMR mass spectra | | | |
|---|---|---|---|
| Compound structures | Proton nuclear magnetic resonance spectrums | Compound structures | Proton nuclear magnetic resonance spectrums |
| 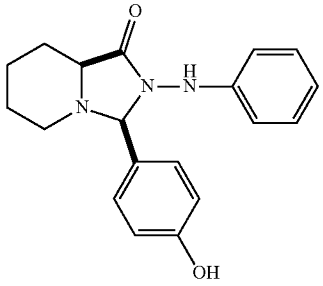 ZKD-4A | $^1$H NMR (400 MHz, Chloroform-d) δ 7.00-6.77 (m, 5H), 6.64-6.43 (m, 2H), 5.78 (s, 1H), 5.26 (s, 1H), 4.82 (d, J = 2.5 Hz, 1H), 4.14 (q, J = 7.1 Hz, 1H), 3.87 (s, 3H), 2.97 (dt, J = 11.2, 2.6 Hz, 1H), 2.81 (dd, J = 10.0, 3.6 Hz, 1H), 2.33-2.11 (m, 2H), 2.07 (s, 1H), 2.03-1.94 (m, 1H), 1.69 (d, J = 3.6 Hz, 1H), 1.41 (dddd, J = 17.1, 12.9, 8.3, 4.1 Hz, 1H). | 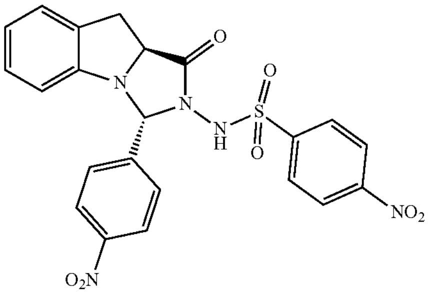 [SMILES: O=C1[C@@H]2Cc3ccccc3N2[C@@H](c2ccc([N+](=O)[O-])cc2)N1NS(=O)(=O)c1ccc([N+](=O)[O-])cc1] ZDL-38 | $^1$H NMR (400 MHz, DMSO-$d_6$) δ 9.02 (s, 1H), 7.70 (s, 1H), 6.97-6.82 (m, 4H), 6.77 (d, J = 8.2 Hz, 1H), 6.57 (t, J = 6.6 Hz, 2H), 4.80(s, 1H). 3.74 (s, 3H), 2.95 (s, 1H), 2.62 (d, J = 10.6 Hz, 1H), 2.27 (d, = 11.2 Hz, 1H), 1.87 (s, 2H), 1.59 (s, 1H), 1.38 (t, J = 10.7 Hz, 3H). |
| 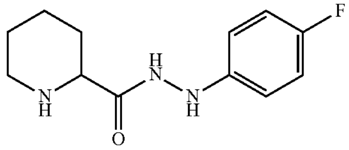 [SMILES: O=C(NNc1ccc(F)cc1)C1CCCCN1] ZKD-17 | $^1$H NMR (400 MHz, DMSO) δ 8.43 (s, 1H), 8.33 (d, J 8.7 Hz, 2H), 7.92 (d, J = 8.7 Hz, 2H), 7.40 (d, J = 7.8 Hz, 1H), 7.29 (t, J = 8.6 Hz, 2H), 7.03 (d, J = 5.8 Hz, 1H), 6.96 (t, J = 7.8 Hz, 2H), 6.67 (t, J = 7.3 Hz, 1H), 6.26 (d, J = 7.81 Hz, 2H), 6.16 (s, 1H), 4.66 (dd, J = 8.8, 3.7 Hz, 1H), 3.32 (m, 2H). | 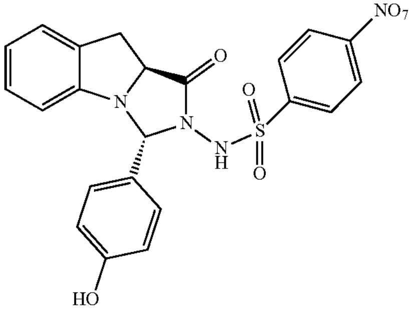 ZDL-39 | $^1$H NMR (400 MHz, DMSO) δ 9.41 (s, 1H), 7.89 (d, J = 9.1 Hz, 2H), 7.30 (d, J = 7.2 Hz, 3H), 7.13 (d, J = 14.2 Hz, 2H), 7.03 (s, 2H), 6.36 (d, J = 8.2 Hz, 2H), 5.90 (s, 1H), 4.79 (s, 1H), 3.85-3.73 (m, 6H), 3.34-3.31 (m, 2H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 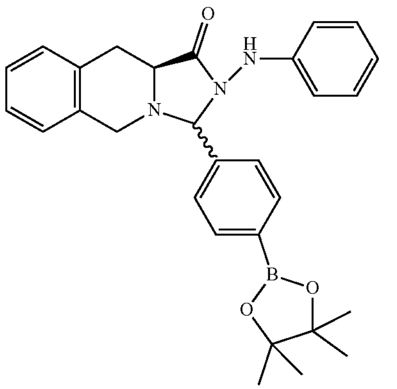 ZSD-32 | $^1H$ NMR (400 MHz, DMSO) δ 9.42 (s, 1H), 7.86 (d, J = 8.9 Hz, 2H), 7.25 (t, J = 23.5 Hz, 4H), 7.04 (t, J = 8.2 HZ, 3H), 6.33 (d, J = 8.8 Hz, 2H), 5.87 (s, 1H), 4.72 (s, 1H), 3.78 (s, 3H), 3.33 (s, 2H), 0.94 (s, 9H), 0.22-0.04 (m, 6H). | 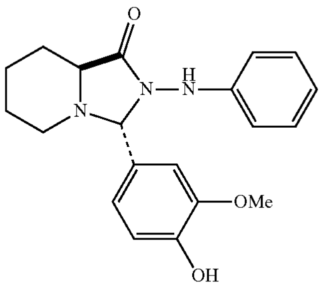 ZKD-7B | $^1H$ NMR (400 MHz, DMSO) δ 9.12 (s, 1H), 8.11 (d, J = 86.1 Hz, 1H), 7.27 (t, J = 6.3 Hz, 3H), 7.01-6.91 (m, 6H), 6.64 (t, J = 7.3 Hz, 1H), 6.25 (d, J = 7.8 Hz, 2H), 5.76 (s, 1H), 4.54 (dd, J = 8.3, 4.2 Hz, 1H), 3.80 (s, 3H), 3.31 (d, J = 8.7 Hz, 2H). |
| 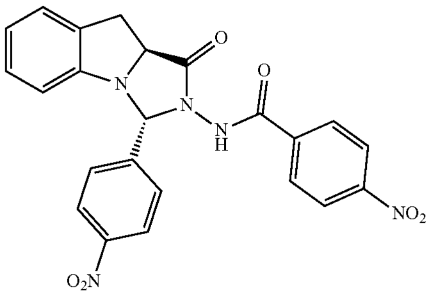 [SMILES: O=C(NN1C(=O)[C@@H]2Cc3ccccc3N2[C@H]1c1ccc([N+](=O)[O-])cc1)c1ccc([N+](=O)[O-])cc1] ZDL-11 | (400 MHz, DMSO-$d_6$) δ 8.68 (s, 1H), 7.96 (d, J = 8.7 Hz, 2H), 7.27-7.22 (m, 2H), 7.15 (t, J = 7.2 Hz, 1H), 7.04-6.99 (m, 3H), 6.94 (d, J = 7.9 Hz, 1H), 6.86-6.82 (m, 3H), 6.75 (t, J = 7.3 Hz, 1H), 5.82-5.81 (m, 1H), 3.95 (dd, J = 11.8, 2.4 Hz, 1H), 3.60 (m., 1H), 3.19 (d, J = 15.8 Hz, 1H), 2.76 2.66 (m, 1H), 2.49-2.45 (m, 1H), 1.74-1.65 (m, 1H), −0.08 (m, 1H). | 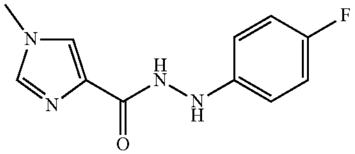 [SMILES: Cn1cnc(C(=O)NNc2ccc(F)cc2)c1] ZBM-29 | (400 MHz, DMSO-$d_6$) δ 8.66 (s, 1H), 8.14 (d, J = 8.6 Hz, 2H), 7.49 (d, J = 8.7 Hz, 2H), 7.19 (t, J = 7.9 Hz, 2H), 7.10 (t, J = 7.7 Hz, 1H), 7.01 (d, J = 7.0 Hz, 1H), 6.80 (t, J = 7.3 Hz, 1H), 6.75-6.65 (m, 4H), 5.43-5.41 (m, 1H), 3.44-3.33 (m, 2H), 3.01 (d, J = 10.1 Hz, 1H), 2.72 2.60 (m., 2H), 2.04 1, 99 (m, 1H), 1.38 (m, 1H). |
| 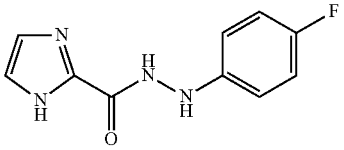 ZBM-28 | $^1H$ NMR (400 MHz, $CDCl_3$) δ 8.30 (d, J = 8.7 Hz, 2H), 7.58 (d, J = 8.8 Hz, 2H), 7.44-7.16 (rn, 5H), 4.14 (q, J = 7.1 Hz, 1H), 3.83 3.68 (m, 2H), 3.29 (d, J = 17.9 Hz, 2H), 3.13 (s, 1H), 1.35 1.21 (m, 3H). | 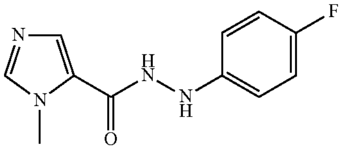 ZBM-30 | $^1H$ NMR (400 MHz, DMSO-$d_6$) δ 0.09 (s, 1H), 8.08 (s, 1H), 7.18 7, 12 (m, 2H), 6.92 (S, 1H), 6.65-6.55 (m, 5H), 4.84 (s, 1H), 3.72 (s, 3H), 3.03 (d, J = 3.6 Hz 1H), 2.95 (d, J = 9.7 Hz, 1H), 2.72 (d, J = 5.4 Hz, 1H), 2.26 (t, J = 10.9 Hz, 1H), 1.95 (d, J = 10.7 Hz, 1H), 1.59 (t, J = 12.5 Hz, 3H), 1.32-1.21 (m, 3H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 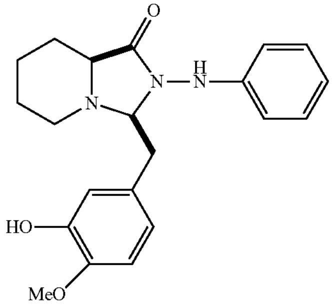 ZKD-12A | $^1$H NMR (400 MHz, DMSO-$d_6$) δ 8.80 (s, 1H), 8.06 (s, 1H), 7.16 (t, J = 7.7 Hz, 2H), 6.75 (q, J = 7.8, 7.3 Hz, 2H), 6.69 (d, J = 7.9 Hz, 2H), 6.66-6.34 (m, 2H), 4.26 (s, 1H), 3.71 (s, 3H), 3.01 (d, J = 14.1 Hz, 1H), 2.78 (s, 2H), 2.62 (dd, J = 14.5, 6.3 Hz, 1H), 2.08 (s, 1H), 1.88-1.68 (m, 2H), 1.51 (t, J = 20.5 Hz, 2H), 1.26 (s, 2H). | 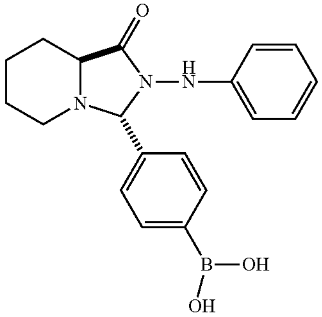 ZKD-10B | $^1$NMR (400) MHz, DMSO-$d_6$) δ 8.08 (s, 2H), 8.04 (s, 1H), 7.80 (d, J = 7.6 Hz, 2H), 7.34 (d, J = 7.6 Hz, 2H), 7.14 (t, J = 7.7 Hz, 2H), 6.72 (t, J = 7.5 Hz, 1H), 6.65 (d, J = 8.0 Hz, 2H), 5.48 (s, 1H), 2.68 (d, J = 11.8 Hz, 1H), 2.20 (t, J = 12.0 Hz, 1H), 1.79 (d, J = 12.8 Hz, 2H), 1.64-1.45 (m, 2H), 1.25 (d, J = 5.5 Hz, 3H). |
| 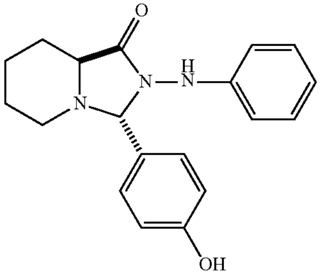 ZKD-4B | $^1$H NMR (400 MHz, DMSO-$d_6$) δ 9.51 (s, 1H), 7.91 (s, 1H), 7.20 7.15 (m, 2H), 7.12 (t, J = 7.7 Hz, 2H), 6.75 (d, J = 8.4 Hz, 2H), 6.70 (t, J = 7.3 Hz, 1H), 6.63 (d, J = 8.0 Hz, 2H), 5.45-5.18 (m, 1H), 2.65 (d, J = 14.0 Hz, 2H), 2.28 (t, J = 12.2 Hz, 1H), 1.80 (dd, J = 28.4, 12.2 Hz, 2H), 1.54 (dd, J = 32.0, 12.5 Hz, 2H), 1.36 (t, J = 14.7 Hz, 2H). | 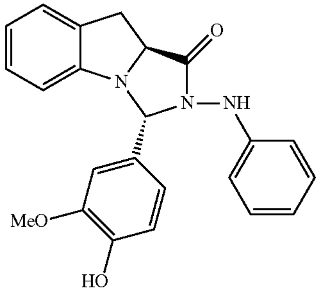 [SMILES: COc1cc([C@H]2N(Nc3ccccc3)C(=O)[C@@H]3Cc4ccccc4N32)ccc1O] ZDL-21 | $^1$H NMR (400 MHz, DMSO) δ 9.16 (s, 1H), 8.23 (s, 1H), 7.28 (dd, J = 8.3, 5.5 Hz, 2H), 7.08 (d, J = 1.7 Hz, 1H), 6.96 (dd, J = 12.9, 5.4 Hz, 3H), 6.83 (d, J = 8.1 Hz, 1H), 6.71 (d, J = 8.7 Hz, 1H), 6.64 (t, J = 6.6 Hz, 1H), 6.58 (t, J = 7.2 Hz, 1H), 6.26 (d, J = 7.9 Hz, 2H), 5.79 (s, 1H), 4.63 (dd, J = 9.2, 3.0 Hz, 1H), 3.81 (s, 3H), 3.30 (d, J = 9.8 Hz, 2H). |

TABLE 7-continued

| compound structures and their NMR mass spectra | | | |
|---|---|---|---|
| Compound structures | Proton nuclear magnetic resonance spectrums | Compound structures | Proton nuclear magnetic resonance spectrums |
| 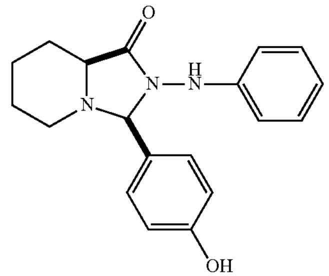 ZKD-4A | $^1$H NMR (400 MHz, DMSO-$d_6$) δ 9.54 (s, 1H), 7.71 (s, 1H), 7.27 7.10 (m, 2H), 7.07 (t, J = 7.7 Hz, 2H), 6.79-6.42 (m, 5H), 4.84 (s, 1H), 2.94 (d, J = 9.6 Hz, 1H), 2.62 (d, J = 10.4 Hz, 1H), 2.25 (t, J = 10.4 Hz, 1H), 1.94 (d, J = 10.1 Hz, 1H), 1.86 (d, J = 9.5 Hz, 1H), 1.60 (d, J = 11.6 Hz, 1H), 1.40 (d, J = 12.5 Hz, 3H). | 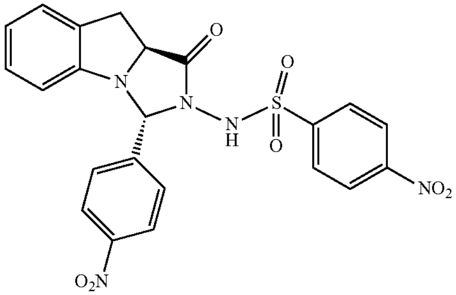 [SMILES: O=C1[C@@H]2Cc3ccccc3N2[C@@H](c2ccc([N+](=O)[O-])cc2)N1NS(=O)(=O)c1ccc([N+](=O)[O-])cc1] ZDL-38 | 1H NMR (400 MHz, DMSO) δ 11.47 (s, 1H), 8.36 (d, J = 8.7 Hz, 2H), 8.09 (d, J = 8.8 Hz, 2H), 7.83 (d, J = 8.7 Hz, 2H), 7.57 (d, J = 8.0 Hz, 1H), 7.40 (t, J = 7.6 Hz, 1H), 7.32 (d, J = 8.8 Hz, 3H), 7.17 (t, J = 7.3 Hz, 1H), 6.36 (s, 1H), 4.38 (d, J = 9.1 Hz, 1H), 3.16 (dd, J = 16.2, 10.4 Hz, 1H), 2.91 (d, J = 15.9 Hz, 1H). |
| 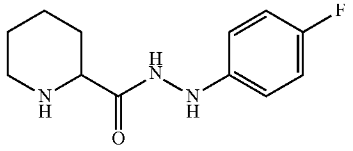 [SMILES: O=C(NNc1ccc(F)cc1)C1CCCCN1] ZKD-17 | $^1$H NMR (400 MHz, DMSO-$d_6$) δ 10.39 (s, 1H), 9.47 (s, 1H), 7.00 (dd, J = 9.5, 7.7 Hz, 2H), 6.75 (ddd, J = 8.8, 4.6, 1.4 Hz, 2H), 3.22 (d, J = 12.8 Hz, 1H), 2.93 (d, J = 11.9 Hz, 1H), 2.21 (d, J = 12.7 Hz, 1H), 1.91 (s, 1H), 1.85 1.46 (m, 6H). | 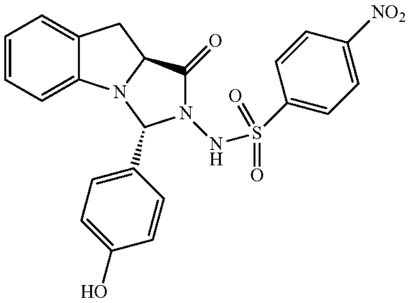 [SMILES: O=C1[C@@H]2Cc3ccccc3N2[C@@H](c2ccc(O)cc2)N1NS(=O)(=O)c1ccc([N+](=O)[O-])cc1] ZKD-39 | $^1$H NMR (400 MHz, DMSO) δ 11.25 (s, 1H), 9.68 (s. 1H), 8.07 (d, J = 8.8 Hz, 2H), 7.44 7.33 (m, 2H), 7.29 (dd, J = 8.6, 3.3 Hz, 5H), 7.12 (t, J = 7.0 Hz, 1H), 6.84 (d, J = 8.5 Hz, 2H), 6.07 (s, 1H), 4.33 (d, J = 9.4 Hz, 1H), 3.13 (dd, J = 16.2, 9.9 Hz, 1H), 2.87 (d, J = 16.3 Hz, 1H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 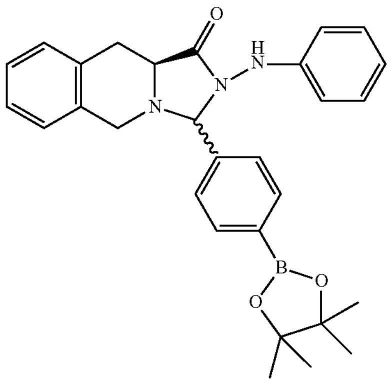 ZSD-32 | $^1$H NMR (400 MHz, DMSO-$d_6$) δ 7.92 (d, J = 7.8 Hz, 1H), 7.68 (d, J = 7.7 Hz, 2H), 7.49 (d, J = 7.6 Hz, 2H), 7.29 6.98 (m, 7H), 6.67 (dd, J = 22.1, 7.7 Hz, 3H), 5.26 (s, 1H), 3.83 (d, J = 14.3 Hz, 1H), 3.69 3.52 (m, 2H), 3.11 (dd, J = 15.8, 3.9 Hz, 1H), 3.05-2.86 (m, 1H), 1.28 (s, 13H). | 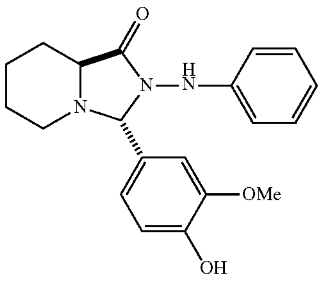 ZKD-7B | $^1$H NMR (400 MHz, DMSO-$d_6$) δ 9.07 (s, 1H), 7.94 (s, 1H), 7.14 (t, J = 7.7 Hz, 2H), 6.89 (s, 1H), 6.73 (d, J = 14.0 Hz, 3H), 6.65 (d, J = 7.9 Hz, 2H), 5.37 (s, 1H), 3.76 (s, 3H), 3.40 (d, J = 9.6 Hz, 1H), 2.69 (d, J = 11.7 Hz, 2H), 2.28 (t, J = 12.2 Hz, 1H), 1.80 (dd, J = 26.7, 12.8 Hz, 2H), 1.63-1.44 (m, 1H), 1.37 (t, J = 15.5 Hz, 2H). |
| 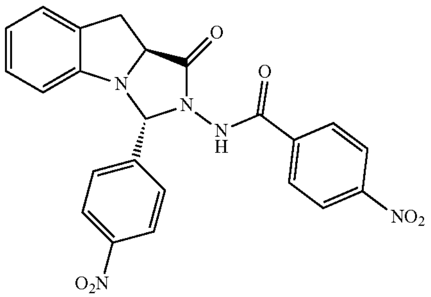 [SMILES: O=C(NN1C(=O)[C@@H]2Cc3ccccc3N2[C@H]1c1ccc([N+](=O)[O-])cc1)c1ccc([N+](=O)[O-])cc1] ZDL-11 | DMSO-$d_6$) δ 11.23 (s, 1H), 8.39-8.25 (m, 4H), 7.98 (m, 4H), 7.34 7.15 (m, (3H, 7.00 (td, J = 7.1, 1.6 Hz, 1H), 6.14 (s, 1H), 4.85 (t, J = 6.7 Hz, 1H), 3.38 (d, J = 6.7 (Hz, 2H). | 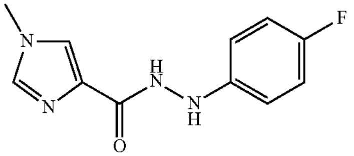 [SMILES: Cn1cnc(C(=O)NNc2ccc(F)cc2)c1] ZBM-29 | $^1$H NMR (400 MHz, DMSO) δ 9.81 (d, J = 2.8 Hz, 1H), 7.78-7.64 (m, 3H), 6.97 (t, J = 8.9 Hz, 2H), 6.70 (dd, J = 8.9, 4.6 Hz, 2H), 3.70 (s, 3H) |
| 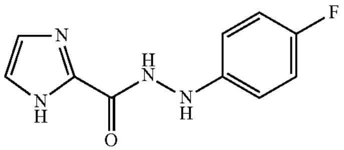 [SMILES: O=C(NNc1ccc(F)cc1)c1ncc[nH]1] ZBM-28 | $^1$H NMR (400 MHz, DMSO) δ 13.1 2 (s, 1H), 10.35 (s, 1H), 7.87 (s, 1H), 7.33 (s, 1H), 7.10 (s, 1H), 7.00 (dd, J = 16.8, 7.9 Hz, 2H), 6.73 (dd, J = 8.8, 4.6 Hz, 2H). | 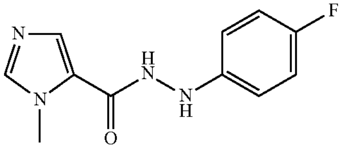 [SMILES: Cn1cncc1C(=O)NNc1ccc(F)cc1] ZBM-30 | $^1$H NMR (400 MHz, DMSO) δ 10.18 (d, J = 2.5 Hz, 1H), 7.85 (d, J = 2.5 Hz, 1H), 7.77 (d, J = 34.4 Hz, 2H), 7.00 (t, J = 8.8 Hz, 2H), 6.82-6.71 (m, 2H), 3.79 (s, 3H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 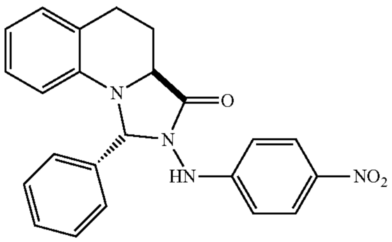 ZXD-106 | (400 MHz, DMSO-$d_6$) δ 9.40 9.10 (m, 1H), 8.20-7.70 (m, 2H), 7.70-7.30 (m, 5H), 7.06 (d, J = 7.4 Hz, 1H), 6.90 (t, J = 7.7 Hz, 1H), 6.88 6.34 (m, 3H), 6.27 -6.07 (m, 1H), 5.95-5.65 (m, 1H), 4.75-4.55 (m, 1H), 3.01-2.86 (m, 2H), 2.34 2.26 (m, (1H, 1.90-1.50 (m, 1H). | 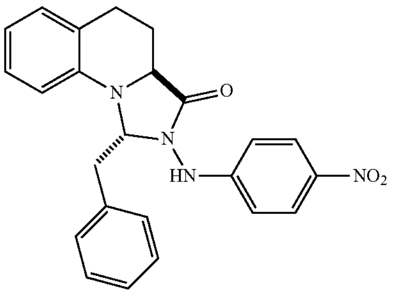 ZXD-107A | (400 MHz, DMSO-$d_6$) δ 9.65 (s, 1H), 8.12 (d, J = 9.2 Hz, 2H), 7.32-7.24 (m, 3H), 7.22 7.20 (m, 2H), 7.08 (t, J = 7.6 Hz, 1H), 7.00 (d, J = 7.1 Hz, 1H), 6.86 (d, J = 9.2 Hz, 2H), 6.65 (t, J = 7.4 Hz, 2H), 5.42 (s, 1H), 3.27 (m, 1H), 3.11 (d, J = 14.1 Hz, 1H), 2.91 2.82 (m, 1H), 2.72 2.57 (m, 2H), 2.03-1.99 (m, 1H), 1.48 (m, 1H). |
| 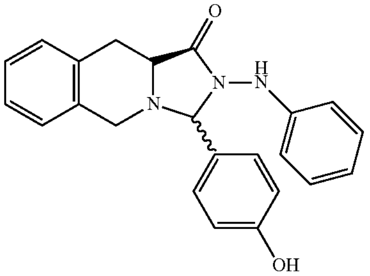 ZSD-20 | $^1$H NMR (400 MHz, DMSO-$d_6$) δ 9.55 (s, 1H), 7.83 (s, 1H), 7.29-7.23 (m, 3H), 7.21-7.11 (m, 3H), 7.11-7.05 (m, 3H), 6.77-6.72 (m, 2H), 6.69 (t, J = 7.3 Hz, 1H), 6.64 (d, J = 7.9 Hz, 2H), 5.11 (s, 1H), 3.77 (d, J = 14.4 Hz, 1H), 3.66 (d, J = 14.4 Hz, 1H), 3.50 (d, J = 11.3 Hz, 1H), 3.10 (dd, J = 16.0, 3.8 Hz, 1H), 2.97 2.86 (m, 1H). | 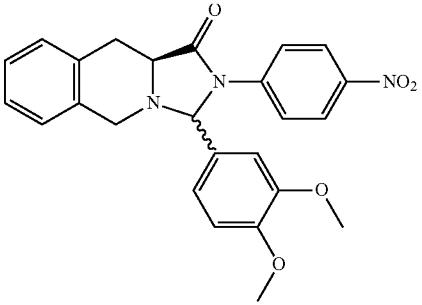 ZSD-12B | $^1$H NMR (400 MHz, DMSO-$d_6$) δ 8.23-8.14 (m, 2H), 7.87-7.81 (m, 2H), 7.27-7.23 (m, 1H), 7.18 (dt, J = 11.7, 3.5 Hz, 3H), 7.04 (s, 1H), 6.95 (d, J = 1.2 Hz, 2H), 6.23 (d. J = 1.2 Hz, 1H), 3.98 (dd, J = 9.2, 5.1 Hz, 1H), 3.91 (d, J = 14.7 Hz, 1H), 3.76 (s, 3H), 3.73 (s, 3H), 3.46 (d, J = 14.7 Hz, 1H), 3.12 (dd, 15.6, 5, 2 Hz, 1H), 2.98 (dd, J = 15.5, 9.1 Hz, 1H). |
| 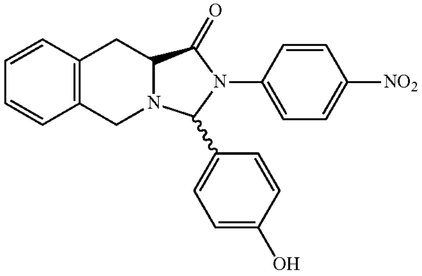 ZSD-7 | $^1$H NMR (400 MHz, DMSO-$d_6$) δ 9.61 (s, 1H), 8.18 8.10 (m, 2H), 7.62 7.53 (m, 2H), 7.33 (d, J = 8.2 Hz, 2H), 7.27 (d, J = 7.2 Hz, 1H), 7.17 (dt, J = 15.9, 7.1 Hz, 2H), 7.09 (d, J = 7.2 Hz, 1H), 6.69 (d, J = 8.3 Hz, 2H), 5.67 (d, J = 2.1 Hz, 1H), 3.81 (d, J = 14.1 Hz, 2H), 3.08-2.99 (m, 1H). | 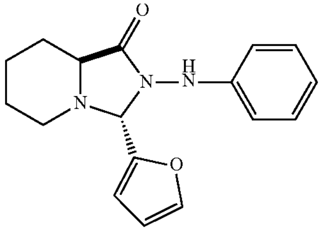 ZKD-5B | $^1$H NMR (400 MHz, DMSO-$d_6$) δ 8.12 (s, 1H), 7.73 (d J = 1.7 Hz, 1H), 7.15 (t, J = 7.7 Hz, 2H), 6.74 (t, J = 7.3 Hz, 1H), (6.66 (d, J = 7.9 Hz, 2H), 6.58 (d, J = 3.2 Hz, 1H), 6.47 (dd, J = 3.3, 1.8 Hz, 1H), 5.43 (s, 1H), 2.79 (dt, J =11.7, 3.5 Hz, 1H), 2.13 (td, J = 11.1, 3.8 Hz, 1H), 1.91-1.73 (m, 2H), 1.62 1.45 (m, 2H), 1.45 1.23 (m, 3H). |

TABLE 7-continued compound structures and their NMR mass spectra

| Compound structures | Proton nuclear magnetic resonance spectrums | Compound structures | Proton nuclear magnetic resonance spectrums |
| --- | --- | --- | --- |
| 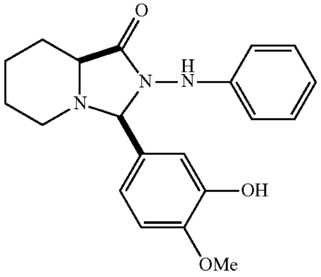 ZKD-8A | $^1$H NMR (400 MHz, DMSO-$d_6$) δ 9.00 (s, 1H), 7.71 (s, 1H), 7.08 (t, J = 7.6 Hz, 2H), 6.91 6.82 (m, 2H), 6.77 (d, J = 8.5 Hz, 1H), 6.67 (t, J = 7.3 Hz, 1H), 6.58 (d, J = 8.0 Hz, 2H), 4.82 (s, 1H), 3.75 (s, 3H), 2.96 (s, 1H), 2.63 (d, J = 10.7 Hz, 1H), 2.26 (t, J = 10.5 Hz, 1H), 1.98-1.79 (m, 2H), 1.61 (d, J = 11.5 Hz, 1H), 1.40 (q, J = 10.9, 9.0 Hz, 3H). | 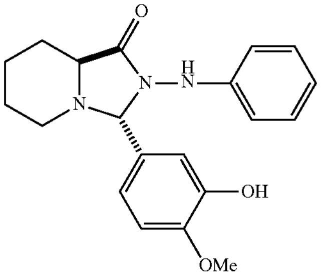 ZKD-8B | $^1$H NMR (400 MHz, DMSO-$d_6$) δ 9.01 (s, 1H), 7.92 (s, 1H), 7.13 (t, J = 7.7 Hz, 2H), 6.89 (d, J = 8.2 Hz, 1H), 6.82 (d, J = 21 Hz, 1H), 6.78-6.67 (m, 2H), 6.65 (d, J = 7.78 Hz, 2H), 5.33 (d, J = 1.6 Hz, 1H), 3.76 (s, 3H), 3.39-3.34 (m, 1H), 2.66 (d, J = 13.3 Hz, 1H), 2.27 (t, J = 12.2 Hz, 1H), 1.80 (dd, J = 26.2, 12.3 Hz, 2H), 1.62-1.52 (m, 1H), 1.49-1.26 (m, 3H). |
| 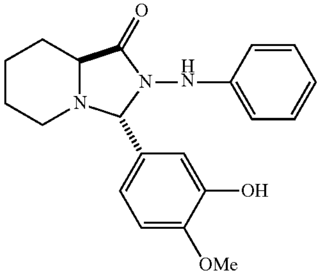 ZKD-19B | $^1$H NMR (400 MHz, DMSO-$d_6$) δ 9.03 (s, 1H), 7.91 (s, 1H), 6.98 (t, J = 8.8 Hz, 2H), 6.89 (d, J = 8.2 Hz, 1H), 6.82 6.72 (m, 2H), 6.64 (dd, J = 8.9, 4.5 Hz, 2H), 5.32 (d, J = 1.6 Hz, 1H), 3.76 (s, 3H), 3.37 (s, 1H), 2.64 (d, J = 13.0 Hz, 1H), 2.27 (t, J = 12.3 Hz, 1H), 1.79 (dd, J = 27.6, 12.7 Hz, 2H), 1.61 1.50 (m, 1H), 1.47 (d, J = 12.3 Hz, 1H), 1.42 1.24 (m, 2H). | 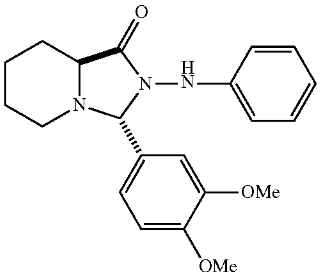 ZKD-6B | $^1$H NMR (400 MHz, DMSO-$d_6$) δ 7.97 (s, 1H), 7.14 (t, J = 7.6 Hz, 2H), 6.97-6.83 (m, 3H), 6.72 (t, J = 7.4 Hz, 1H), 6.66 (d, J = 7.9 Hz, 2H), 5.42 (s, 1H), 3.75 (d, J = 2.2 Hz, 6H), 3.41 (d, J = 11.3 Hz, 1H), 2.69 (d, J = 12.4 Hz, 1H), 2.28 (t, J = 12.4 Hz, 1H), 1.81 (dd, J = 25.3, 12.6 Hz, 2H), 1.6 (d, J = 12.6 Hz, 1H), 1.51 (q, J = 11.0 Hz, 1H), 1.42 1.29 (m, 2H). |
| 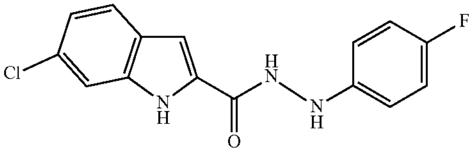 [SMILES: O=C(NNc1ccc(F)cc1)c1cc2ccc(Cl)cc2[nH]1] ZBM-36 | $^1$H NMR (400 MHz, DMSO) δ 11.91 (s. 1H), 10.49 (s, 1H), 8.01 (s, 1H), 7.74 (d, J = 1.6 (Hz, 1H), 7.45 (d, J = 8.7 Hz, 1H), 7.26 (d, J = 1.3 Hz, 1H), 7.21 (dd, J = 8.7, 2.0 Hz, 1H), 7.01 (t, J = 8.8 Hz. 2H), 6.86 6.72 (m, 2H). | 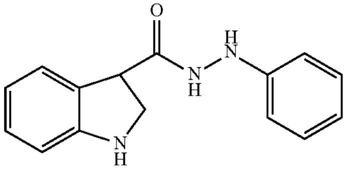 [SMILES: O=C(NNc1ccccc1)C1CNc2ccccc21] ZBM-15 | $^1$H NMR (400 MHz, DMSO), δ 9.96 (s, 1H), 7.82 (s, 1H), 7.15 (d, J = 6.6 Hz, 3H), 6.97 (s, 1H), 6.83 6.66 (m, 3H), 6.60-6.45 (m, 2H), 5.57 (s, 1H), 4.07 (d, J = 8.7 Hz, 1H), 3.61 (dd, J = 44.6, 35.2 Hz, 2H). |

TABLE 7-continued

| compound structures and their NMR mass spectra | | | |
|---|---|---|---|
| Compound structures | Proton nuclear magnetic resonance spectrums | Compound structures | Proton nuclear magnetic resonance spectrums |
| 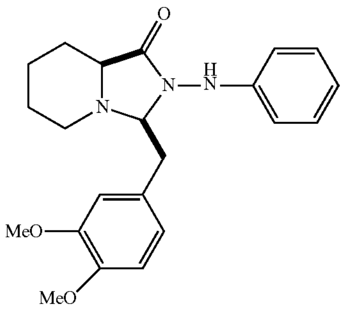 ZKD-13A | $^1$H NMR (400 MHz, ) δ 8.07 (s, 1H), 7.15 (s, J = 7.7 Hz, (2H), 6.83-6.76 (m, 2H), 6.74 (td, J = 6.8, 6.3, 3.0 Hz, 2H), 6.70-6.65 (m, 2H), 4.32 (s, 1H), 3.70 (s, 3H), 3.61 (s, 3H), 3.05 (dd, J = 14.7, 3.6 (Hz, 1H), 2.91 (d, J = 10.2 Hz, 1H), 2.77 (dd, J = 14.7, 5.2 Hz, 2H), 2.15 (s, 1H), 1.89-1.75 (m, 2H), 1.59 (d, J = 13.0 Hz, 1H), 1.46 (d, J = 11.6 Hz, 1H), 1.33-1.21 (m, 2H). | 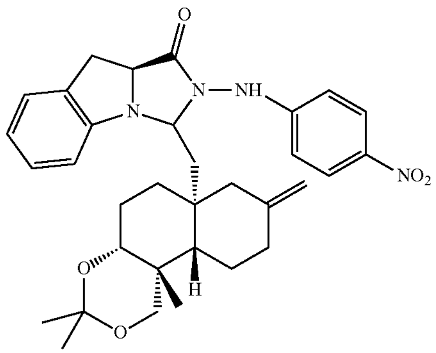 ZDL-43 | Chloroform-d), δ 7.80 (d, J = 8.7 Hz, 2H), 7.79-7.10 (m, 3H), 6.95 (m, 1H), 6.53 (d, J = 8.1 Hz, 1H), 6.23 (d, J = 8.7 Hz, 2H), 4.82 (d, J = 10.9 Hz, 2H), 4.37 (s, 1H), 4.31 (d, J = 10.7 Hz, 1H), 4.11 (d, J = 11.1 Hz, 1H), 3.42 (m, 2H), 3.35-3.29(m, 1H), 3.25 (d, J = 11.4 Hz, 1H), 2.73 (s, 2H), 2.43 (d, J = 12.6 Hz, 1H), 1.98 (dd, J = 14.6, 8.7 Hz, 2H), 1.76 (s, 3H), 1.66 (t, J = 12.5 Hz, 2H), 1.38-0.98 (m, 9H), 0.63 (s, 3H). |
| 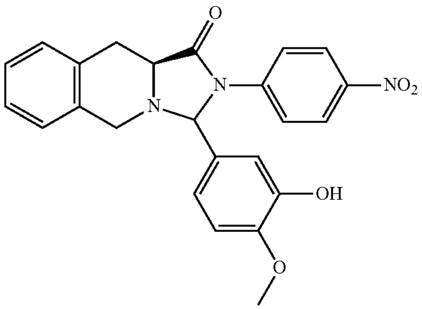 ZSD-9A | $^1$H NMR (400 MHz, DMSO-$d_6$) δ 9.04 (s, 1H), 8.21-8.09 (m, 2H), 7.65-7.57 (m, 2H), 7.27 (d, J = 7.4 Hz, 1H), 7.23-7.07 (m, 3H), 7.01 (d, J = 8.5 Hz, 1H), 6.91-6.79 (m, 2H), 5.64 (d, J = 2.1 Hz, 1H), 3.81 (d, J = 14.3 Hz, 1H), 3.72 (s, 3H), 3.68 (S, 2H), 3.06-2.97 (m, 1H). | 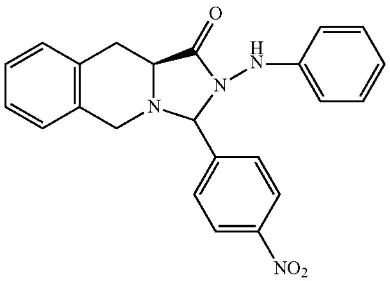 ZSD-18 | $^1$H NMR (400 MHz, DMSO-$d_6$) δ 8.33-8.21 (m, 2H), 7.93 (s, 1H), 7.69 (d, J = 8.7 Hz, 2H), 7.39) dd, J = 8.4, 3.6 Hz. 3H), 7.31 (d, J = 7.0 Hz, 1H), 6.89 (t, J = 7.8 Hz, 2H), 6.63 (t, J = 7.3 Hz, 1H), 5.83 (d, J = 7.9 Hz, 2H), 5.17 (d, J = 2.2 Hz, 1H), 4.26 (q, J = 3.5 Hz, 1H), 3.88 (s, 2H), 3.08 (d, J = 5.4 Hz, 2H). |
| 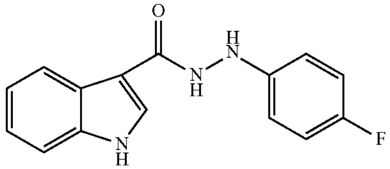 [SMILES: O=C(NNc1ccc(F)cc1)c1c[nH]c2ccccc12] ZBM-20 | $^1$H NMR (400 MHz, DMSO-$d_6$) δ 11.67 (s, 1H), 9.84 (s, 1H), 8.16 (d, J = 2.8 Hz, 1H), 8.10 (d, J = 7.9 Hz, 1H), 7.89-7.72 (m, 1H), 7.46 (d, J = 8.0 Hz, 1H), 7.14 (dt, J = 23.7, 7.3 Hz, 2H), 6.99 (t, J = 8.6 Hz, 2H), 6.81 (dd, J = 8.9, 4.7 Hz, 2H). | 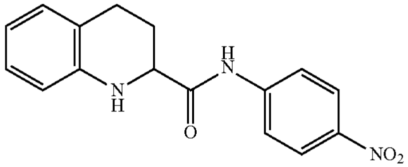 [SMILES: O=C(Nc1ccc([N+](=O)[O-])cc1)C1CCc2ccccc2N1] ZXD-53 | $^1$NMR (400 MHz, DMSO-$d_6$) δ 10.46 (s, 1H), 8.23 (d, J = 9.3 Hz, 2H), 7.92 (d, J = 9.3 Hz, 2H), 6.94-6.89 (m, 1H), 6.87 (d, J = 7.3 Hz, 1H), 6.63-6.36 (m, (1H, 6.53-6.44 (m, 1H), 6.03 (d, J = 2.4 Hz, 1H), 4.12-4.03 (m, 1H), 2.77-2.65 (m, 1H), 2.65-2.56 (m, 1H), 2.12-1.97 (m, 2H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 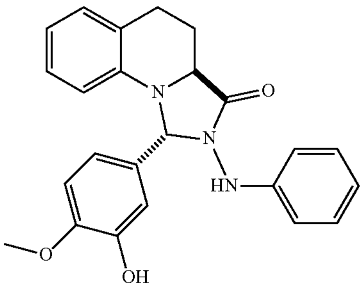 ZXD-167 | (400 MHz, DMSO-$d_6$) δ 9.11 (s, 1H), 7.98 (s, 1H), 7.11 (t, J = 7.6 Hz, 2H), 7.03 (d, J = 7.5 Hz, 1H), 6.95-6.87 (m, 4H), 6.72 (t, J = 7.4 Hz, 1H), 6.67-6.55 (m, 3H), 6.24 (d, J = 8.1 Hz, 1H), 5.62 (d, J = 2.6 Hz, 1H), 4.44 (d, J = 11.7 Hz, 1H), 3.77 (s, 3H), 3.85-2.90 (m, 1H), 2.90-2.80 (m, 1H), 2.35-2.34 (m, 1H), 1.63 (m, 1H). | 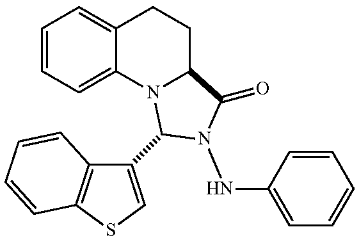 ZXD-176 | (400 MHz, DMSO-$d_6$) δ 8.13 (s, 1H), 8.08 (s, 1H), 8.06-7.99 (m, 1H), 7.89-7.82 (m, 1H), 7.43-7.34 (m, 2H), 7.96 (d, J = 7.2 Hz, 3H), 6.92-6.85 (m, 1H), 6.74-6.68 (m, 1H), 6.87-6.53 (m, (3H, 6.28 (d, J = 8.1 Hz, 1H), 6.25 (d, J = 2.6 Hz, 1H), 4.59 (d, J = 11.6 Hz, 1H), 3.04-2.84 (m, 2H), 2.40-2.32 (m, 1H), 1.72 (m, 1H). |
| 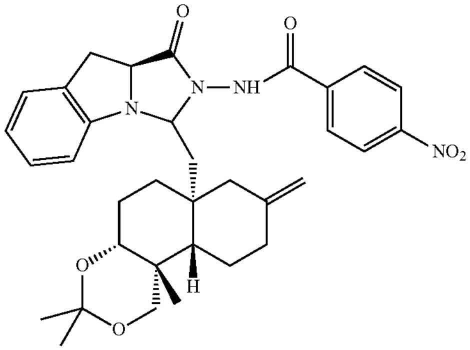 ZDL-42 | Chloroform-d) δ 9.56 (s, 1H), 8.10 (d, J = 8.2 Hz, 2H), 7.84 (d, J = 8.4 Hz, 2H), 7.08 (d, J = 7.8 Hz, 2H), 6.87 (t, J = 7.5 Hz, 1H), 6.48 (d, J = 7.9 Hz, 1H), 4.99 (d, J = 10.7 Hz, 1H), 4.90 (s, 1H), 4.43 (s, 1H), 4.35 (s, 1H), 4.06 (d, J = 10.1 Hz, 1H), 3.38 (d, J = 16.5 Hz, 2H), 3.23 (d, J = 26.2 Hz, 3H), 3.70 (s, 2H), 2.44 (d, J = 12.7 Hz, 1H), 2.06-1.84 (m, 4H), 1.26-1.18 (m, 5H), 1.10 (s, 3H), 0.81 (t, J = 6.6 Hz, 2H), 0.60 (s, 4H). | 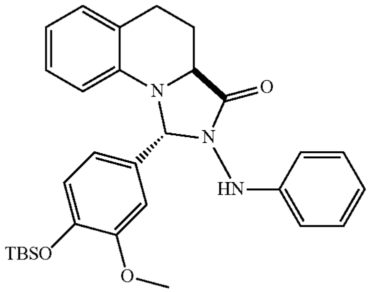 ZXD-142A | (400 MHz, DMSO-$d_6$) δ 8.02 (s, 1H), 7.09-7.03 (m, 4H), 6.99 (dd, J = 8.1, 2.1 Hz, 1H), 6.94-6.89 (m, 1H), 6.82 (d, J = 8.0 Hz, 1H), 6.70 (t, J = 7.3 Hz, 1H), 6.62 (m, 1H), 6.56 (d, J = 7.9 Hz, 2H), 6.26 (d, J = 8.0 Hz, 1H), 5.68 (d, J = 2.5 Hz, 1H), 4.54 (m, 1H), 3.72 (s, 3H), 3.90-2.83(m, 2H), 2.34-2.27 (m, 1H), 1.62 (m, 1H), 8.94 (s, 9H), 8.10 (s, 6H). |
| 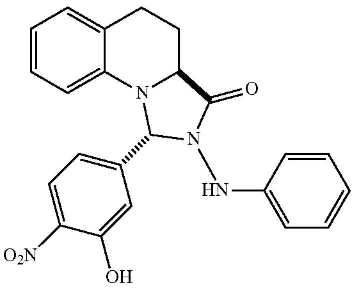 ZXD-95 | (400 MHz, DMSO-$d_6$) δ 11.10 (s, 1H), 8.11 (s, 1H), 7.93 (d, J = 8.4 Hz, 1H), 7.28 (d, J = 1.8 Hz, 1H), 7.19-7.09 (m, 1H), 7.07 (d, J = 7.2 Hz, 1H), 6.94 (m, 1H), 6.74 (t, J = 7.3 Hz, 1H), 6.70-6.57 (m, 3H), 6.18 (d, J = 8.1 Hz, 1H), 5.82 (d, J = 2.6 Hz, 1H), 4.49 (m, 1H), 3.01-2.85 (m 2H), 2.35-2.28 (m, 1H), 1.66 (m, 1H). | 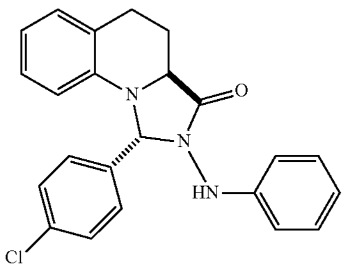 ZXD-87A | $^1$H NMR (400 MHz, DMSO-$d_6$) δ 8.07 (s, 1H), 7.58 (d, J = 8.4 Hz, 2H), 7.48 (d, J = 8.4 Hz, 2H), 7.11 (t, J = 7.5 Hz, 2H), 7.05 (d, J = 7.3 Hz, 1H), 6.91 (t, J = 7.3 Hz, 1H), 6.72 (t, J = 7.3 Hz, 1H), 6.64 (d, J = 7.4 Hz, 1H), 6.59 (d, J = 7.0 Hz, 2H), 6.17 (d, J = 8.0 Hz, 1H), 5.81 (d, J = 1.9 Hz, 1H), 4.54 (d, J = 11.9 Hz, (1H), 2.99-2.83 (m, 2H), 2.32-2.29 (m, 1H), 1.65 (m, 1H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 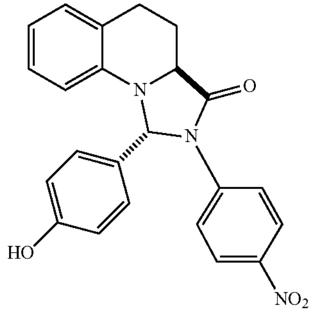 ZXD-121 | (400 MHz, DMSO-$d_6$) δ 9.60 (s, 1H), 8.19 (d, J = 9.2 Hz), 2H), 7.92 (d, J = 9.2 Hz, 2H), 7.47 (d, J = 8.6 Hz, 2H), 7.03-6.95 (m, 2H), 6.71-6.68 (m, 3H), 6.62 (td, J = 7.3, 1.1 Hz, 1H), 6.60-6.57 (m, 1H), 4.71-4.67 (m, 1H), 2.95-2.78 (m, 2H), 2.33-2.30 (m, 1H), 1.66 (m, 1H). | 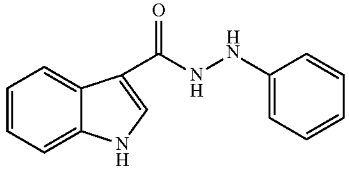 ZFD-38 | $^1$H NMR (400 MHz, DMSO) δ 11.60 (d, J = 49.7 Hz, 1H), 9.81 (s, 1H), 8.15 (d, J = 13.8 Hz, 1H), 8.11 (d, J = 7.7 Hz, 1H), 7.79 (s, 1H), 7.46 (d, J = 8.0 Hz, 1H), 7.23-7.06 (m, 4H), 6.81 (d, J = 7.8 Hz, 2H), 6.70 (t, J = 7.3 Hz, 1H). |
| 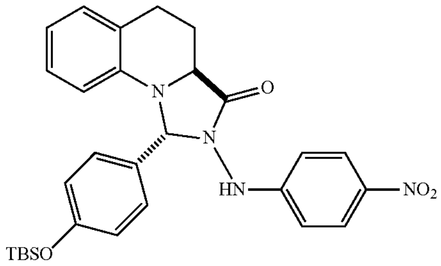 ZXD-132A | (400 MHz, DMSO-$d_6$) δ 9.73-9.68 (m, 1H), 8.15-7.85 (m, 2H), 7.52-7.36 (m, 2H), 7.05 (d, J = 7.2 Hz, 1H), 6.95-6.35 (m, 6H) 6.26-6.12 (m, 1H), 5.90-5.60 (m, 1H), 4.70-4.50 (m, 1H), 3.01-2.84 (m, 2H), 2.33-2.27 (m, 1H), 1.90-1.50 (m, 1H), 1.00-0.80 (m, 9H), 0.25-0.05 (m, 6H). | 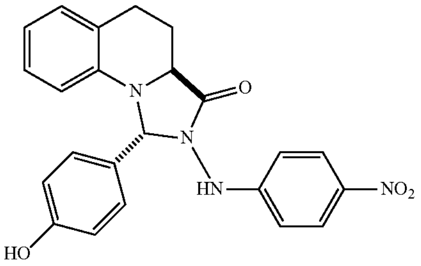 ZXD-133A | (400 MHz, DMSO-$d_6$) δ 9.75-9.68 (m, 1H), 9.35-9.05 (m, 1H), 8.15-7.80 (m, 2H), 7.45-7.25 (m, 2H), 7.04 (d, J = 7.3 Hz, 1H), 6.90 (t, J = 7.6 Hz, 1H), 6.84-6.37 (m, 5H), 6.30-6.10 (m, 1H), 5.85-3.55 (m, 1H), 4.70-4.45 (m, 1H), 3.00-2.80 (m, 2H), 2.33-2.26 (m, 1H), 1.85-1.50 (m, 1H). |
| 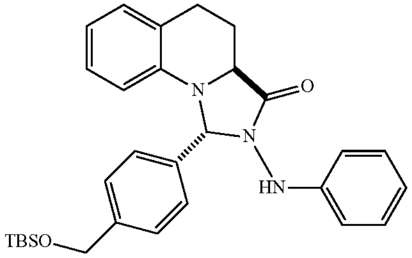 ZXD-156B | (400 MHz, DMSO-$d_6$) δ 8.05 (s, 1H), 7.52 (d, J = 7.8 Hz, 2H), 7.36 (d, J = 7.9 Hz, 2H), 7.10 (s, J = 7.4 Hz, 2H), 7.04 (d, J = 7.3 Hz, 1H), 6.92-6.86 (m, 1H), 6.72 (t, J = 7.3 Hz, 1H), 6.67-6.47 (m, 3H), 6.21 (d, J = 8.1 Hz, 1H), 5.77 (d, J = 2.6 Hz, 1H), 4.73 (s, 2H), 4.54 (m, 1H), 3.04-2.81 (m, 2H), 2.36-2.26 (m, 1H), 1.65 (m, 1H), 0.90 (s, 9H), 0.08 (d, J = 1.3 Hz, 6H). | 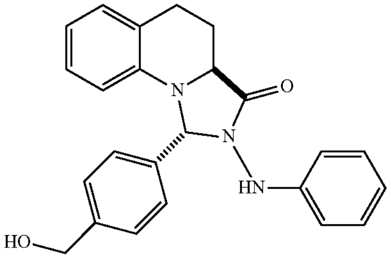 ZXD-157B | (400 MHz, DMSO-$d_6$) δ 8.05 (s, 1H), 7.49 (d, J = 7.9 Hz, 2H), 7.36 (d, J = 7.9 Hz, 2H), 7.11 (t, J = 7.6 Hz, 2H), 7.04 (d, J = 7.3 Hz, 1H), 6.91-6.86 (m, 1H), 6.72 (t, J = 7.3 Hz, 1H), 6.63-6.59 (m, 3H), 6.21 (d, J = 8.1 Hz, 1H), 5.76 (d, J = 2.5 Hz, 1H), 5.25 (t, J = 5.7 Hz, 1H), 4.56-4.50 (m, 3H), 3.00-2.83 (m, 2H), 2.33-2.28 (m, 1H), 1.65 (m, 1H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 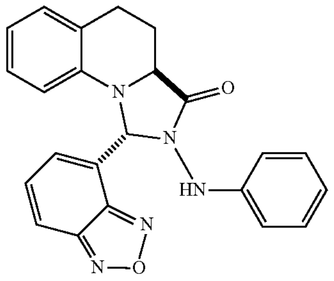 ZXD-181A | (400 MHz, DMSO-$d_6$) δ 8.16 (d, J = 9.1 Hz, 1H), 7.98 (d, J = 6.0 Hz, 2H), 7.64 (dd, J = 9.1, 6.5 Hz, 1H), 7.11 (t, J = 7.7 Hz, 2H), 7.04 (d, J = 7.3 Hz, 1H), 6.96 (m, 1H), 6.73 (t, J = 7.3 Hz, 1H), 6.66-6.62 (m, 1H), 6.60 (d, J = 8.0 Hz, 2H), 6.52 (d, J = 8.1 Hz, 1H), 6.24 (d, J = 2.4 Hz, 1H), 4.57 (m, 1H), 2.98-2.82 (m, 2H), 2.42-2.35 (m, 1H), 1.73 (m, 1H). | 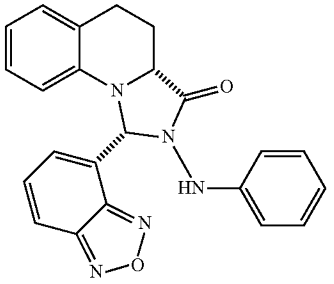 ZXD-181B | (400 MHz, DMSO-$d_6$) δ 8.04 (d, J = 9.0 Hz, 1H), 8.01-7.94 (m, 1H), 7.90 (s, 1H), 7.59 (dd, J = 9.1, 6.6 Hz, 1H), 7.12 (t, J = 7.7 Hz, 2H), 6.93 (d, J = 7.4 Hz, 1H), 6.77-6.71 (m, 2H), 6.67 (d, J = 8.0 Hz, 2H), 6.55 (s, 1H), 6.50 (t, J = 7.2 Hz, 1H), 6.40 (s, 1H), 4.36 (d, J = 10.9 Hz, 1H), 3.03-2.93 (m, 1H), 2.85 (dd, J = 16.9, 5.2 Hz, 1H), 2.46-2.35 (m, 1H), 2.31-2.24 (m, 1H). |
| 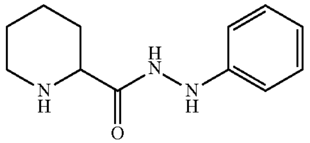 [SMILES: O=C(NNc1ccccc1)C1CCCCN1] ZKD-2-1 | $^1$H NMR (400 MHz, DMSO-$d_6$) δ 10.31 (s, 1H), 9.25 (s, 1H), 7.16 (t, J = 7.7 Hz, 2H), 6.77-6.67 (m, 3H), 3.25 (d, J = 11.0 Hz, 1H), 2.95 (d, J = 11.7 Hz, 1H), 2.22 (d, J = 13.0 Hz, 1H), 1.83 (d, J = 12.5 Hz, 1H), 1.75-1.45 (m, 6H). | 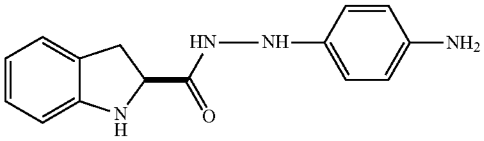 [SMILES: Nc1ccc(NNC(=O)[C@@H]2Cc3ccccc3N2)cc1] ZBM-8 | $^1$H NMR (400 MHz, DMSO), δ 9.45 (s, 1H), 7.93 (s, 2H), 7.22 (t, J = 7.9 Hz, 2H), 7.06-6.92 (m, 2H), 6.32 (s, 2H), 4.87 (s, 1H), 4.56 (t, J = 4.9 Hz, (2H, 3.51 (dd, J = 15.0, 5.2 Hz, 2H). |
| 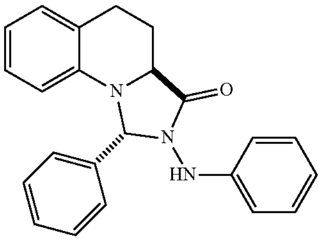 ZXD-109B | (400 MHz, DMSO-$d_6$) δ 8.07 (s, 1H), 7.54 (d, J = 6.7 Hz, 3H), 7.45-7.38 (m, 3H) 7.10 (t, J = 7.3 Hz, 2H), 7.04 (d, J = 7.2 Hz, 1H), 6.89 (t, J = 7.3 Hz, 1H), 6.71 (t, J = 7.3 Hz, 1H), 6.67-6.34 (m, 3H), 6.20 (d, J = 8.1 Hz, 1H), 8.78 (d, J = 2.1 Hz, 1H), 4.55 (d, J = 11.7 Hz, 1H), 2.98-2.83 (m, 2H), 2.36 2.27 (m, 1H), 1.65 (m, 1H). | 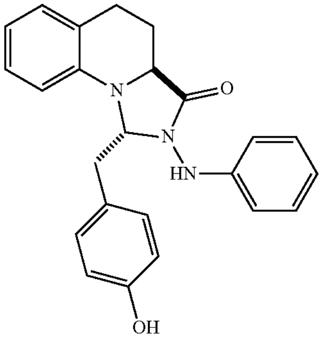 ZXD-127B | (400 MHz, DMSOd$_6$) δ 9.28 (s, 1H), 8.53 (s, 1H), 7.18 (t, J = 7.9 Hz, 2H), 7.07 (td, J = 7.8, 1.5 Hz, 1H), 6.98 (t, J = 7.6 Hz, 3H), 6.78 (t, J = 7.3 Hz, 1H), 6.73-6.68 (m, 2H), 6.68-6.60 (m, 4H), 6.32-5.23 (m, 1H), 3.06 (qd, J = 14.4, 2.7 Hz, 2H), 2.87 (d, J = 10.9 Hz, 1H), 2.72-2.98 (m, 2H), 2.05-1.98 (m, 1H, 1.38 (m, 1H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 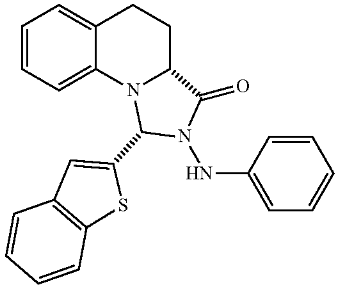 ZXD-178B | (400 MHz, DMSO-$d_6$) δ 8.11 (s, 1H), 7.90-7.85 (m, 1H), 7.83-7.78 (m, 1H), 7.74 (s, 1H), 7.36-7.29 (m, 2H), 7.15 (t, J = 7.8 Hz, 2H), 7.01 (d, J = 7.3 Hz, 1H), 6.83-6.72 (m, 4H), 6.62-6.55 ), 2H), 6.53 (d, J = 8.1 Hz, 1H), 4.25 (d, J = 11.0 Hz, 1H), 3.01 (m, 1H), 2.92 (dd, J = 17.1, 5.6 Hz, 1H), 2.39-2.32 (m, 1H), 2.03-1.88 (m, 1H). | 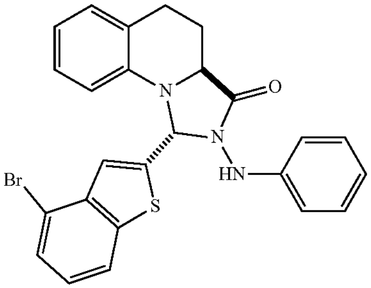 ZXD-187 | (400 MHz, DMSO-$d_6$) δ 8.26 (s, 1H), 8.02 (d, J = 8.1 Hz, 1H), 7.69 (s, 1H), 7.64 (s, J = 7.6 Hz, 1H), 7.32 (t, J = 7.9 Hz, 1H), 7.13 (t, J = 7.9 Hz, 2H), 7.08 (d, J = 7.4 Hz, 1H), 7.00-6.94 (m, 1H), 6.74 (t, J = 7.4 Hz, 1H), 6.74-6.64 (m, 3H), 6.51 (d, J = 8.1 Hz, 1H), 6.34 (d, J = 2.4 Hz, 1H), 4.40 (m, 1H), 3.03-2.92 (m, 1H), 2.93-2.82 (m, 1H), 2.35-2.30 (m, 1H), 1.69 (m, 1H). |
| 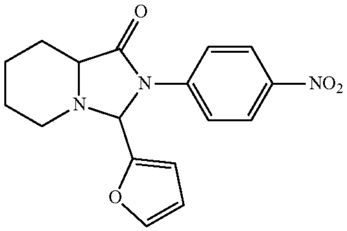 [SMILES: O=C1C2CCCCN2C(c2ccco2)N1c1ccc([N+](=O)[O-])cc1] ZBJ-12A | (400 MHz, DMSO) δ 8.15 (d, J = 9.2, 2H) 7.59 (s, 1H), 7.57 (s, 2H), 6.76 (d, J = 3.2 Hz, 1H), 6.40-6.39 (m, 1H), 5.71 (d, J = 2.0 Hz, 1H), 3.02 (d, J = 10.4 Hz, 1H), 2.75 (d, J = 10.0 Hz, 1H), 2.35 (z, J = 10.8 Hz, 8.4 Hz, 1H), 1.99 (d, J = 10.8 Hz, 1H), 1.85 (d, J = 7.6 Hz, 1H), 1.61 (d, J = 9.2 Hz, 1H), 1.45 (d, J = 11.6 Hz, 1H), 1.38-1.30 (m, 2H). | 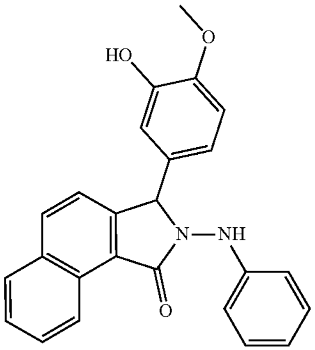 [SMILES: COc1ccc(C2c3ccc4ccccc4c3C(=O)N2Nc2ccccc2)cc1O] ZXN-7 | $^1$H NMR (400 MHz, DMSO-$d_6$) δ 10.36-10.25 (d, J = 3.1 Hz, 2H), 8.90-8.83 (s, 1H), 8.24-8.19 (d, J = 2.2 Hz, 1H), 8.10-8.07 (s, 1H), 8.04-8.01 (s, 1H), 7.79-7.76 (d, J = 1.2 Hz, 1H), 7.62-7.60 (d, J = 3.7 Hz, 2H), 7.60-7.57 (m, 3H), 6.97-6.96 (s, 1H), 6.84-6.82 (s, 2H), 6.59-6.55 (d, J = 2.1 Hz, 1H), 6.51-6.46 (m, 1H), 5.29-5.21 (s, 1H), 3.75-3.69 (s, 3H). |
| 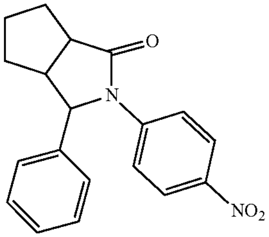 [SMILES: O=C1C2CCCC2C(c2ccccc2)N1c1ccc([N+](=O)[O-])cc1] ZDL-61 | $^1$H NMR (400 MHz, DMSO) δ 8.14 (d, J = 9.2 Hz, 2H), 7.64 (d, J = 9.2 Hz, 2H), 7.82-7.22 (m, 2H), 7.19 (t, J = 7.3 Hz, 1H), 7.11 (d, J = 7.3 Hz, 2H), 5.82 (t, J = 16.3 Hz, 1H), 3.27 (td, J = 9.2, 3.6 Hz, 1H), 3.14-3.1 (m, 1H), 2.09-1.80 (m, 2H), 1.52-1.37 (m, 2H), 1.21-0.93 (m, 2H). | 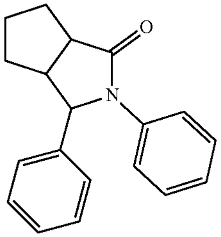 [SMILES: O=C1C2CCCC2C(c2ccccc2)N1c1ccccc1] ZDL-60 | DMSO-$d_6$) δ 7.39-7.31 (m, 2H), 7.24 (t, J = 7.7 Hz, 4H), 7.18-7.13 (m, 1H), 7.13-7.08 (m, 2H), 7.04 (t, J = 7.3 Hz, 1H), 5.76 (d, J = 8.0 Hz, 1H), 3.18 (m, J = 9.2, 3.4 Hz, 1H), 3.05 (p, J = 8.3 Hz, 1H), 1.99 (m, J = 13.1, 6.7, 3.4 Hz, 1H), 1.89 (m, 1H), 1.43 (m, 2H), 1.08 (m, 2H). |

TABLE 7-continued compound structures and their NMR mass spectra

| Compound structures | Proton nuclear magnetic resonance spectrums | Compound structures | Proton nuclear magnetic resonance spectrums |
| --- | --- | --- | --- |
| 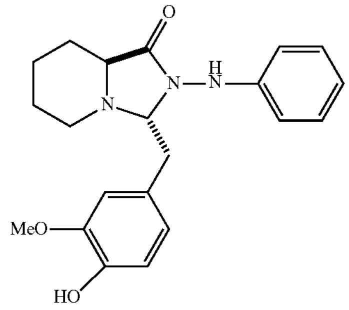 ZKD-14B | $^1$H NMR (400 MHz, DMSO-$d_6$) δ 8.73 (s, 1H), 7.94 (s, 1H), 7.13 (t, J = 7.7 Hz, 2H), 6.81 (s, 1H), 6.74 (t, J = 9.5 Hz, 5H), 4.58 (s, 1H), 3.69 (s, 3H), 2.72 (s, 2H), 2.00 (s, 1H), 1.77 (d, J = 12.3 Hz, 1H), 1.33 (s, 5H), 1.18 (t, J = 7.1 Hz, 2H). | 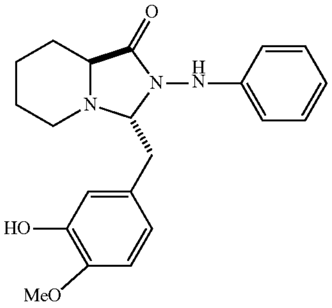 ZKD-12B | $^1$H NMR (400 MHz, DMSO-$d_6$) δ 8.80 (s, 1H), 8.19 (s, 1H), 7.20 (dd, J = 8.5, 7.2 Hz, 2H), 6.82-6.53 (m, 7H), 4.52 (s, 1H), 3.73 (s, 4H), 2.82 (d, J = 5.1 Hz, 2H), 1.67 (s, 1H), 1.54 d), J = 10.6 Hz, 2H), 1.36 d), J = 15.2 Hz, 2H), 1.27-1.23 (m, 2H). |
| 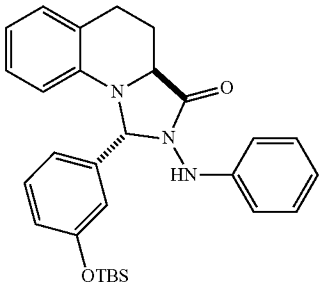 ZXD-147B | (400 MHz, DMSO-$d_6$δ 8.10 (s, 1H), 7.30 (s, J = 7.8 Hz, 1H), 7.15 (d, J = 7.6 Hz, 1H), 7.11-7.02 (m, 3H), 6.98 (z, J = 2.1 Hz, 1H), 6.91-6.83 (m, 2H), 6.70 (s, J = 7.4 Hz, 1H), 6.62 (m, 1H), 6.55 (d, J = 6.8 Hz, 2H), 6.20 (d, J = 8.1 Hz, 1H), 5.72 (d, J = 2.6 Hz, 1H), 4.51 (m, 1H), 3.00-2.83 (m, 2H), 2.34-2.25 (m, 1H), 1.63 (m, 1H), 0.92 (s, 9H), 0.13 (s, 6H). | 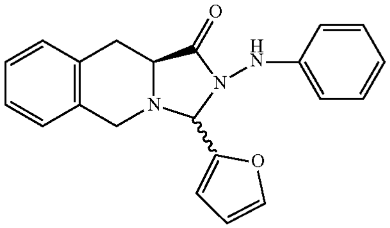 ZSD-28B | $^1$H NMR (400 MHz, DMSO-$d_6$(δ 8.02 (s, 1H), 7.72 (dd, J = 1.8, 0.8 Hz, 1H), 7.33-7.22 (m, 5H), 6.97 (dd, J = 8.4, 7.2 Hz, 2H), 6.69-6.62 (m, 1H), 6.57 (dd, J = 3.3, 0.9 Hz, 1H), 6.47 (dd, J = 3.3, 1.8 Hz, 1H), 6.09 (d, J = 8.0 Hz, 2H), 5.57 (d, J = 8.1 Hz, 1H), 5.27 (d, J = 1.8 Hz, 1H), 4.03-3.96 (m, 1H), 3.86 (d, J = 14.8 Hz, 1H), 3.70 (d, J = 14.8 Hz, 1H), 3.02 (qd, J = 15.2, 6.0 Hz, 2H. |
| 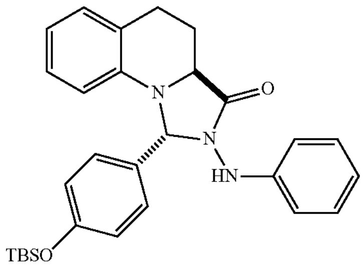 ZXD-131A | (400 MHz, DMSO-$d_6$) δ 8.05 (S, 1H), 7.42 (d, J = 8.5 Hz, 2H), 7.12-6.99 (m, 3H), 6.92-6.85 (m, 3H), 6.70 (t, J = 7.3 Hz, 1H), 6.61 (td, J = 7.4, 1.1 Hz, 1H), 6.55 (d, J = 7.8 Hz, 2H), 6.20 (d, J = 8.2 Hz, 1H), 5.71 (d, J = 2.5 Hz, 1H), 4.55-4.46 (m, 1H), 2.99-2.83 (m, 2H), 2.33-2.27 (m, 1H), 1.62 (m, 1H), 0.94 (s, 9H), 0.18 (s, 6H). | 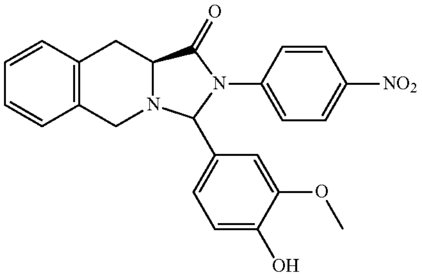 ZSD-8 | $^1$H NMR (400 MHz, DMSO-$d_6$) δ 9.15 (s, 1H), 8.20-8.10 (m, 2H), 7.65-7.57 (m, 2H), 7.27 (d, J = 7.3 Hz, 1H), 7.23-7.06 (m, 3H), 7.03 (s, 1H), 6.97 (d, J = 8.1 Hz, 1H), 6.71 (dd, J = 8.1, 2.0 Hz, 1H), 5.63 (d, J = 2.1 Hz, 1H), 3.82 (d, J = 14.3 Hz, 1H), 3.72 (s, 1H), 3.69 (s, 3H), 3.61-3.53 (m, 1H), 3.19 (dd, J = 13.8, 4.1 Hz, 1H), 3.13-3.01 (m, 1H). |

TABLE 7-continued compound structures and their NMR mass spectra

| Compound structures | Proton nuclear magnetic resonance spectrums | Compound structures | Proton nuclear magnetic resonance spectrums |
|---|---|---|---|
| 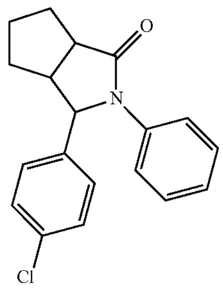 [SMILES: O=C1C2CCCC2C(c2ccc(Cl)cc2)N1c1ccccc1] ZDL-62 | DMSO-$d_6$) δ 7.38-7.32 (m, 2H), 7.32-7.28 (m, 2H), 7.28-7.22 (m, 2H), 7.18-7.10 (m, 2H), 7.65 (m, 1H), 5.77 (d, J = 8.0 Hz, 1H), 3.18 (m, 1H), 3.11-2.98 (m, 1H), 2.04-1.84 (m, 2H), 1.43 (m, 2H), 1.20-1.09 (m, 1H), 1.03 (m, 1H). | 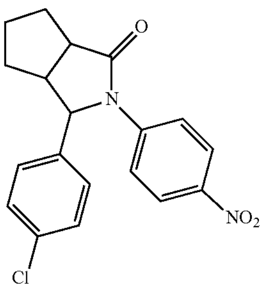 [SMILES: O=C1C2CCCC2C(c2ccc(Cl)cc2)N1c1ccc([N+](=O)[O-])cc1] ZDL-63 | DMSO-$d_6$) δ 8.25-8.06 (m, 2H), 7.69-7.56 (m, 2H), 7.43-7.24 (m, 2H), 7.15 (d, J = 8.1 Hz, 2H), 5.85 (d, J = 8.0 Hz, 1H), 3.27-3.23 (m, 1H), 3.10 (s, 1H), 1.95 (m, 2H), 1.44 (m, J = 7.1, 4.1 Hz, 2H), 1.15 (m, 1H), 1.04 (m, 1H). |
| 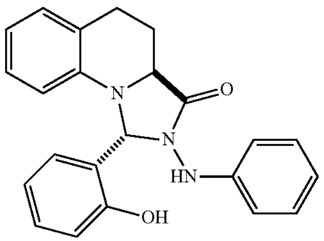 ZXD-120B | (400 MHz, DMSO-$d_6$) δ 9.89 (s, 1H), 7.93 (s, 1H), 7.41 (dd, J = 7.8, 1.7 Hz, 1H), 7.18 (td, J = 7.9, 1.7 Hz, 1H), 7.10 (s, J = 7.8 Hz, 2H), 7.01 (d, J = 7.4 Hz, 1H), 6.96-6.90 (m, 1H), 6.86-6.82 (m, 2H), 6.79 (t, J = 7.3 Hz, 1H), 6.64 (d, J= 7.8 Hz, 2H), 6.59 (m, 1H), 6.39 (d, J = 8.1 Hz, 1H), 6.05 (s, 1H), 4.41 (d, J = 9.5 Hz, 1H), 2.94-2.79 (m, 2H), 2.33-2.27 (m, 1H), 1.61 (m, 1H). | 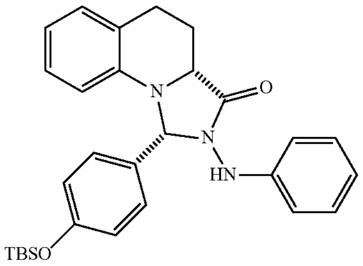 ZXD-131B | (400 MHz, DMSO-$d_6$) δ 7.89 (s, 1H), 7.30 (d, J = 8.5 Hz, 2H), 7.08 (t, J = 7.6 Hz, 2H), 6.98 (d, J = 7.3 Hz, 1H), 6.78 (d, J = 8.5 Hz, 2H), 6.75-6.68(m, 2H), 6.62 (d, J = 7.9 Hz, 2H), 6.54 (m, 1H), 6.08 (d, J = 8.0 Hz, 1H) 5.99 (s, 1H), 4.18 (d, J = 11.5 Hz, 1H), 3.07-2.95 (m, 1H), 2.90 (dd, J = 16.8, 5.8 Hz, 1H), 2.39-2.33 (m, 1H), 1.95 (m, 1H), 0.90 (s, 9H), 0.13 (d, J = 1.4 Hz, 6H). |
| 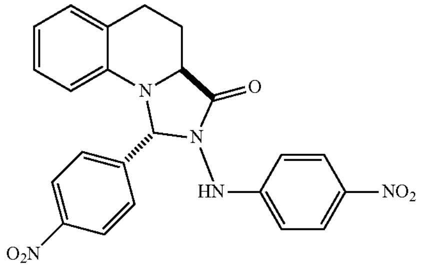 ZXD-78A | (400 MHz, DMSO-$d_6$) δ 9.50-9.10 (m, 1H), 8.40-8.20 (m, 2H), 8.15-7.95 (m, 2H), 7.93-7.80 (m, 2H), 7.08 (d, J = 7.5 Hz, 1H 6.88-6.42 (m, 3H), 6.20-5.90 (m, 2H), 4.80-4.55 (m, 1H), 3.01-2.87 (m, 2H), 2.35-2.29 (m, 1H), 1.90-1.60 (m, 1H). | 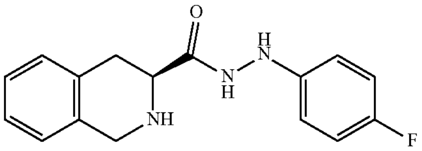 [SMILES: O=C(NNc1ccc(F)cc1)[C@@H]1Cc2ccccc2CN1] ZSD-54 | $^1$H NMR (400 MHz, DMSO-$d_6$) δ 9.92-9.68 (s, 1H), 7.74-7.70 (s, 1H), 7.16-7.10 (d, J = 2.5 Hz, 3H), 7.08-7.02 (d, J = 3.8 Hz, 1H), 7.01-6.95 (t, J = 8.9 Hz, 2H), 6.74-6.68 (m, 2H), 4.02-3.86 (q, J = 16.5 Hz, 2H), 3.59-3.51 (dd, J = 9.8, 4.7 Hz, 1H), 2.96-2.76 (qd, J = 16.1, 7.2 Hz, 2H). |

TABLE 7-continued compound structures and their NMR mass spectra

| Compound structures | Proton nuclear magnetic resonance spectrums | Compound structures | Proton nuclear magnetic resonance spectrums |
| --- | --- | --- | --- |
| 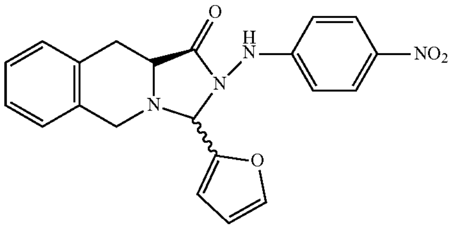 ZSD-27B | $^1$H NMR (400 MHz, DMSO-$d_6$) δ 9.20 (s, 1H), 7.88 (d, J = 8.9 Hz, 2H), 7.75 (s, 1H), 7.45-7.23 (m, 5H), 6.61 (d, J = 3.2 Hz, 1H), 6.48 (s, 1H), 6.10 (s, 1H), 5.33 (s, 1H), 4.08 (t, J = 5.6 Hz, 1H), 3.90 (d, J = 15.0 Hz, 1H), 3.74 (d, J = 14.9 Hz, 1H), 3.12-2.94 (m, 2H). | 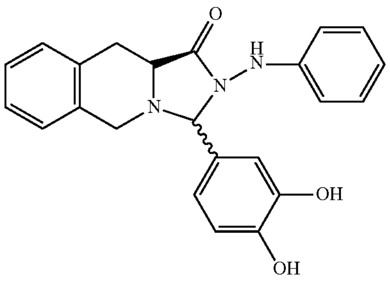 ZSD-30A | $^1$H NMR (400 MHz DMSO-$d_6$) δ 8.99 (s, 1H), 7.80 (s, 1H), 7.25 (d, J = 7.4 Hz, 1H), 7.22-7.13 (m, 2H), 7.13-7.06 (m, 3H), 6.89 (s, 1H), 6.74-6.60 (m, 5H), 5.03 (s, 1H), 3.72 (q, J = 14.4 Hz, 2H), 3.49 (d, J = 11.2 Hz, 1H), 3.10 (dd, J = 15.8, 3.9 Hz, 1H), 2.98-2.84 (m, 1H). |
| 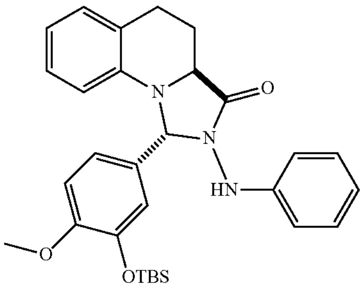 ZXD-165 | (400 MHz, DMSO-$d_6$) δ 8.07 (S, 1H), 7.11-6.97 (m, 5H), 6.97-6.90 (m, 1H), 6.92-6.84 (m, 1H), 6.69 (t, J = 7.7 Hz, 1H), 6.61 (m, 1H), 6.58-6.47 (m, 2H), 6.20 (d, J = 8.1 Hz, 1H), 5.65 (s, 1H), 4.47 (m, 1H), 3.75 (s, 3H), 3.03-2.91 (m, 1H), 2.89-2.80 (m, 1H), 2.35-2.24 (m, 1H), 1.71-1.54 (m, 1H), 0.91 (s, 9H), 0.07 (s, 3H), 0.05 (s, 3H). | 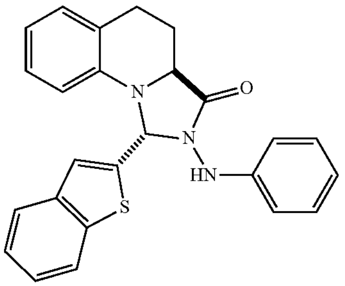 ZXD-178A | (400 MHz, DMSO-$d_6$) δ 8.24 (s, 1H), 8.01-7.93 (m, 1H), 7.88-7.82 (m, 1H), 7.68 (s, 1H), 7.42-7.35 (m, 2H), 7.12 (t, J = 7.6 Hz, 2H), 7.07 (d, J = 7.4 Hz, 1H), 6.95 (m, 1H), 6.73 (t, J = 7.3 Hz, 1H), 6.70-6.62 (m, 3H), 6.50 (d, J = 8.1 Hz, 1H), 6.28-6.17 (m, 1H), 4.39 (m, 1H), 3.01-2.84 (m, 2H), 2.36-2.29 (m, 1H), 1.69 (m, 1H). |

What is claimed is:
1. A pharmaceutical composition, comprising a compound selected from the group consisting of:
ZFD-33A+B
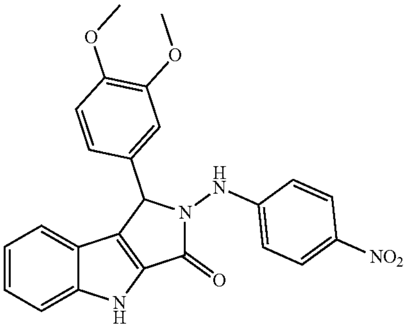
,
ZXN-10
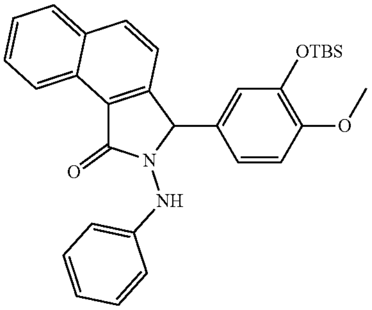
,
ZXD-157B
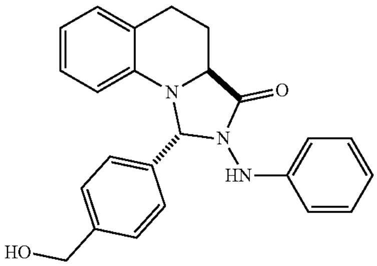
,
ZXD-165
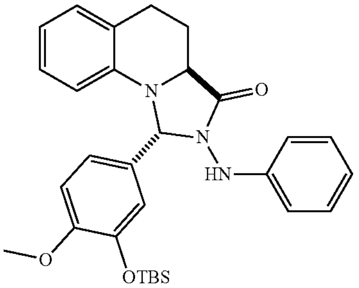
,
ZXD-167
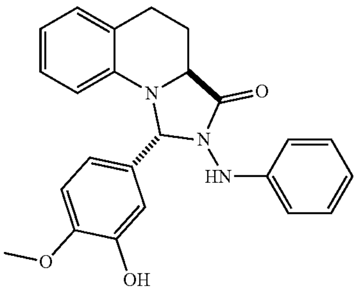
,
-continued
ZXD-176
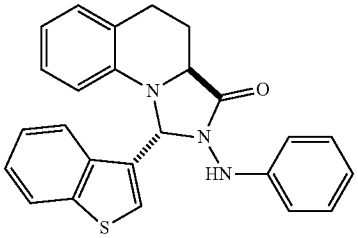
,
ZXD-178A
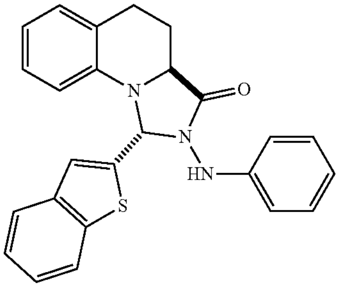
,
ZXD-178B
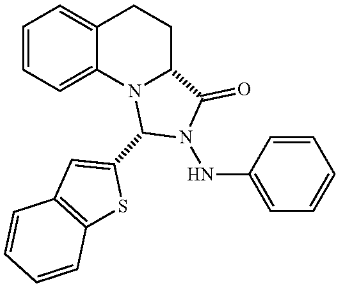
,
ZXD-181A
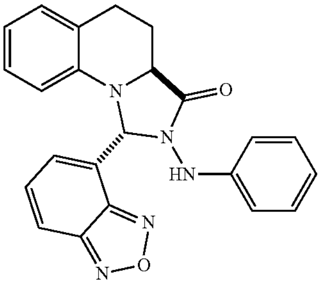
,
ZXD-131A
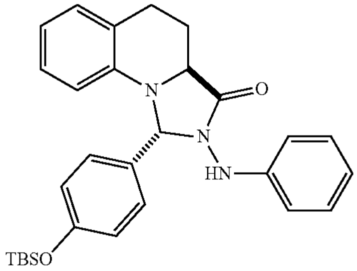
,

-continued
ZXD-131B
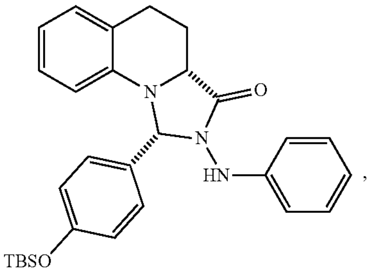
,
ZXD-132A
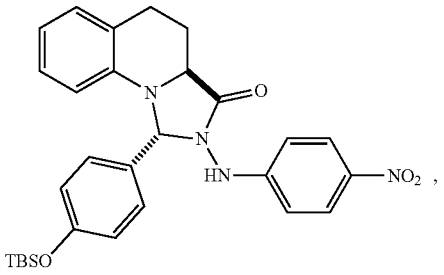
,
ZXD-133A
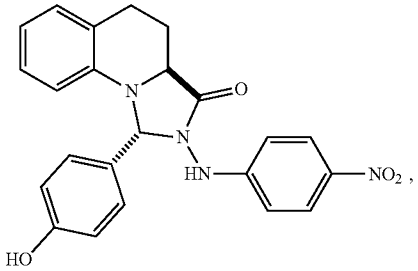
,
ZXD-140
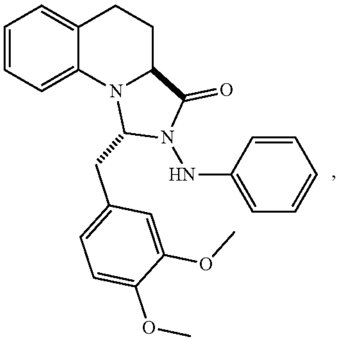
,
ZXD-142A
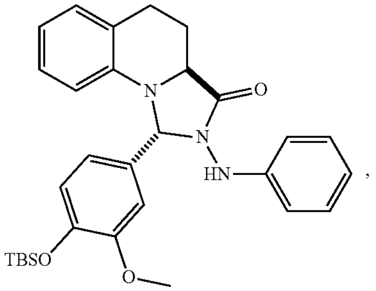
,
-continued
ZXD-147B
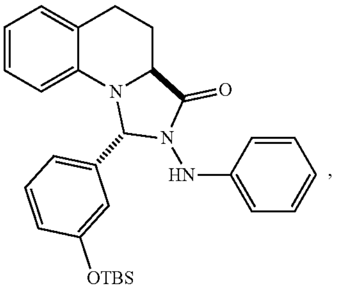
,
ZXD-156B
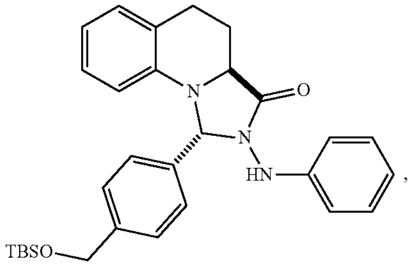
,
ZDL-19
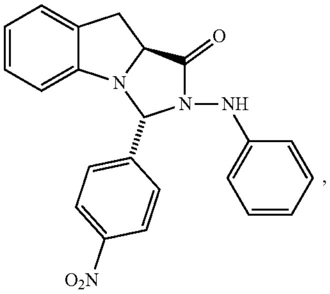
,
ZDL-21
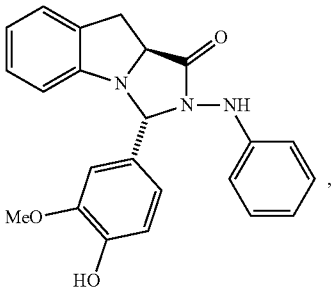
,
ZDL-89
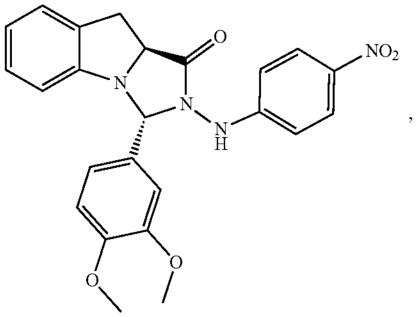
, -continued
ZDL-93
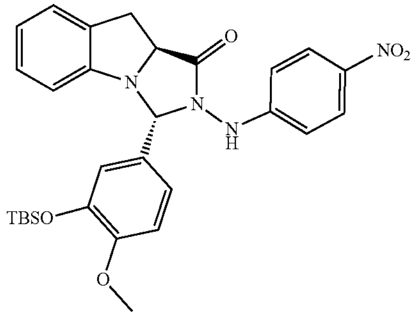
,
ZDL-94
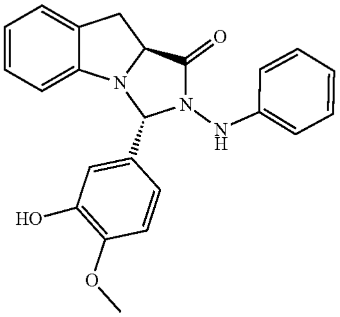
,
ZSD-18
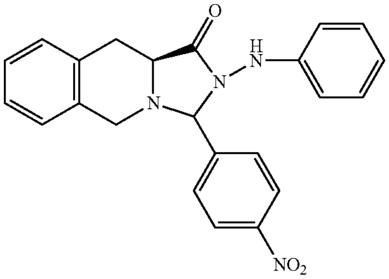
,
ZSD-20
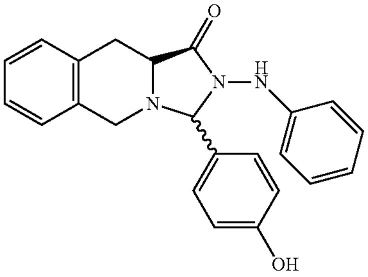
,
ZSD-27B
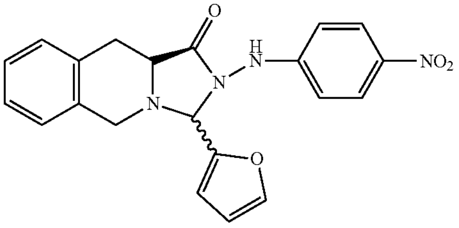
,
-continued
ZSD-28B
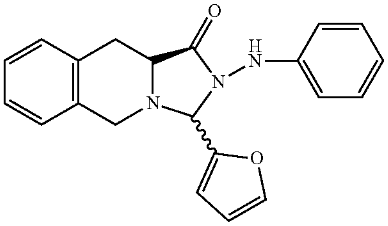
,
ZSD-30A
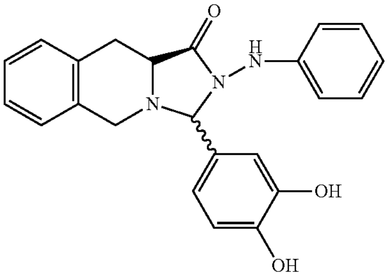
,
ZSD-32
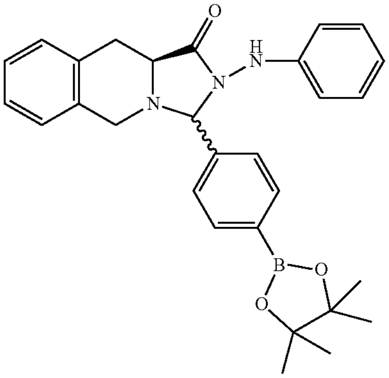
,
ZSD-36
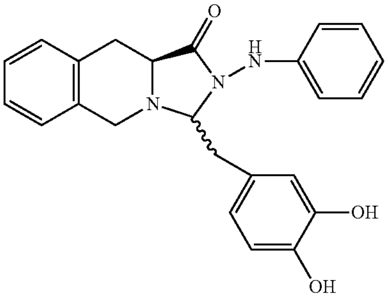
,
ZXD-100B
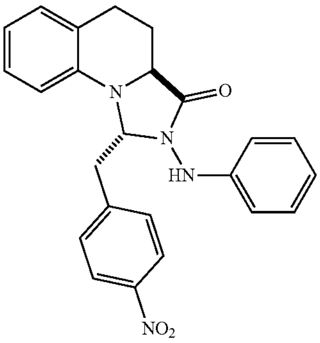
, -continued
ZXD-106
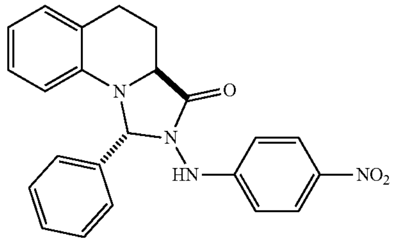
,
ZXD-107A
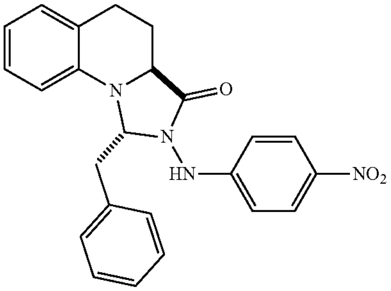
,
ZXD-109B
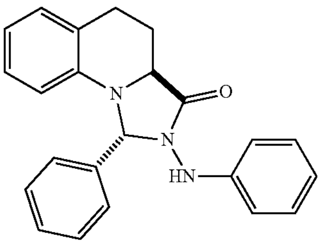
,
ZXD-120B
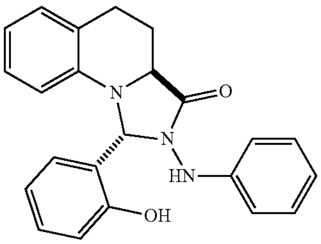
,
ZXD-126B
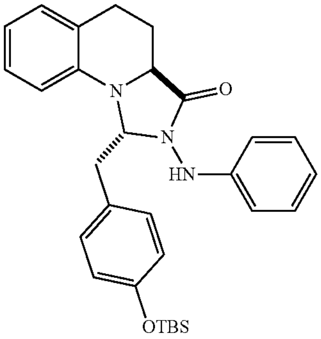
,
-continued
ZXD-127B
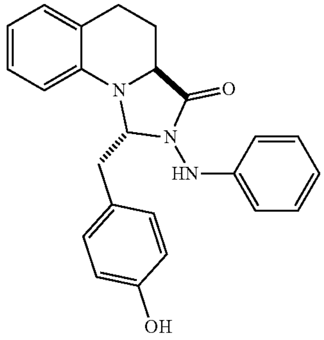
,
ZFD-44
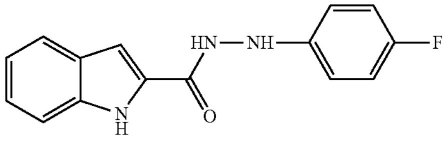
,
ZBM-36
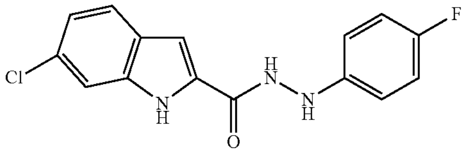
,
ZBM-24
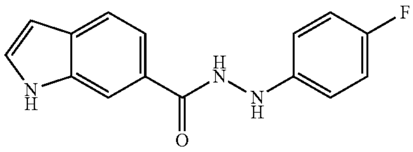
,
ZDL-101
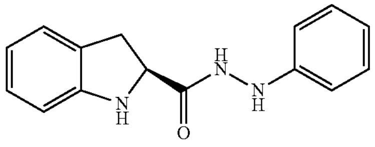
,
ZBM-5
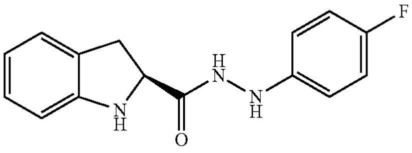
,
ZBM-6
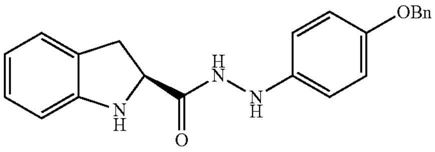
,
ZBM-8
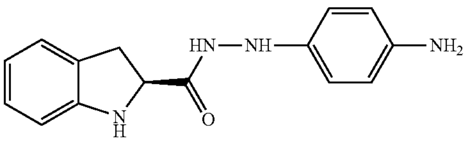
, -continued
ZBM-20
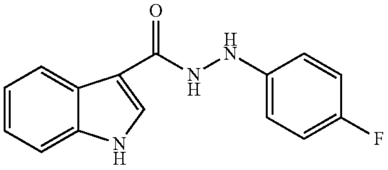
,
ZFD-38
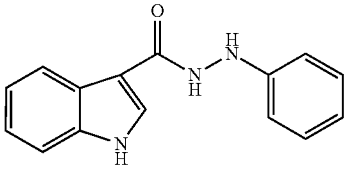
,
ZBM-15
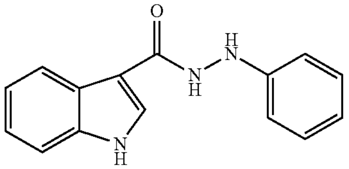
,
ZKD-21
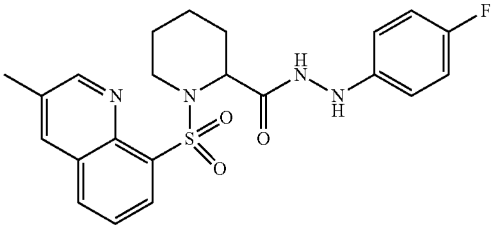
,
ZXD-F
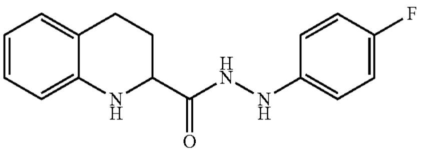
,
ZXD-44
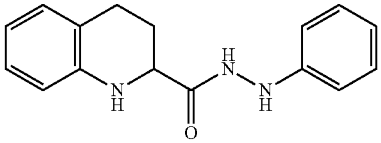
,
ZXD-45
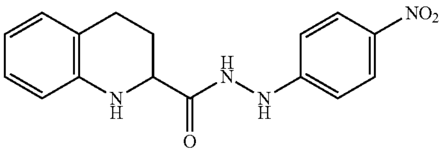
,
ZXD-51
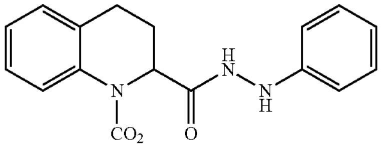
,
ZXD-72
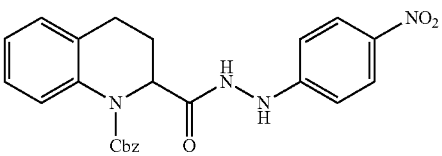
,
-continued
ZSD-15
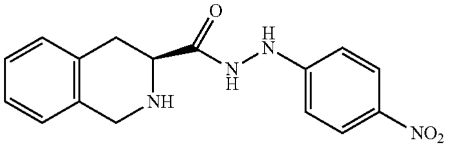
,
ZSD-16
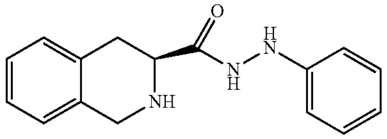
,
ZSD-54
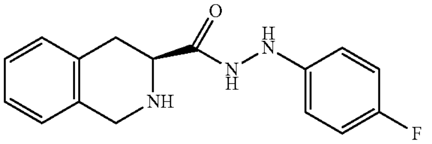
,
ZXD-70
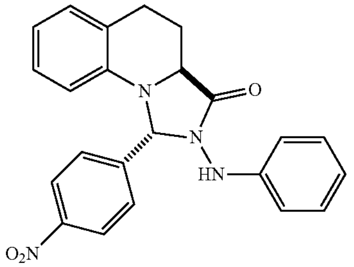
,
ZXD-78A
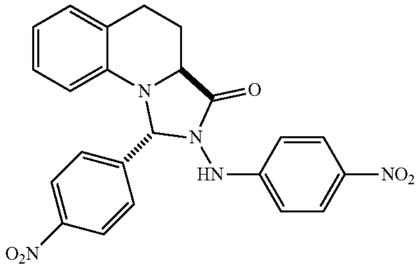
,
ZXD-86A
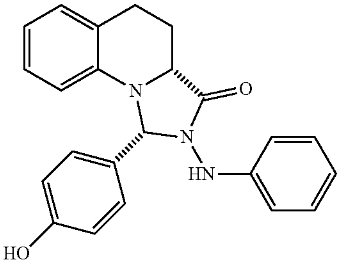
,
ZXD-86B
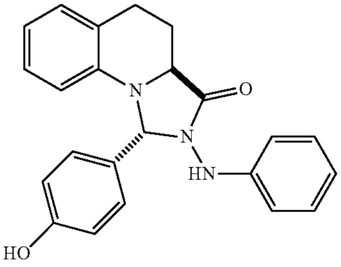
, -continued
ZKD-4A
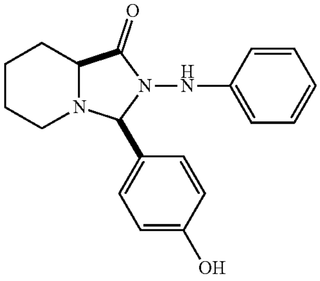
,
ZKD-4B
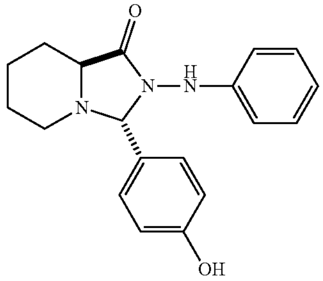
,
ZKD-5A
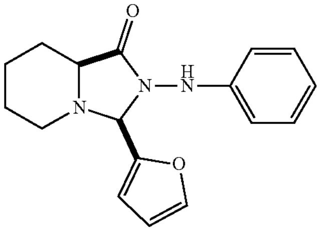
,
ZKD-5B
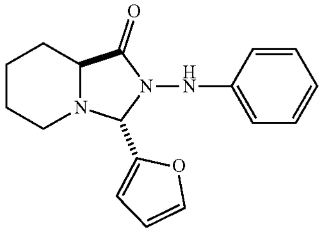
,
ZKD-6A
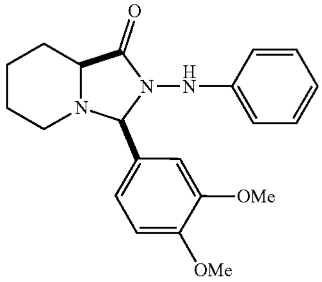
,
ZKD-6B
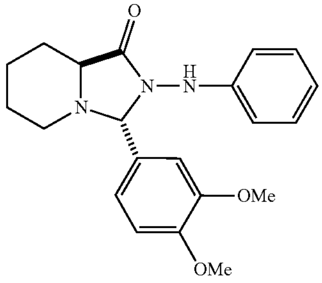
,
-continued
ZKD-7A
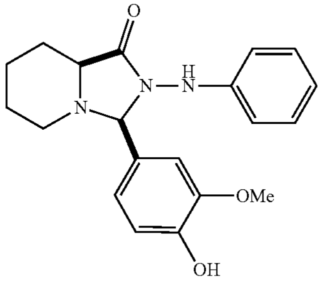
,
ZKD-7B
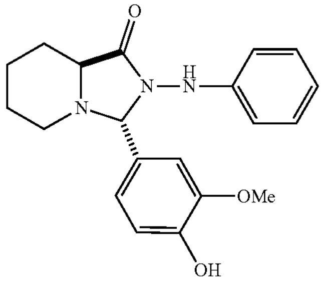
,
ZKD-8A
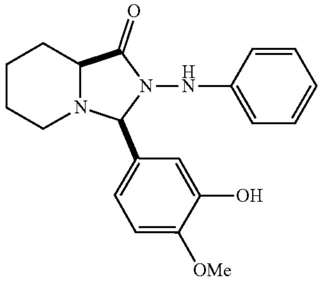
,
ZKD-8B
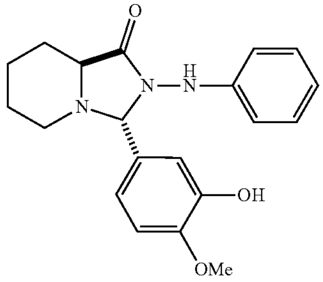
,
ZKD-10A
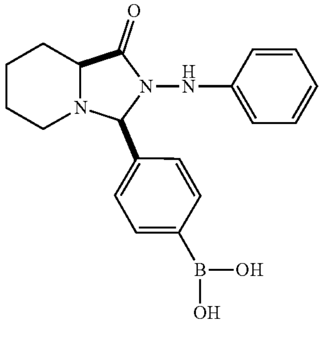
, -continued
ZKD-10B
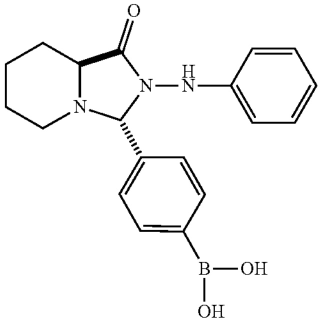
,
ZKD-12A
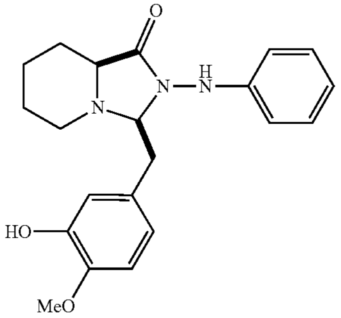
,
ZKD-12B
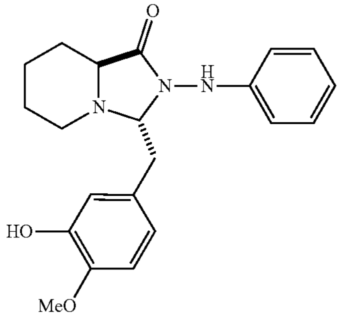
,
ZKD-13A
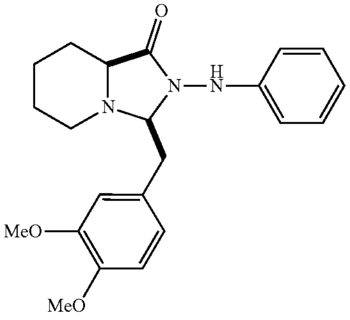
,
ZKD-13B
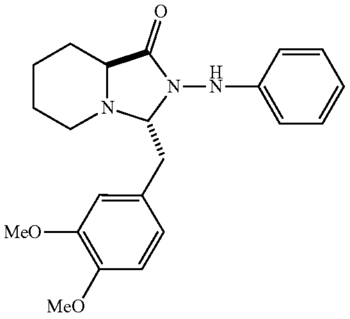
,
-continued
ZKD-14A
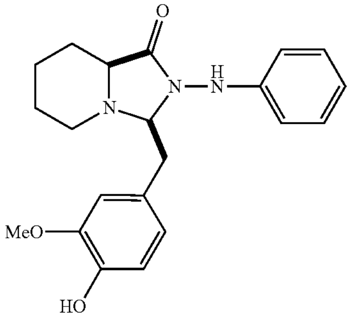
,
ZKD-14B
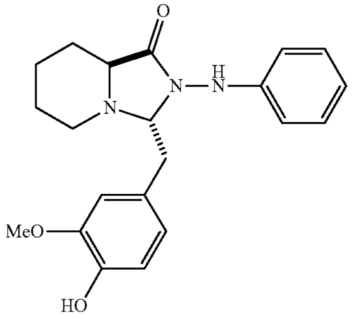
,
ZKD-15A
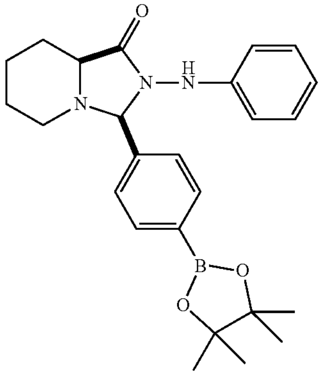
,
ZKD-15B
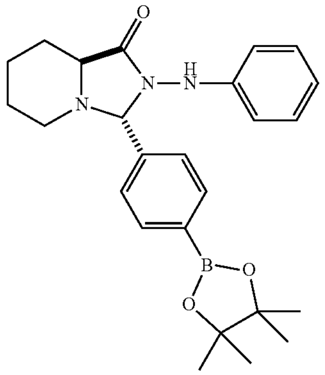
, -continued
ZKD-18A
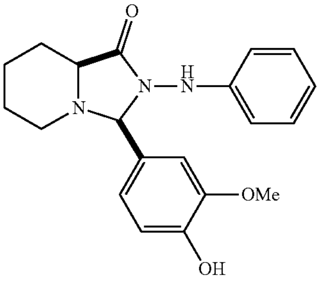
,
ZKD-18B
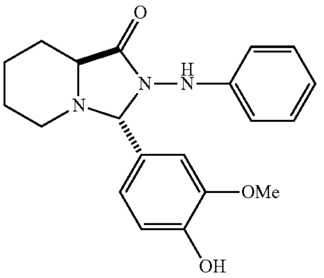
,
ZKD-19A
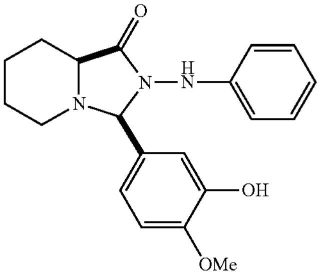
,
ZKD-19B
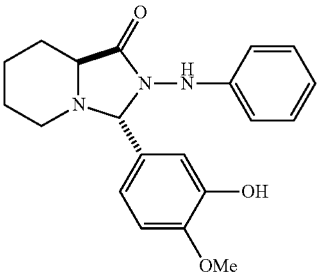
,
-continued
ZXD-87A
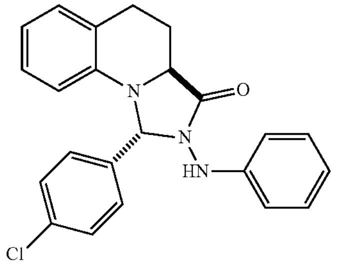
,
ZXD-89A
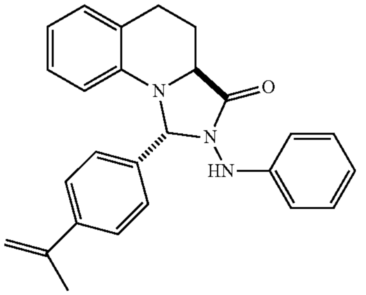
,
ZXD-95
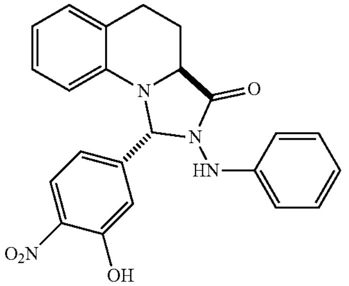
, and
ZXD-100A
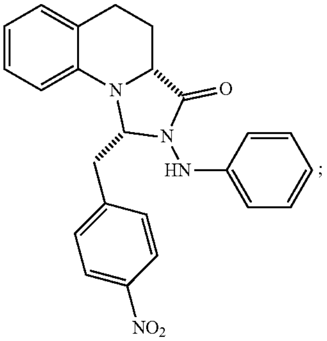
;
and
a pharmaceutically acceptable carrier.
* * * * *